(12) United States Patent
Bar et al.

(10) Patent No.: US 10,058,440 B2
(45) Date of Patent: Aug. 28, 2018

(54) CAROTID STENT APPARATUS AND METHODS FOR TREATMENT VIA BODY LUMENS

(71) Applicant: INSPIREMD, LTD, Tel Aviv (IL)

(72) Inventors: Eli Bar, Moshav (IL); Zeev Asher Holzer, Raanana (IL); Ofir Paz, Rishon Lezion (IL)

(73) Assignee: INSPIREMD, LTD. (IL)

( * ) Notice: Subject to any disclaimer, the term of this patent is extended or adjusted under 35 U.S.C. 154(b) by 0 days.

(21) Appl. No.: 14/500,759

(22) Filed: Sep. 29, 2014

(65) Prior Publication Data

US 2015/0032197 A1    Jan. 29, 2015

Related U.S. Application Data

(63) Continuation of application No. 11/920,972, filed as application No. PCT/IB2006/051874 on May 24, 2006.
(Continued)

(51) Int. Cl.
*A61F 2/07* (2013.01)
*A61F 2/92* (2013.01)
(Continued)

(52) U.S. Cl.
CPC .............. *A61F 2/92* (2013.01); *A61F 2/07* (2013.01); *A61F 2/958* (2013.01); *A61L 31/10* (2013.01);
(Continued)

(58) Field of Classification Search
CPC ............ A61F 2/07; A61F 2002/072–2002/077
(Continued)

(56) References Cited

U.S. PATENT DOCUMENTS

| 4,164,045 A | 8/1979 | Bokros et al. |
| 4,300,244 A | 11/1981 | Bokros et al. |

(Continued)

FOREIGN PATENT DOCUMENTS

| CN | 1414840 A | 4/2003 |
| EP | 0839506 | 5/1998 |

(Continued)

OTHER PUBLICATIONS

Fayad et al., "Clinical Imaging of the High-Risk or Vulnerable Atherosclerotic Plaque," American Heart Association, *Circulation Research*, vol. 89, pp. 305-316, Aug. 17, 2001.
(Continued)

*Primary Examiner* — Darwin Erezo
*Assistant Examiner* — Jonathan Hollm
(74) *Attorney, Agent, or Firm* — Haynes and Boone, LLP

(57) ABSTRACT

A stent assembly adapted to carotid arterial placement that includes a self-expanding support element comprising metal struts constructed to be positioned in a body lumen and expanded from a retracted state to an expanded state, and a knitted cover disposed over an exterior of the support element and along an entire length thereof, wherein the knitted cover comprises a single polymer fiber having a diameter of at least 40 nanometers to 30 microns, wherein the self-expanding support element and knitted cover together have apertures sized 20 microns to smaller than 100 microns in diameter to block larger debris when the stent assembly is placed in a carotid artery and expanded to the expanded state. Methods of stenting a carotid artery by applying the stent assembly to the carotid artery of a patient in need of treatment and expanding the stent assembly in situ are disclosed.

30 Claims, 21 Drawing Sheets

Related U.S. Application Data

(60) Provisional application No. 60/683,788, filed on May 24, 2005, provisional application No. 60/716,100, filed on Sep. 12, 2005, provisional application No. 60/742,460, filed on Dec. 5, 2005.

(51) Int. Cl.
*A61F 2/958* (2013.01)
*A61L 31/10* (2006.01)
*A61F 2/89* (2013.01)

(52) U.S. Cl.
CPC ............ *A61F 2/89* (2013.01); *A61F 2002/075* (2013.01); *A61F 2002/077* (2013.01); *A61F 2230/0054* (2013.01); *A61F 2230/0067* (2013.01); *A61F 2250/0023* (2013.01); *A61F 2250/0039* (2013.01); *A61L 2300/20* (2013.01)

(58) Field of Classification Search
USPC .... 606/108; 623/1.11–1.13, 1.23, 1.38–1.39, 623/1.42, 1.44
See application file for complete search history.

(56) References Cited

U.S. PATENT DOCUMENTS

| | | | |
|---|---|---|---|
| 4,321,711 A | 3/1982 | Mano | |
| 4,425,908 A | 1/1984 | Simon | |
| 4,723,549 A | 2/1988 | Wholey et al. | |
| 4,832,688 A | 5/1989 | Sagae et al. | |
| 4,865,017 A | 9/1989 | Shinozuka | |
| 4,873,978 A | 10/1989 | Ginsburg | |
| 4,969,891 A | 11/1990 | Gewertz | |
| 4,990,156 A | 2/1991 | Lefebvre | |
| 4,998,539 A | 3/1991 | Delsanti | |
| 5,019,090 A | 5/1991 | Pinchuk et al. | |
| 5,122,154 A | 6/1992 | Rhodes | |
| 5,152,777 A | 10/1992 | Goldberg et al. | |
| 5,171,233 A | 12/1992 | Amplatz et al. | |
| 5,192,286 A | 3/1993 | Phan et al. | |
| 5,236,447 A * | 8/1993 | Kubo et al. | 623/1.13 |
| 5,330,482 A | 7/1994 | Gibbs et al. | |
| 5,342,348 A * | 8/1994 | Kaplan | 604/891.1 |
| 5,366,504 A * | 11/1994 | Andersen et al. | 623/1.5 |
| 5,382,261 A | 1/1995 | Palmaz | |
| 5,383,887 A | 1/1995 | Nadal | |
| 5,403,341 A | 4/1995 | Solar | |
| 5,421,955 A | 6/1995 | Lau et al. | |
| 5,470,313 A | 11/1995 | Crocker et al. | |
| 5,486,183 A | 1/1996 | Middleman et al. | |
| 5,569,295 A | 10/1996 | Lam et al. | |
| 5,591,228 A | 1/1997 | Edoga | |
| 5,628,788 A * | 5/1997 | Pinchuk | 623/1.2 |
| 5,676,696 A * | 10/1997 | Marcade | 623/1.35 |
| 5,713,948 A | 2/1998 | Uflacker | |
| 5,769,884 A * | 6/1998 | Solovay | 623/1.13 |
| 5,824,037 A * | 10/1998 | Fogarty et al. | 623/1.13 |
| 5,827,324 A | 10/1998 | Cassell et al. | |
| 5,833,651 A | 11/1998 | Donovan et al. | |
| 5,843,116 A | 12/1998 | Crocker et al. | |
| 5,843,161 A | 12/1998 | Solovay | |
| 5,871,538 A | 2/1999 | Dereume | |
| 5,908,448 A | 6/1999 | Roberts et al. | |
| 5,919,225 A | 7/1999 | Lau et al. | |
| 5,941,896 A | 8/1999 | Kerr | |
| 5,984,955 A | 11/1999 | Wisselink | |
| 6,007,543 A | 12/1999 | Ellis et al. | |
| 6,015,430 A | 1/2000 | Wall | |
| 6,015,432 A | 1/2000 | Rakos et al. | |
| 6,027,517 A | 2/2000 | Crocker et al. | |
| 6,030,414 A | 2/2000 | Taheri | |
| 6,042,597 A | 3/2000 | Kveen et al. | |
| 6,066,167 A | 5/2000 | Lau et al. | |
| 6,077,273 A | 6/2000 | Euteneuer et al. | |
| 6,096,027 A | 8/2000 | Layne | |
| 6,152,144 A | 11/2000 | Lesh et al. | |
| 6,159,239 A * | 12/2000 | Greenhalgh | A61F 2/07 623/1.13 |
| 6,176,875 B1 | 1/2001 | Lenker et al. | |
| 6,178,346 B1 | 1/2001 | Amundson et al. | |
| 6,245,089 B1 | 6/2001 | Daniel et al. | |
| 6,254,627 B1 | 7/2001 | Freidberg | |
| 6,261,320 B1 | 7/2001 | Tam et al. | |
| 6,263,880 B1 | 7/2001 | Parker et al. | |
| 6,306,162 B1 | 10/2001 | Patel | |
| 6,322,585 B1 * | 11/2001 | Khosravi | A61F 2/07 623/1.11 |
| 6,334,868 B1 * | 1/2002 | Ham | 623/1.13 |
| 6,340,364 B2 | 1/2002 | Kanesaka | |
| 6,348,065 B1 | 2/2002 | Brown et al. | |
| 6,357,104 B1 | 3/2002 | Myers | |
| 6,361,558 B1 | 3/2002 | Hieshima et al. | |
| 6,369,039 B1 | 4/2002 | Palasis et al. | |
| 6,371,962 B1 | 4/2002 | Ellis et al. | |
| 6,383,171 B1 | 5/2002 | Gifford et al. | |
| 6,432,129 B2 | 8/2002 | DiCaprio | |
| 6,436,132 B1 | 8/2002 | Patel et al. | |
| 6,443,979 B1 * | 9/2002 | Stalker et al. | 623/1.11 |
| 6,447,796 B1 | 9/2002 | Vook et al. | |
| 6,451,051 B2 | 9/2002 | Drasler et al. | |
| 6,461,381 B2 | 10/2002 | Israel et al. | |
| 6,464,722 B2 | 10/2002 | Israel et al. | |
| 6,468,230 B2 | 10/2002 | Muni et al. | |
| 6,488,703 B1 | 12/2002 | Kveen et al. | |
| 6,497,722 B1 * | 12/2002 | Von Oepen et al. | 623/1.13 |
| 6,506,203 B1 | 1/2003 | Boyle et al. | |
| 6,540,773 B2 | 4/2003 | Dong | |
| 6,554,855 B1 | 4/2003 | Dong | |
| 6,602,285 B1 | 8/2003 | Von Oepen et al. | |
| 6,626,939 B1 * | 9/2003 | Burnside | A61F 2/07 623/1.38 |
| 6,641,607 B1 | 11/2003 | Hossainy et al. | |
| 6,645,239 B1 | 11/2003 | Park et al. | |
| 6,669,717 B2 | 12/2003 | Marotta et al. | |
| 6,669,961 B2 | 12/2003 | Kim et al. | |
| 6,673,814 B2 | 1/2004 | Joshi et al. | |
| 6,676,695 B2 | 1/2004 | Solem | |
| 6,682,554 B2 | 1/2004 | Oepen et al. | |
| 6,702,849 B1 | 3/2004 | Dutta et al. | |
| 6,712,834 B2 | 3/2004 | Yassour et al. | |
| 6,712,842 B1 | 3/2004 | Gifford, III et al. | |
| 6,755,856 B2 | 6/2004 | Fierens et al. | |
| 6,802,851 B2 | 10/2004 | Jones et al. | |
| 6,805,706 B2 * | 10/2004 | Solovay | A61F 2/07 623/1.13 |
| 6,808,533 B1 | 10/2004 | Goodwin et al. | |
| 6,818,014 B2 | 11/2004 | Brown et al. | |
| 6,827,731 B2 | 12/2004 | Armstrong et al. | |
| 6,835,189 B2 | 12/2004 | Musbach et al. | |
| 6,893,457 B2 | 5/2005 | Dong | |
| 6,902,522 B1 | 6/2005 | Walsh et al. | |
| 6,918,920 B1 | 7/2005 | Wang et al. | |
| 6,919,100 B2 | 7/2005 | Narayanan | |
| 6,929,658 B1 | 8/2005 | Freidberg et al. | |
| 6,932,832 B2 | 8/2005 | Patel et al. | |
| 6,939,374 B2 | 9/2005 | Banik et al. | |
| 6,939,376 B2 | 9/2005 | Shulze et al. | |
| 6,953,476 B1 | 10/2005 | Shalev | |
| 6,981,986 B1 | 1/2006 | Brown et al. | |
| 6,997,946 B2 | 2/2006 | Girton et al. | |
| 7,011,676 B2 | 3/2006 | Dong | |
| 7,037,330 B1 | 5/2006 | Rivelli, Jr. et al. | |
| 7,041,129 B2 | 5/2006 | Rourke et al. | |
| 7,083,644 B1 | 8/2006 | Moroni | |
| 7,198,638 B2 | 4/2007 | Dong | |
| 7,491,225 B2 | 2/2009 | Weber et al. | |
| 7,722,634 B2 | 5/2010 | Panetta et al. | |
| 7,996,993 B2 | 8/2011 | Gray et al. | |
| 8,043,323 B2 | 10/2011 | Holzer et al. | |
| 8,097,015 B2 | 1/2012 | Devellian et al. | |
| 8,961,526 B2 | 2/2015 | Holzer et al. | |
| 2002/0022860 A1 | 2/2002 | Borillo et al. | |
| 2002/0045917 A1 | 4/2002 | Ambrisco et al. | |
| 2002/0082685 A1 * | 6/2002 | Sirhan et al. | 623/1.42 |

(56) References Cited

U.S. PATENT DOCUMENTS

| | | |
|---|---|---|
| 2002/0111668 A1 | 8/2002 | Smith |
| 2002/0128679 A1 | 9/2002 | Turovskiy et al. |
| 2002/0156523 A1* | 10/2002 | Lau .................. A61F 2/88 623/1.13 |
| 2002/0161393 A1 | 10/2002 | Demond et al. |
| 2003/0028239 A1* | 2/2003 | Dong .................. 623/1.13 |
| 2003/0055452 A1 | 3/2003 | Joergensen et al. |
| 2003/0074049 A1 | 4/2003 | Hoganson et al. |
| 2003/0083646 A1 | 5/2003 | Sirhan et al. |
| 2003/0093112 A1 | 5/2003 | Addis |
| 2003/0100945 A1 | 5/2003 | Yodfat et al. |
| 2003/0130718 A1 | 7/2003 | Palmas et al. |
| 2003/0149464 A1 | 8/2003 | Dong |
| 2003/0176884 A1 | 9/2003 | Berrada et al. |
| 2003/0209835 A1 | 11/2003 | Chun et al. |
| 2003/0229389 A1 | 12/2003 | Escano |
| 2004/0030377 A1 | 2/2004 | Dubson et al. |
| 2004/0054402 A1 | 3/2004 | DiCarlo |
| 2004/0068314 A1 | 4/2004 | Jones et al. |
| 2004/0116960 A1 | 6/2004 | Demond et al. |
| 2004/0143272 A1 | 7/2004 | Cully et al. |
| 2004/0158312 A1 | 8/2004 | Chouinard et al. |
| 2004/0225322 A1 | 11/2004 | Garrison et al. |
| 2004/0236407 A1 | 11/2004 | Fierens et al. |
| 2004/0260384 A1 | 12/2004 | Allen |
| 2004/0267347 A1 | 12/2004 | Cervantes |
| 2004/0267352 A1 | 12/2004 | Davidson et al. |
| 2004/0267354 A1* | 12/2004 | Ringeisen et al. ........... 623/1.42 |
| 2005/0038503 A1 | 2/2005 | Greenhalgh et al. |
| 2005/0049680 A1 | 3/2005 | Fischell et al. |
| 2005/0085847 A1 | 4/2005 | Galdonik et al. |
| 2005/0110214 A1 | 5/2005 | Shank et al. |
| 2005/0119688 A1 | 6/2005 | Bergheim |
| 2005/0171591 A1 | 8/2005 | McHale et al. |
| 2005/0182473 A1 | 8/2005 | Eidenschink et al. |
| 2005/0187140 A1 | 8/2005 | Hunter et al. |
| 2005/0222607 A1 | 10/2005 | Palmer et al. |
| 2005/0240261 A1 | 10/2005 | Rakos et al. |
| 2005/0277976 A1 | 12/2005 | Galdonik et al. |
| 2006/0009835 A1* | 1/2006 | Osborne et al. ............. 623/1.13 |
| 2006/0085064 A1 | 4/2006 | Tuch |
| 2006/0116748 A1 | 6/2006 | Kaplan et al. |
| 2006/0155359 A1 | 7/2006 | Watson |
| 2006/0175727 A1 | 8/2006 | Fierens et al. |
| 2006/0259131 A1 | 11/2006 | Molaei et al. |
| 2006/0259137 A1 | 11/2006 | Artof et al. |
| 2007/0043428 A1 | 2/2007 | Jennings et al. |
| 2007/0135890 A1 | 6/2007 | Dong |
| 2007/0179593 A1 | 8/2007 | Fierens et al. |
| 2007/0179601 A1 | 8/2007 | Fierens et al. |
| 2007/0208374 A1 | 9/2007 | Boyle et al. |
| 2007/0213800 A1 | 9/2007 | Fierens et al. |
| 2007/0270902 A1 | 11/2007 | Slazas et al. |
| 2007/0276468 A1 | 11/2007 | Holzer et al. |
| 2008/0023346 A1 | 1/2008 | Vonderwalde |
| 2008/0132999 A1* | 6/2008 | Mericle .................. A61F 2/07 623/1.34 |
| 2008/0172082 A1 | 7/2008 | Holzer et al. |
| 2009/0012598 A1 | 1/2009 | Abbate et al. |
| 2009/0138070 A1 | 5/2009 | Holzer et al. |
| 2009/0248133 A1 | 10/2009 | Bloom et al. |
| 2010/0056907 A1 | 3/2010 | Rappaport et al. |
| 2010/0204772 A1 | 8/2010 | Holzer et al. |
| 2010/0222805 A1 | 9/2010 | Pal et al. |
| 2010/0241214 A1 | 9/2010 | Holzer et al. |
| 2010/0324651 A1 | 12/2010 | Holzer et al. |
| 2010/0324664 A1 | 12/2010 | Holzer et al. |
| 2011/0098739 A1 | 4/2011 | Bates |

FOREIGN PATENT DOCUMENTS

| | | |
|---|---|---|
| WO | WO 198809683 A1 | 12/1988 |
| WO | WO 199929262 A1 | 6/1999 |
| WO | WO 200130266 A1 | 5/2001 |
| WO | WO 2003018079 | 3/2003 |
| WO | WO 2003022325 A2 | 3/2003 |
| WO | WO 2006000130 | 1/2006 |
| WO | WO 2006116636 A1 | 11/2006 |
| WO | WO 2006126182 A2 | 11/2006 |
| WO | WO 2007067451 A2 | 6/2007 |
| WO | WO 2008047367 | 4/2008 |
| WO | WO 2008047368 | 4/2008 |
| WO | WO 2008047369 | 4/2008 |
| WO | WO 2008062414 A2 | 5/2008 |

OTHER PUBLICATIONS

Liistro et al., "Late Acute Thrombosis After Paclitaxel Eluting Stent Implantation," *HEART Medical Journal*, vol. 86, pp. 262-264. Sep. 2001.

Zakarija et al., "Clopidogrel-Associated TTP: An Update of Pharmacovigilance Efforts Conducted by Independent Researchers, Pharmaceutical Suppliers, and the Food and Drug Administration," *STROKE—Journal of American Heart Association* , vol. 35, pp. 533-537, Jan. 5, 2004.

Haj et al., "Acquired Haemophilia A May be Associated with Clopidogrel," *British Medical Journal*, vol. 329, p. 323, Aug. 7, 2004.

Nguyen et al.,"Resistance to Clopidogrel: A Review of the Evidence," *Journal of the American College of Cardiology*, vol. 45, No. 8, pp. 1157-1164, Apr. 19, 2005.

International Patent Application PCT/IL07/01253, Written Opinion and International Search Report from International Searching Authority, dated Jun. 13, 2008.

International Patent Application PCT/IL07/01442, Written Opinion and International Search Report from International Searching Authority, dated Aug. 27, 2008.

International Patent Application PCT/IL07/01255, Written Opinion and International Search Report from International Searching Authority, dated Sep. 25, 2008.

International Patent Application PCT/IL07/01254, Written Opinion and International Search Report from International Searching Authority, dated Sep. 30, 2008.

International Patent Application PCT/IB2006/051874, Written Opinion from International Searching Authority, dated Nov. 30, 2006.

International Application PCT/IB2011/055758, Written Opinion and International Search Report from International Searching Authority, dated May 14, 2012.

European Patent Application No. 07827415.6, Search report from European Patent Office dated Feb. 13, 2013.

European Patent Application No. 07827227.5 Search report from European Patent Office dated Feb. 25, 2013.

European Patent Application No. 07827228.3 Search report from European Patent Office dated Mar. 8, 2013.

\* cited by examiner

CAROTID STENT APPARATUS AND METHODS FOR TREATMENT VIA BODY LUMENS

CROSS-REFERENCE TO RELATED APPLICATIONS

This application is a continuation of application Ser. No. 11/920,972, filed Nov. 23, 2007, which is a national stage of PCT/IB2006/051874, filed May 24, 2006, which claims the benefit under 35 U.S.C. § 119(e) of U.S. Provisional Applications No. 60/683,788, filed on May 24, 2005, No. 60/716,100, filed on Sep. 12, 2005, and, No. 60/742,460, filed Dec. 5, 2005. The entire contents of each of these prior applications is incorporated herein in its entirety by express reference thereto.

FIELD OF THE INVENTION

Carotid stent assemblies and methods are provided for treatment and/or support via body lumens and in other hollow organs.

BACKGROUND OF THE INVENTION

A stenosis is a stricture of a canal or duct. In the context of the vascular system a stenosis is a narrowing of the lumen of a blood vessel. A stenosis can severely restrict blood flow and promote thrombosis which can lead to myocardial infarction or stroke, for example. A common type of primary stenosis is caused by a buildup of atherosclerotic plaque.

Several therapeutic methods have been developed to improve circulation and homeostasis in stenotic vessels including by-pass surgery and revascularization procedures. Revascularization procedures (e.g. balloon angioplasty, bare metal stents as well as drug eluting stents, atherectomy, rotary ablation (rotablation)) serve to improve blood flow by reducing or removing the stenosis. However, these procedures frequently injure the blood vessel. The biological response to the injury is a multifactorial fibro-proliferative process that is similar to wound healing, and includes the elaboration of growth factors from a variety of cell types, infiltration of leukocytes, migration and proliferation of smooth muscle cells, the production of extracellular matrix and tissue remodeling. The process can result in the formation of a thick neointima within the vessel wall which reduces the luminal area of the vessel (e.g. restenosis). Various levels of restenosis occur following about 20-50% of coronary angioplasty procedures.

Attempts have been made at reducing restenosis following vascular intervention procedures by, for example, placing endovascular stents at the location of the stenosis. At present, this treatment sometimes itself causes restenosis. Stents are typically implanted within a vessel in a contracted state and expanded when in place in the vessel in order to maintain integrity of the vessel and to allow fluid flow through the vessel. Typically, implantation of stents is accomplished by mounting the stent on the balloon portion of a catheter, positioning the stent in a vascular lumen, and expanding the stent to an expanded state by inflation of the balloon within the stent. The stent can then be left in place by deflating the balloon and removing the catheter. One problem with stenting according to this widely used procedure, however, is that as the stent expands, it engages relatively brittle plaque lining the arterial tissues surrounding the stent, not the arterial tissue itself. In doing so, the expanding stent cracks the plaque to produce debris. This debris, in an untended condition, then enters the blood stream and occasionally injures the patient further by causing a vessel blockage downstream. This debris release is exacerbated by the fact that conventional stent structure contains large gaps, enabling the debris to move freely into the bloodstream. This debris creating effect is especially problematic when stenting in the carotid arteries, where the downstream blood flow leads directly to the brain and debris can cause strokes. In coronary arteries, debris is particularly dangerous because it can lead to heart attacks.

Currently, protection against this debris is carried out during the stenting procedure by using a downstream embolic shower protection device. This sort of device acts as a filter which traps debris of a predetermined size from transiting through the cardiovascular system. There are a number of drawbacks with using these embolic shower protection devices as they exist currently. One drawback is that they often encompass using another device, in addition to the balloon catheter which must be inserted into the patient, adding time and potential danger to the procedure. Another drawback is that the protection device must be downstream of the stent location, therefore, some additional stretch of vasculature must be available in order to properly position the protection device. Yet another drawback is that the embolic shower protection device is removed at the conclusion of the stenting procedure and therefore does not provide any protection after that point, despite the fact that post procedure debris can become potentially dislodged as a result of the procedure. Yet another drawback is that the embolic shower protection device is placed some distance from the stent, thus possibly leaving some close side branches unprotected.

Another common practice in use with stenting procedures is the use of stents for administering pharmacologic agents to treat restenosis and other body ailments through the lumen walk. Because of the mechanical strength that is required to properly support vessel walls, stents are typically constructed of metallic struts. However, these struts are often constructed to be thin because, in general, foreign material in the body is to be avoided and because of the need to obtain a stent that can be crimped, flexible and conform with the blood vessel anatomy. Arterial stents are built to cover a minimum amount of the blood vessel's walls, while still having a high radial force in order to avoid collapsing and thus keeping the lumen open. Typically, the metal struts cover only about 10% of the total covered area, and the stent somewhat resembles a cylindrical fishing net. However, one-drawback with these stents is that pharmaceuticals are placed only on the stent struts, which cover only a small portion of the blood vessel's wall, and they do not cover the apertures in the stent. Thus the therapeutic effects of the drug are achieved only on a small portion of the injured tissue. Since some pharmaceuticals are comprised of large molecules, with a very high molecular weight, and/or complicated and/or wide stereochemistry, and which have limited diffusion capabilities, there is a large area of tissue which is not effectively treated. Another drawback of current drug eluting stents is that in attempts to overcome the diffusion issues, an excessive amount of drug must be eluted in the hopes that it will permeate to the target tissue. In some cases, this causes undesirable overdosing of the tissue areas closest to the stem struts in addition to the added expense of using copious amounts of the drug. Furthermore, there are design limits which prevent increasing the amount of drug embedded and thus, eluted from the stent.

U.S. Patent Publication No. 2004/0030377 to Dubson et al., the contents of which are herein incorporated by reference, describes a stent assembly which is designed to deliver pharmaceuticals to a blood vessel after implantation while encouraging endothelial growth.

Today's drug eluting stents suffer from higher incidences of sub-acute thrombosis than the previous generations of bare metal stents. Longer administration period of anticoagulant drugs like Plavix® is needed, with additional cost and more side effects for the patients. The main reason for the sub-acute and the chronic thrombosis is sudden exposure of a small area of the stent strut to the blood stream. The small area of exposed stent typically happens when several adjacent endothelial cells fall from the stent strut surface leaving an exposed area of the strut structure and producing a site on which blood platelets can clot. Even if the patient is being treated with anticoagulants, there is a very high risk that the platelets will stick to the exposed stent and cause clotting. This phenomenon may lead to a total occlusion of the blood vessel and to an immediate myocardial infarction. Drug eluting stents are more susceptible to such incidences since the conformity and the integrity of the endothelial cells covering the polymer is not as good as when they are covering a bare metal stent.

SUMMARY OF THE INVENTION

An aspect of some embodiments of the invention relates to providing an enhanced stent apparatus which includes at least one porous structure and optionally a support element (e.g. a stent) at least partially covered by the porous structure. In an embodiment of the invention, the porous structure has a thickness of less than 100 microns. Optionally, the porous structure has a thickness of less than 20 microns. Optionally, the porous structure has a thickness of less than 10 microns. Optionally, the porous structure is of varying thickness. In an embodiment of the invention, the porous structure is comprised of at least one fiber whose thickness is less than 100 microns. Optionally, the porous structure is comprised of at least one fiber whose thickness is less than 20 microns. In an embodiment of the invention, the porous structure is comprised of at least one fiber whose thickness is less than 10 microns. In some exemplary embodiments of the invention, the porous structure is comprised of at least one fiber whose thickness is in the range of 40 nm to 40 microns. In some embodiments of the invention, the fiber thickness is in the order of the thickness of the porous structure. For example, the fiber thickness is at least half the thickness of the porous structure.

In some exemplary embodiments of the invention, the porous structure is placed on the exterior of the stent support element, "exterior" meaning between the support element and a body lumen wall. In some embodiments, a porous structure is placed on the interior of the stent support element. Optionally, a porous structure is placed both on the exterior and the interior of the stent. In some embodiments of the invention, the porous structure and/or the support element are used to treat the lumen with pharmaceuticals. In some embodiments of the invention, the porous structure is at least temporarily secured to the support element. For example, to facilitate insertion and deployment of the enhanced stent apparatus in a patient.

In an exemplary embodiment of the invention, at least one fiber's thickness is less than the diameter of an endothelial cell. In some exemplary embodiments of the invention, the porous structure's thickness is less than the diameter of an endothelial cell. In some exemplary embodiments of the invention, the fiber diameter is on the same approximate order of size (e.g. diameter or French (circumference)) as a typical endothelial cell (about 100 microns square, e.g. 3×30 microns).

In some embodiments of the invention, the porous structure is comprised of at least one super-fiber which is comprised of a plurality of bundled fibers. In an embodiment of the invention, the super-fiber has an overall thickness of less than 100 microns. Optionally, the super-fiber has an overall thickness of less than 20 microns. Optionally, the super-fiber has an overall thickness of less than 10 microns.

In some embodiments of the invention, the porous structure and/or the stent are placed over a balloon-type catheter, like an angioplasty balloon and are balloon expandable. In some embodiments of the invention, the porous structure and/or the stent are self-expandable. In some embodiments of the invention, the porous structure expands with the support element during deployment, whether with the angioplasty balloon or via self-expansion.

In an embodiment of the invention, at least the porous structure is made of a resorbable polymer. Optionally, the stent is made of a resorbable polymer. Optionally, the porous structure is made out of a resorbable and/or degradable polymer. In some embodiments of the invention, at least one polymer is used as a cover for the stent and/or porous structure. In some embodiments of the invention, the stent and/or the porous structure are made up a plurality of layers which exhibit different performance characteristics depending on the desired result. For example, some layers do not include pharmaceutical agents, where as some optionally do.

In an exemplary embodiment of the invention, the apertures and/or the stent's struts and/or the fiber thicknesses of the porous structure are sized to encourage growth of endothelial cells therethrough but to prevent transmission of particulate debris greater than a predetermined size, thereby also providing embolic shower protection. In an exemplary embodiment of the invention, the fiber diameter and/or French size is used as a measure for choosing at least one fiber for constructing the porous structure. The apertures sizes are optionally designed to capture and hold any plaque, greater than a predetermined size, which may be dislodged from the lumen wall. The size of the apertures may vary in some exemplary embodiments of the invention. Optionally, the porous structure is comprised of apertures averaging no greater than 80 microns in diameter. Optionally, the porous structure is comprised of apertures averaging no greater than 200 microns in diameter. Optionally, the porous structure is comprised of apertures between 200 and 1500 microns in diameter (see description of diameter as being approximate or used in lieu of French, herein).

In an embodiment of the invention, under 30% of the porous structure surface area is dedicated to structure, leaving the remaining 70% of the porous structure surface area as empty space, or apertures. In embodiments where the porous structure is placed on a support element, this means at the most, 30% of the support element is covered, or in other words, the coverage area of the porous structure is 30%. Optionally, the coverage area of the porous structure is less than 20%. Optionally, the coverage area of the porous structure is less than 15%. Optionally, the coverage area of the porous structure is less than 5%. Coverage area in the above described context should not be confused with embodiments wherein the porous structure is placed on only a portion of the support element, which would reduce the "coverage area" of the porous structure even further, depending on how much of the support element on which the porous structure is placed. For example, the porous structure extends the entire length of the support element and provides less than 30% coverage area, due to being comprised of 70% apertures. If the same 30% coverage area porous structure is overlaid only on half of the support structure, then the coverage area would be reduced to 15%, due to half of the support structure being completely uncovered and only 30% of the other half of the support structure being covered. In an embodiment of the invention, the coverage area of the porous structure is adapted to be minimized while still performing an intended lumen treating function, such as those described herein.

In some exemplary embodiments of the invention, the coverage area, fibers and/or apertures are sized in order to allow easy diffusion of endothelial cells through the porous structure and/or to facilitate growth of the endothelial cell layer.

In an exemplary embodiment of the invention, taking various factors into account such as fiber thickness in diameter (or French), porous structure thickness, aperture size, and/or coverage area, the porous structure resembles a fishing net in configuration. Optionally, the porous structure resembles a web configuration. Optionally, the porous structure resembles a mesh configuration.

In some embodiments of the invention, the porous structure is constructed to reduce the likelihood of endothelial cells falling off the porous structure, thereby reducing the chance of blood clots, embolization and exposure of the structure to body substances (e.g. blood) within the lumen. Optionally, endothelial cells are encouraged to remain on the porous structure by making the porous structure thickness on the order of or less than an endothelial cell.

In some exemplary embodiments of the invention, the porous structure is used to control the local pressure exerted by the enhanced stent apparatus on the body lumen wall. For example, by increasing or decreasing the surface area of the porous structure as it at least partially covers the stent, the pressure exerted by the enhanced stent apparatus per unit area can be altered. In an embodiment of the invention, pressure control is used to reduce the likelihood of the enhanced stent apparatus causing plaque to break off of the lumen wall. In some embodiments of the invention, local pressure control is used to reduce the likelihood of tissue trauma caused by stent implants, thereby enhancing protection against stenosis/restenosis and/or scarring of the lumen tissue. In an embodiment of the invention, local pressure control also permits the support element struts to be reduced in size.

An aspect of some embodiments of the invention relates to exemplary methods of manufacturing a porous structure, which is optionally coaxial to a lumen and/or a support element, which has small apertures (aperture sizes described herein). In some exemplary embodiments of the invention, the porous structure is knitted and/or woven and/or braided and/or interlaced.

In some exemplary embodiments of the invention, the porous structure is comprised of at least one substantially inelastic fiber, however the knitted and/or woven and/or braided and/or interlaced and/or porously dipped and/or electrospun structure of the porous structure is adapted and constructed to be at least partially elastic. In an embodiment of the invention, this means that some or all the elasticity of the porous structure is achieved due to the structure of the interlaced and/or crimped and/or textured fibers rather than through the elastic properties of an elastomer. For example, a knitted porous structure may be expanded even if it is made of a non-stretchable material like metal. In an embodiment of the invention, a crimped stent can expand from as little as 0.3 mm up to 3 mm and from 1 mm to as much as 8 mm, for example.

In an exemplary embodiment, the porous structure is made by a knitting method, made out of at least one fiber, having a diameter up to 100 microns (and/or French up to 0.1). In an embodiment of the invention, the structure of the porous structure is controlled by modifying the density of the needles in the manufacturing head used to manufacture the knitted porous structure. In an embodiment of the invention, the manufacturing head used to manufacture the porous structure has between 20 and 35 needles. Optionally, the head used has between 30 and 45 needles. Optionally, the head used has between 35 and 80 needles. In some embodiments of the invention, the structure of the porous structure is controlled by controlling the tension (i.e. slack) on the at least one fiber being used to manufacture the porous structure. For example, loop or eye shape and size are controllable by increasing or reducing the inlet and/or outlet tension on the fiber, or the stitch length, being used for manufacturing the porous structure.

In some exemplary embodiments of the invention, the porous structure is manufactured by knitting a porous structure, from a fine polymer thread and/or from a fine metal wire. In some exemplary embodiments of the invention, the metal wire is coated with at least one layer of a polymer. In an embodiment of the invention, the polymer layer is 2 microns thick. In an embodiment of the invention, the polymer layer contains at least one pharmaceutical. Optionally, more than one polymer layer is used.

In some exemplary embodiments of the invention, at least one fiber used to construct the porous structure is combined with a more durable fiber which allows handling, knitting and/or the production of the porous structure. Optionally, the durable fiber is dissolvable or degradable, thus after producing a desired porous structure (by knitting for example), the porous structure is put into a substance for dissolving or degrading the more durable fiber, leaving only original fiber in the porous structure. This allows production of the porous structure with materials that by themselves would not be durable to survive the manufacturing process.

In some embodiments of the invention, some individual eyes or loops of the porous structure are secured to itself in order to prevent "run outs" and/or unraveling. For example, if one loop becomes unraveled, the next loop in the chain does not follow suit due to it being stitched closed.

In some exemplary embodiments of the invention, the porous structure is manufactured by a dipping technique, using a polymeric solution mixed with an inorganic salt such as sodium chloride, in order to have controlled sized apertures after dissolving the salt out. In some exemplary embodiments of the invention, laser cutting is used to control the aperture size of the polymer. In some exemplary embodiments of the invention, the polymeric solution may include pharmaceuticals.

In some exemplary embodiments of the invention, the porous structure is manufactured with at least one pharmaceutically coated and/or imbued fiber. Optionally, at least one pharmaceutical agent is added after porous structure manufacture. Optionally, the porous structure does not contain any pharmaceutical agents. Optionally, at least one pharmaceutical agent is added to a polymer used for coating the porous structure.

In some exemplary embodiments of the invention, the porous structure is manufactured for use without an underlying support element. In some embodiments of the invention, the porous structure is manufactured separately from the support element and is added to the support element subsequently.

In an embodiment of the invention, the porous structure is wound and/or spun onto a support element. In some exemplary embodiments of the invention, the porous structure is placed on the support element in a pattern resembling a helical coil. Optionally, the porous structure is placed on the support element in a pattern resembling a plurality of intertwined helical coils.

In some exemplary embodiments of the invention, other methods are used to manufacture an enhanced stent apparatus for use, such as manufacturing the porous structure and/or the support element and then placing them on an angioplasty balloon. Optionally, portions of the balloon are not covered by the porous structure. Optionally, at least the porous structure is longer than the balloon. Optionally, at least the porous structure is placed on an at least partially inflated balloon. Optionally, at least the porous structure is placed on a deflated balloon. Optionally, the porous structure is manufactured around a shaped flexible core which can be subsequently removed. In some embodiments of the invention, the porous structure is electrospun onto the balloon. Optionally, portions of the balloon are masked to prevent electrospinning of the porous structure on undesirable areas of the balloon.

In an exemplary embodiment of the invention, the diameter of at least the porous structure is reduced during or after manufacture in order to facilitate delivery of the enhanced stent apparatus to the treatment site. In an embodiment of the invention, the diameter of a polymer porous structure is reduced by heat shrinking it onto the support element. Heat shrinking is optionally performed between the $T_g$ and the $T_m$ of at least one polymer material in the porous structure. In an embodiment of the invention, the porous structure is folded to reduce its diameter for insertion into a patient. Optionally, the porous structure is folded into "n" folds.

An aspect of some exemplary embodiments of the invention relates to securing a porous structure to a support element, such as a stent, thereby creating an enhanced stent apparatus. In some exemplary embodiments of the invention, a porous structure and the support element are secured together to prevent the porous structure from becoming dislodged from the support element during navigation through a lumen during delivery. In some embodiments of the invention, the porous structure and the support element are only temporarily secured together, for example by dipping the porous structure into an albumin solution. Optionally, the solution contains bovine serum albumin.

In some exemplary embodiments of the invention, the porous structure and the support element are provided with at least one common or partially common polymer coating which is cured at the same time, thereby attaching the porous structure to the support element. Optionally, curing is performed with one or more of heat and/or pressure. Optionally, an adhesive is used to at least temporarily secure the porous structure and the support element together. In some exemplary embodiments of the invention, the support element is situated between external and internal polymer-coated porous structures, wherein the porous structures are cured together thereby securing the support element between them.

In some embodiments of the invention, the porous structure and the support element are attached together using an adhesive.

In some embodiments of the invention, the porous structure and the support element are stitched together in at least one location. Optionally, the porous structure and the support element are stitched together at least at the ends of the support element. Optionally, the porous structure and the support element are stitched together at least at the center of the support element. In some embodiments of the invention, the porous structure and the support element are stitched together temporarily with biodegradable and/or bioresorbable fibers. For example, the porous structure and the support element may only be fastened together for hours or days. Optionally, they are secured together long enough for implantation of the enhanced stent apparatus. Temporary fastening of the porous structure to the support element allows for navigation through the patient to the treatment site without the dislodgement of the porous structure from the support element, while ensuring that the fastener (e.g. stitches) does not irritate the lumen surface for an extended period of time. It should be noted, that other temporary and/or bioresorbable and/or or biodegradable fasteners such as glue, clips, flexible rings, polymer layers and the like, could be used to secure the porous structure and the support element together for delivery.

In some embodiments of the invention, the porous structure and the support element are attached together at a plurality of locations, using for example sliding connections, such as they do not restrict the expandability of the knitted porous structure. In some embodiments of the invention, the porous structure and support element are attached together along the circumference of the support element, optionally along the circumference at the end of the support element.

In some exemplary embodiments of the invention, the porous structure includes art additive material which improves the stiffness or other mechanical properties of the porous structure, at least temporarily until it arrives at a treatment site in a lumen. Optionally the material is fibrogane. Optionally, the material is albumin fibrogane helonic acid. Optionally, the material is dissolved in the course of hours or a few days by naturally occurring substances in the body, such as enzymes.

In some exemplary embodiments of the invention, a porous structure is used in conjunction with a support element and an angioplasty balloon. In some exemplary embodiments of the invention, the porous structure is provided with an adhesive material adapted to allow porous structure to adhere to the lumen being treated but not to the balloon, for removal of the balloon from the lumen but not the porous structure. For example, adhesive is optionally provided on the lumen, or exterior, side of the porous structure but not the balloon side.

In some exemplary embodiments of the invention, the porous structure is provided around a balloon wherein it is attached securely enough to not become dislodged during delivery but to not remain attached to balloon at time of deployment. Optionally, porous structure is coated with a material which has a higher affinity for the interior surface of a lumen than the balloon upon the application of an implantation pressure. Optionally, an implantation pressure is no greater than 20 atm but the porous structure still adheres to the lumen due to the coating.

An aspect of some exemplary embodiments of the invention relates to eluting pharmaceuticals from an enhanced stent apparatus assisted by endothelial cell growth, optionally enabling greater control of administered pharmaceutical dosage. In some exemplary embodiments of the invention, pharmacological therapy commences or continues after the enhanced stent apparatus is expected to be encapsulated by endothelial cell growth. Optionally, pharmacological treatment commences after some endothelial cell growth is expected through and/or around the enhanced stent apparatus. Optionally, pharmacological treatment begins upon implantation without regard to endothelial cell growth. In an embodiment of the invention, endothelial cell layer growth is expected to substantially cover the porous structure within hours of enhanced stent apparatus implantation.

In some exemplary embodiments of the invention, the enhanced stent apparatus is adapted and constructed to time-release pharmaceuticals in accordance with a predetermined treatment schedule. Optionally, the predetermined treatment schedule accommodates anticipated and/or actual endothelial cell growth rates and/or reduces inflammatory response by utilizing a coating with a predetermined breakdown rate. In some exemplary embodiments of the invention, delivered pharmaceuticals are at least: antimicrobial, antibiotic, anti-proliferative, anti-thrombotic, anti-coagulant, and/or anti-platelet. Optionally, delivered pharmaceuticals include growth factors, tissue engineering, material and/or liposomes.

In some exemplary embodiments of the invention, only a porous structure, without a support element, is used to perform pharmacological treatment. Optionally, the porous structure contains pharmaceuticals. Optionally, the support element (e.g. stent) contains pharmaceuticals. Optionally, the porous structure and the support element contain pharmaceuticals.

An aspect of some exemplary embodiments of the invention relates to enabling the use of large molecule and/or complex stereochemistry pharmaceuticals with a lumen treating porous structure. Due to the poor diffusion abilities of large sized and/or complex stereochemistry molecules the widely spaced stent struts are typically not sufficient to provide adequate large molecule diffusion. Usage of large and/or complex stereochemistry molecules is optionally encouraged by reducing the average distance between the tissue to be treated and the pharmaceutical source (e.g. the porous structure). In an exemplary embodiment of the invention, this is optionally achieved by placing a porous-structure on the exterior surface of a lumen treating stent, where the porous structure has smaller aperture sizes than the stent and overlaps at least a portion of the apertures of the stent. In an exemplary embodiment of the invention, the increased drug eluting surface area abutting the lumen wall provides a shorter travel distance for the pharmaceutical from the porous structure to the lumen and optionally beyond into the rest of the patient's body over the travel distance that would have existed from the widely spaced stent struts. Optionally, diffusion of large sized and/or complex stereochemistry molecules is improved using a porous structure with a coverage area of less than 25%.

An aspect of some exemplary embodiments of the invention relates to uses of a porous structure. In some exemplary embodiments of the invention, the porous structure is implanted in a lumen without a support element (e.g. a stent). In some exemplary embodiments of the invention, the porous structure is implanted at a lumen treatment site and then optionally a support element is implanted subsequently at the treatment site. Optionally, the porous structure is implanted on the interior of the support element.

In an exemplary embodiment of the invention, angioplasty balloons are used to implant the porous structure to provide long-term clinical effects. Typically, angioplasty balloon treatments suffer from the fact that their influences are limited to acute, short period effects.

In some exemplary embodiments of the invention, an enhanced stent apparatus including the porous structure and a stent is used to reduce the likelihood of stenosis and/or restenosis in a previously treated area.

In an exemplary embodiment of the invention, usage of the porous structure offers treatment to small blood vessels (smaller than 2 millimeters) where stents cannot be used, for example in the small coronaries like diagonals.

In some exemplary embodiments of the invention, an enhanced stent apparatus is used to treat areas with potential vulnerable plaque rupture.

In some exemplary embodiments of the invention, the porous structure is longer than the support element, thus allowing therapeutic coverage over a larger area offered by porous structure.

In some exemplary embodiments of the invention, the porous structure is used to treat vein grafts, for example saphenous vein grafts. Optionally, pharmacological therapy rendered from the porous structure is used to accelerate vein to artery conversion.

In some exemplary embodiments of the invention, the porous structure is used to allow treatments through the brain blood barrier ("BBB"). Optionally, treatment through the BBB is performed using at least one pharmaceutical eluted from the porous structure. In an embodiment of the invention, the pharmaceutical locally opens the BBB so systemic and/or locally applied pharmaceuticals, such as cancer treating pharmaceuticals, can cross.

In some embodiments of the invention, carotid arteries are treated using at least a porous structure as described herein. For example, embolic shower protection is optionally provided for carotid applications wherein debris as small as 20 microns in diameter is caught by porous structure.

In some exemplary embodiments of the invention, bile ducts are treated using at least a porous structure as described herein. For example, the bile ducts often become congested with debris (e.g. cholesterol), which restricts flow. Treatment of the bile ducts using enhanced stent apparatus may increase the diameter of the bile ducts, improving their operation.

In some embodiments of the invention, renal arteries are treated using at least a porous structure as described herein. For example, embolic shower protection is optionally provided for renal applications wherein debris as small as 50 microns in diameter is caught by porous structure.

In some embodiments of the invention, veins are treated using at least a porous structure as described herein. For example, embolic shower protection is optionally provided for veins below the knee wherein debris as small as 70 microns in diameter is caught by porous structure.

In some exemplary embodiment of the invention, at least the porous structure as described herein is used to treat aneurisms. Optionally, brain aneurisms are treated using the porous structure such that the structure prevents an embolic coil from projecting into a lumen proximal to the aneurism. In some embodiments of the invention, treatment of aneurisms is performed without the use of a scrambled wire mass, wherein the porous structure restricts flow to the aneurism, and/or instigates the creation of a clot within the aneurism which eventually solidifies it.

In an exemplary embodiment of the invention, the porous structure as described herein is used to treat embolic showers instigated by stent deployment.

An aspect of some exemplary embodiments of the invention relates to reducing the likelihood of endothelial cells, or clumps of cells, falling off the porous structure, thereby reducing the chance of embolization and reducing the risk of exposure of the support structure to body substances (e.g. blood) within the lumen. In an embodiment of the invention, endothelial cells are encouraged to remain on the porous structure by making the porous structure thickness on the order of an endothelial cell or smaller, allowing an individual endothelial cell, and the endothelial cell layer as a whole, to be well-anchored to the basal intimal layer. Optionally, the linear nature and/or single cell width dimension of the endothelial cell layer reduces the likelihood of embolization occurring on an exposed section of the porous structure. Optionally, the design of porous structure which encourages rapid endothelial cell growth replaces endothelial cells lost before embolization can occur.

There is thus provided in accordance with an exemplary embodiment of the invention an enhanced stent apparatus, comprising: a support element, wherein said support element is constructed to be positioned in a body lumen; and, a porous structure, said porous structure located on a surface of said support element, and wherein the porous structure is comprised of at least one fiber under 30 microns in diameter, has a coverage area of less than 30% and is provided with apertures. Optionally, the porous structure is comprised of at least one fiber under 20 microns in diameter and has a coverage area of less than 20%. Optionally, the apertures have an average diameter of less than 200 microns. Optionally, the apertures have an average diameter of less than 100 microns. Optionally, the porous structure has a thickness less than 100 microns. Optionally, the porous structure has a thickness less than 20 microns. Optionally, the apertures of said porous structure pass through the porous structure. Optionally, the porous structure is adapted to elute a pharmacological agent therefrom. Optionally, at least one fiber and the apertures are sized to encourage the growth of endothelial cells therethrough. Optionally, the apertures are sized to permit the passage of red blood cells therethrough. Optionally, at least one of said support element and said porous structure are expandable. In an embodiment of the invention, at least one of said support element and said porous structure are self-expandable. In an embodiment of the invention, the porous structure is knitted. In an embodiment of the invention, the knitted porous structure resembles a fishing net. In an embodiment of the invention, the porous structure is woven. In an embodiment of the invention, the porous structure is braided. In an embodiment of the invention, the porous structure is electrospun. In an embodiment of the invention, the porous structure is interlaced. In an embodiment of the invention, the porous structure is at least temporarily secured to said support element. Optionally, the porous structure is at least temporarily secured to said support element using an adhesive. Optionally, the porous structure is at least temporarily secured to said support element using at least one stitch. Optionally, at least one stitch is loose, permitting porous structure to slide in relation to said support element. Optionally, the porous structure is at least temporarily secured to said support element using a biodegradable material. Optionally, the porous structure is temporarily secured to said support element for less than 7 days. Optionally, the porous structure is temporarily secured to said support element for less than 4 days. Optionally, the porous structure is temporarily secured to said support element for less than a day. Optionally, the porous structure is temporarily secured to said support element for the duration of delivery of said enhanced stent apparatus to a treatment site. Optionally, delivery lasts for 6 hours or less. Optionally, delivery lasts for 3 hours or less. Optionally, delivery lasts for 1 hour or less. Optionally, at least one fiber contains at least one polymer. Optionally, at least one fiber is comprised of a polymer. Optionally, at least one fiber is provided with at least one polymer coating. Optionally, at least one fiber is comprised of a plurality of polymer coatings. Optionally, the polymer is biodegradable. Optionally, the polymer is bioresorbable. Optionally, at least two of the plurality of polymer coatings exhibit different performance characteristics. Optionally, a performance characteristic is a degradation time. Optionally, the performance characteristic is a pharmaceutical to be eluted. Optionally, the performance characteristic is a surface modification treatment. Optionally, the performance characteristic is stickiness to the lumen. Optionally, at least the porous structure of the enhanced stent apparatus is attached to a catheter using a material that is less adhesive to at least the porous structure of an enhanced stent apparatus than at least the porous structure of an enhanced stent apparatus is to an interior surface of said body lumen upon the application of pressure. Optionally, an external polymer coating has a degradation time timed to the growth of an endothelial cell layer. Optionally, at least one of said support element and said porous structure elute at least one pharmaceutical into the lumen. Optionally, at least one of the support element and the porous structure are at least one of biodegradable or bioresorbable.

There is thus provided in accordance with an exemplary embodiment of the invention, a method of stenting a body lumen, comprising: removably placing at least the porous structure of an enhanced stent apparatus on a catheter adapted for insertion into said body lumen; navigating at least the porous structure of an enhanced stent apparatus to an area within said body lumen; lodging at least the porous structure of an enhanced stent apparatus at said area within said body lumen; detaching at least the porous structure of an enhanced stent apparatus from said catheter; and, removing said catheter. Optionally, the catheter is a balloon catheter. Optionally, removably placing includes attaching at least the porous structure of an enhanced stent apparatus to said catheter to prevent said porous structure slipping off of the catheter during said navigating. Optionally, at least the porous structure of an enhanced stent apparatus is removably placed on said catheter using an adhesive. Optionally, removably placing comprises attaching at least the porous structure of an enhanced stent apparatus to said catheter using a material that is less adhesive to at least the porous structure of an enhanced stent apparatus than at least the porous structure of an enhanced stent apparatus is to an interior surface of said body lumen upon the application of pressure. Optionally, at least the porous structure of the enhanced stent apparatus is stiffened during navigation by treating the porous structure with a stiffening biodegradable material. Optionally, at least the porous structure of the enhanced stent apparatus is stiffened using fibrogane. Optionally, at least the porous structure of the enhanced stent apparatus is stiffened using albumin fibrogane helonic acid. Optionally, the body lumen is a carotid artery. Optionally, the body lumen is a coronary artery. Optionally, the body lumen is a cerebral artery. Optionally, the body lumen is a renal artery. Optionally, the body lumen is a saphenous vein graft. Optionally, the body lumen is a vein. Optionally, the body lumen is a bile duct.

There is thus provided in accordance with an exemplary embodiment of the invention a method of treating a lumen, comprising: implanting at least a pharmaceutical-eluting porous structure within said lumen; waiting for sufficient endothelial cell overgrowth; and, eluting the pharmaceutical from said porous structure. In an embodiment of the invention, the method further comprises stimulating endothelial cell overgrowth between said implanting and said waiting. Optionally, endothelial cell overgrowth is around and through said porous structure. Optionally, sufficient endothelial cell overgrowth fully encapsulates said porous structure. Optionally, sufficient endothelial cell overgrowth at least partially encapsulates porous structure. Optionally, a determination of sufficient growth is related to the pharmaceutical being eluted. Optionally, the pharmaceutical provides one or more of the following effects: cell growth modification, encourages endothelial cell growth, reduces neointima growth, is anti-proliferative, is anti-thrombotic, is anti-coagulant, is anti-inflammatory, is anti-platelet, is a tissue engineering factor, is an immunomodulator, is antioxidant, is an antisense oligonucleotide, is a collagen inhibitor, is hydrophobic, or is hydrophilic. Optionally, the pharmaceutical is at least one of sirolimus, zolimus, zotarolimus, paclitaxel, a taxane, tacrolimus, everolimus, vincritine, viblastine, a HMG-CoA reductase inhibitor, doxorubicin, colchicine, actinomycin D, mitomycin C, cyclosporine, mycophenolic acid, triazolopyrimidine, a triazolopyrimidine derivative, intrapidene, dexamethasone, methylprednisolone, gamma interferon, heparin, a heparin-like dextran derivative, acid citrate dextrose, coumadin, warfarin, streptokinase, anistreplase, tissue plasminogen activator (tPA), urokinease, abciximab, probucol, tranilast angiopeptin, c-myc, c-myb, halofuginone, batimistat, a liposome, gemcitabine, Rapamycin, VEGF, FGF-2, a micro carriers containing endothelial cells, a genes, DNA, an endothelial cell seed, or a hydrogel containing endothelial cells. Optionally, the pharmaceutical is comprised of at least one of a steroid or a statin.

There is thus provided in accordance with an exemplary embodiment of the invention a method of treating from a lumen, comprising: imbuing at least the porous structure of the enhanced stent apparatus with a large molecular weight pharmaceutical; implanting at least the porous structure within said lumen; wherein said large molecular weight pharmaceutical has a molecular weight greater than 700 Daltons. Optionally, the molecular weight is greater than 3,000 Daltons. Optionally, the molecular weight is up to 50,000 Daltons. In an exemplary embodiment of the invention, the method further comprises waiting for sufficient endothelial cell overgrowth over said porous structure prior to eluting said large molecule pharmaceutical. Optionally, sufficient overgrowth fully encapsulates said porous structure. Optionally, sufficient overgrowth at least partially encapsulates porous structure. Optionally, endothelial cell overgrowth is around and through said porous structure. Optionally, said large molecular weight pharmaceutical is comprised of liposomes. Optionally, said large molecular weight pharmaceutical is comprised of steroids. Optionally, said large molecular weight pharmaceutical is comprised of statins. Optionally, said large molecular weight pharmaceutical is comprised of anticoagulants. Optionally, said large molecular weight pharmaceutical is comprised of gemcitabine. Optionally, said large molecular weight pharmaceutical is comprised of at least one of a zolimus or zotarolimus pharmaceutical.

There is thus provided in accordance with an exemplary embodiment of the invention a method of implanting an apparatus in a lumen, comprising: dilating an area desired to be treated within said lumen; and, implanting at least the porous structure an enhanced stent apparatus at said area after said dilating. Optionally, the dilating is performed by an angioplasty balloon. In an exemplary embodiment of the invention, the method further comprises providing embolic shower protection during the implanting using the enhanced stent apparatus.

There is thus provided in accordance with an exemplary embodiment of the invention a method of delivering pharmaceutical therapy through a blood brain barrier with an impermeable endothelial cell layer, comprising: imbuing at least the porous structure of the enhanced stent apparatus with at least pharmaceutical; implanting at least the porous structure in proximity to said blood brain barrier; waiting for a new layer of endothelial cells to overgrow at least the porous structure of the enhanced stent apparatus; and, eluting the pharmaceutical after the impermeable endothelial cell layer is reabsorbed. Optionally, at least one pharmaceutical reduces the ability of the blood brain barrier to resist transmission of substances therethough. Optionally, the fiber diameter is minimized and aperture size is maximized in order to improve endothelial cell overgrowth of at least the porous structure.

There is thus provided in accordance with an exemplary embodiment of the invention a method of treating an aneurism in a body lumen, comprising: implanting an embolization coil with the aneurism; and, implanting an enhanced stent apparatus of the claims at a treatment site in the body lumen proximal to the aneurism, such that the embolization coil does not protrude into said lumen. Optionally, the lumen is a cerebral artery.

There is thus provided in accordance with an exemplary embodiment of the invention a method of treating an aneurism in a body lumen, comprising: implanting an enhanced stent apparatus at a treatment site in the body lumen proximal to the aneurism, such that the enhanced stent apparatus restricts flow into the aneurism. Optionally, the lumen is a cerebral artery. Optionally, the method of treating an aneurism is performed in less than an hour and thirty minutes. Optionally, the method of treating an aneurism is performed in less than an hour.

There is thus provided in accordance with an exemplary embodiment of the invention a method of treating vulnerable plaque in a body lumen, comprising: identifying an at risk area within the lumen for vulnerable plaque; implanting at least the porous structure of the enhanced stent apparatus at a treatment site in the body lumen proximal to the vulnerable plaque, such that at least the porous structure of the enhanced stent apparatus traps and holds at least some of the vulnerable plaque between the apparatus and a wall of the lumen.

There is thus provided in accordance with an exemplary embodiment of the invention a method of improving the pharmacokinetics of a luminal stent, comprising: imbuing at least the porous structure of the enhanced stent apparatus with a pharmaceutical; implanting at least the porous structure of the enhanced stent apparatus in a body lumen to be treated, wherein the average distance traveled between the body lumen to be treated and the pharmaceutical is smaller than if only the support element of the enhanced stent apparatus had been implanted.

There is thus provided in accordance with an exemplary embodiment of the invention a method for treatment of small body lumens, comprising: implanting at least the porous structure of the enhanced stent apparatus at a treatment site in the small body lumen, wherein the small body lumen is smaller than 2 mm. Optionally, the implanting is performed by a balloon. Optionally, the treatment is long term. Optionally, long term is on the order of months. Optionally, long term is on the order of weeks.

There is thus provided in accordance with an exemplary embodiment of the invention a method for reducing thrombosis development in a body lumen, comprising: implanting at least the porous structure of the enhanced stent apparatus in the lumen. Optionally, the porous structure is placed over at least a portion of a support element between the support element and an interior of the body lumen. Optionally, the support element is a drug eluting stent. Optionally, the support element is a bare metal stent.

BRIEF DESCRIPTION OF THE DRAWINGS

Exemplary non-limiting embodiments of the invention are described in the following description, read with reference to the figures attached hereto. In the figures, identical and similar structures, elements or parts thereof that appear in more than one figure are generally labeled with the same or similar references in the figures in which they appear. Dimensions of components and features shown in the figures are chosen primarily for convenience and clarity of presentation and are not necessarily to scale. The attached figures are.

DETAILED DESCRIPTION OF EXEMPLARY EMBODIMENTS

The instant application is divided into a number of labeled sections which generally include, in order, descriptions of apparatuses (e.g. porous structures, stents, etc.), materials and methods for manufacturing the apparatuses, the usage of pharmaceuticals with the apparatuses and methods of using the apparatuses. It should be understood that the section headings are for clarity only, and are not intended to limit the subject matter described therein. Furthermore, some of the subject matter described in a particular section may belong in more than one section and therefore, some of the material could overlap between sections.

Overview of Exemplary Enhanced Stent Apparatus

In an exemplary embodiment of the invention, an apparatus is provided which includes a porous structure and, optionally, an underlying support element, such as a stent (wherein underlying means the porous structure is between the support element and a lumen wall).

In some exemplary embodiments of the invention, an enhanced stent apparatus, including the porous structure and a stent, is used to treat stenosis and/or restenosis. In some exemplary embodiments of the invention, the enhanced stent apparatus furnishes at least one of a multiplicity of benefits over a conventional arterial stent. For example, the enhanced stent apparatus is optionally used to prevent plaque from getting into the blood stream to cause embolism, since the porous structure is made with small enough apertures (sizes indicated below) to hold detached plaque in place. In an embodiment of the invention, use of a porous structure replaces the use of an embolism protection device during stent implantation. Optionally, the "umbrella" type embolism protection device is not used. Optionally, the porous structure is used in conjunction with an embolism protection device for enhanced protection over the method of using an embolism protection device during the implantation of a conventional arterial stent. In an embodiment of the invention, the enhanced stent apparatus delivers more comprehensive pharmacological assistance to a treated area than conventional stents. In some embodiments of the invention, the enhanced stent apparatus is optimized to encourage endothelial cell growth and/or migration.

Figure 1:
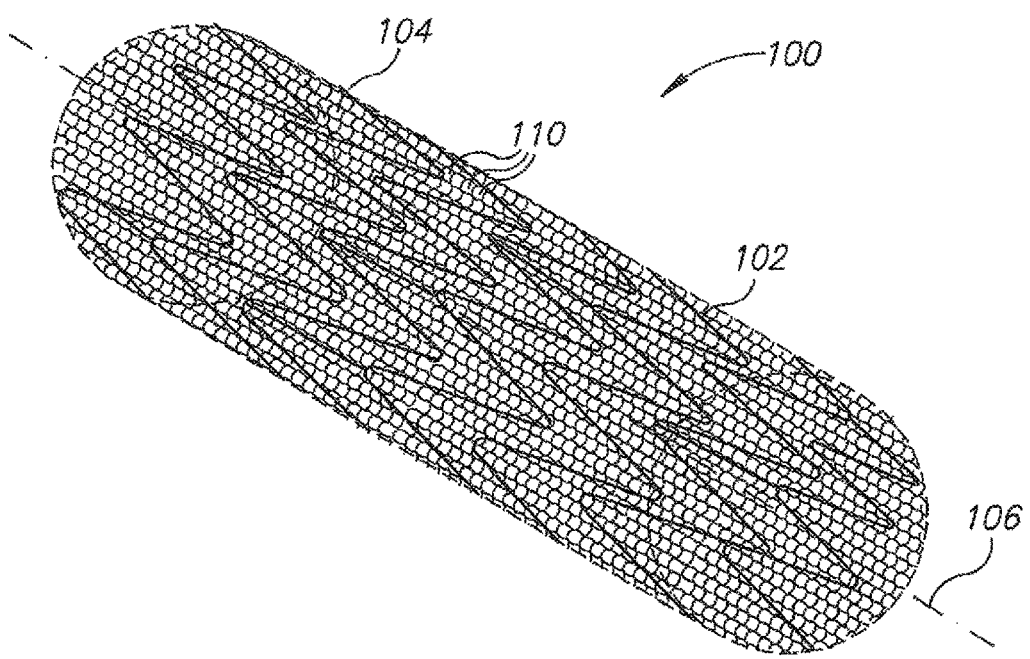
FIG. 1 is a perspective view of an enhanced stent apparatus, in an open, non-crimped mode, in accordance with an exemplary embodiment of the invention.

FIG. 1 shows a perspective view of an enhanced stent apparatus 100, in an exemplary embodiment of the invention. A support element 102 is designed and constructed to expand a blood vessel in a radial fashion from a central axis 106 of the enhanced stent apparatus 100. Optionally, support element 102 is tubular in shape. In some exemplary embodiments of the invention, support element 102 is constructed of a flexible, biocompatible material. Optionally, support element 102 is constructed of stainless steel, nitinol, and/or cobalt chromium and/or other metal alloys (e.g. magnesium alloy). Optionally, support element 102 is constructed of polymer either biostable or bioresorbable. In some exemplary embodiments of the invention, support element 102 is a vascular stent, such as those made by Cordis®, Boston Scientific® and/or Medtronics®, for example.

Figure 2:
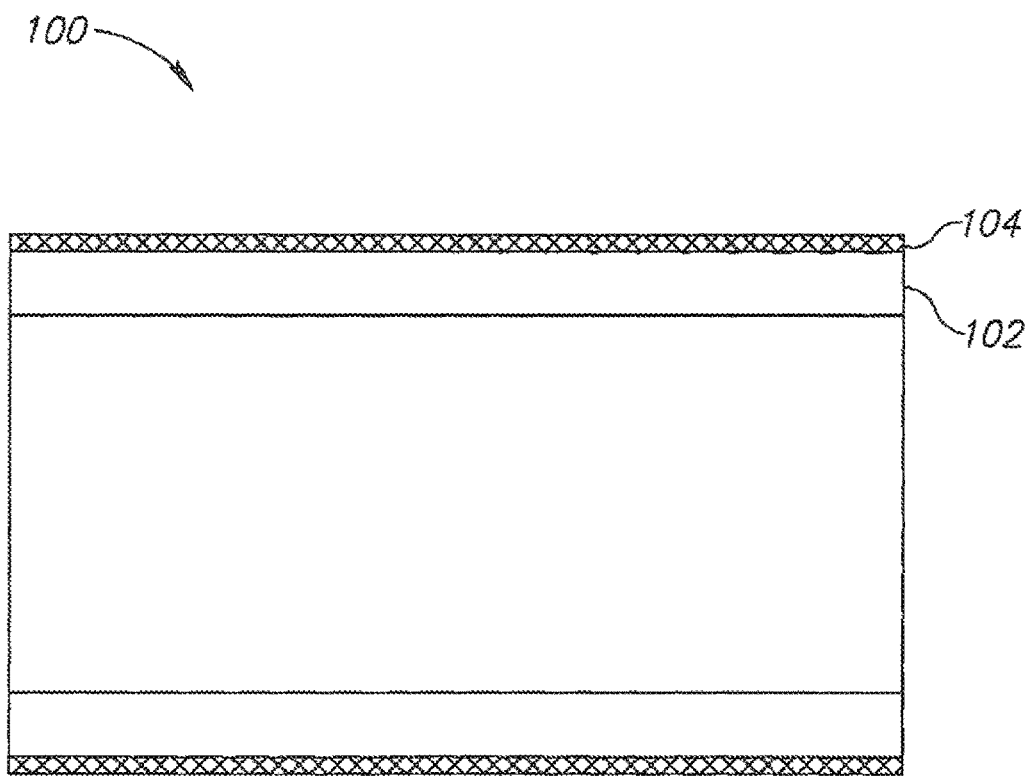
FIG. 2 is a cross-sectional side view of an enhanced stent apparatus, in accordance with an exemplary embodiment of the invention.

In an exemplary embodiment of the invention, support element 102 is covered by at least one porous structure 104. Optionally, support element 102 acts as a support structure for porous structure 104, for example to provide radial support and or to maintain a desired shape of porous structure 104. FIG. 2, shows a cross-sectional view of an enhanced stent apparatus. In this embodiment, support element 102 supplies structural support to porous structure 104, which is located on the exterior of support element 102.

In some exemplary embodiments of the invention, porous structure 104 is laid on the exterior of support element 102 and thereby overlaps gaps in support element 102 (making the aperture sizes of the device as a whole smaller, for example 150 microns), since conventional stent construction usually results in multiple gaps in the structure of the stent, typically several millimeters in other exemplary embodiments of the invention, porous structure 104 covers only a portion of support element 102. For example, only a portion of support element 102 is covered to avoid restricting luminal flow to a branching vessel.

Figure 10:
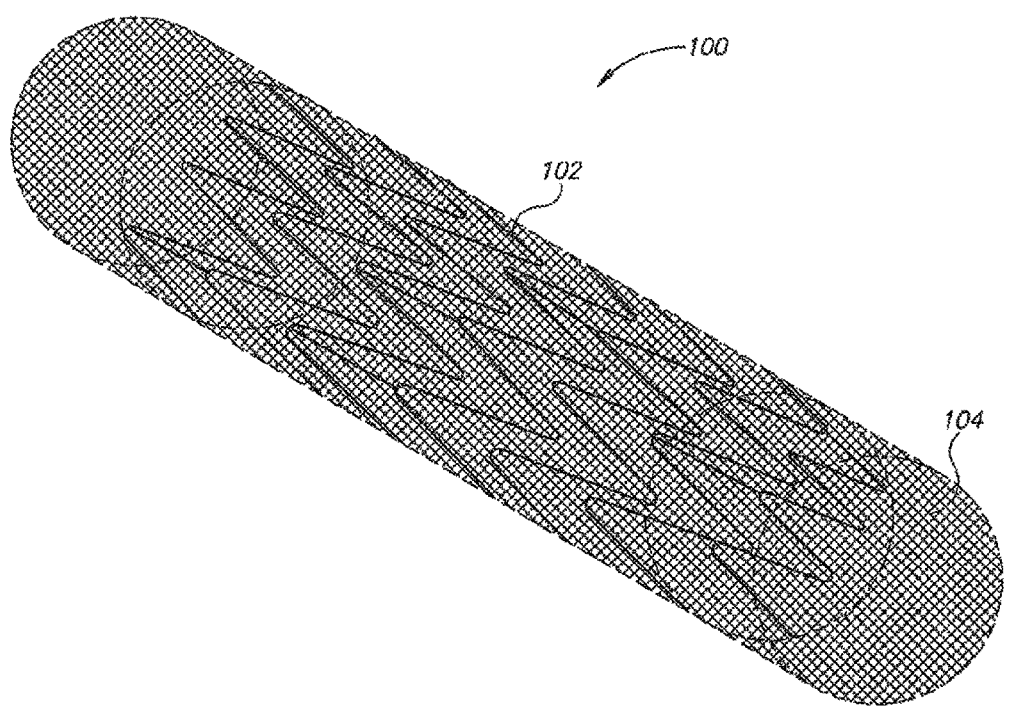
FIG. 10 is a perspective view of an enhanced stent apparatus, wherein porous structure is longer than the support element, in accordance with an exemplary embodiment of the invention.

In some exemplary embodiments of the invention, porous structure 104 extends past at least one end of support element 102. This can, for example, better treat the inside surface of a blood vessel at an edge of enhanced stent apparatus 100, where it is more likely to have restenosis. In an exemplary embodiment of the invention, porous structure 104 pads and/or treats trauma caused by the edge of support element 102 by extending past at least one end of support element 102. Optionally, porous structure 104 extends no more than 1 mm past the end of support element 102. Optionally, porous structure 104 extends over 1 mm past the end of support element 102. Optionally, porous structure 104 extends past only one end or both ends (as shown in FIG. 10) of support element 102.

In some exemplary embodiments of the invention, porous structure 104 is attached to support element 102 to prevent porous structure 104 from unraveling and/or causing tissue irritation and/or avoiding dislodgment of the porous structure from the support element during deployment. Optionally, the end of porous structure 104 is folded over the end of support element 102 and attached, providing padding to a potentially trauma causing edge. Optionally, the end of porous structure 104 is folded under itself and is held folded due to the pressure between the support element and the lumen. In an embodiment of the invention, a treatment, such as heat, is used to make the fold sharp and/or permanent.

It should be understood that while an exemplary configuration of enhanced stent apparatus is shown in FIGS. 1 and 2, other configurations could possibly be used, including: a porous structure 104 over a pharmaceutical eluting support element; a pharmaceutical elating porous structure over a support element 102; a pharmaceutical eluting porous structure over a pharmaceutical eluting support element; a support element in between at least two porous structures, optionally some or all eluting pharmaceuticals; and, an enhanced stent comprised of a plurality of layers which exhibit different optional characteristics such as degradation time and/or pharmaceutical elution. It should be understood that any of the above configurations include biodegradable and/or bioresorbable materials. Optionally, configurations are chosen for specific treatment regimens indicated by the condition of the patient.

In some exemplary embodiments of the invention, porous structure 104 is used to control the local pressure exerted by the enhanced stent apparatus on the body lumen wall. For example, by increasing or decreasing the coverage area of the porous structure as it at least partially covers the stent, the pressure exerted by the enhanced stent apparatus per unit area can be altered. In some embodiments of the invention, modification of the coverage area considers factors such as the stiffness of support element 102 and the geometry and/or coverage area of the support struts of support element 102. In an embodiment of the invention, pressure control is used to reduce the likelihood of the enhanced stent apparatus causing plaque to break off of the lumen wall. In some embodiments of the invention, pressure control is used to reduce tissue trauma typically caused by stent implants, thereby enhancing protection against stenosis/restenosis. Furthermore, in some embodiments of the invention, support element 102 struts which could not be used previously due to the likelihood of trauma to the lumen tissue can optionally be used in combination with porous structure 104.

In some exemplary embodiments of the invention, bile ducts are treated using at least a porous structure as described herein. For example, the bile ducts often become congested with debris (e.g. cholesterol) which restricts flow. Treatment of the bile ducts using enhanced stent apparatus may increase the diameter of the bile ducts, improving their operation.

It is known that varying types of body lumens possess varying surface textures, both varying from each other, and sometimes within one type of lumen. Thus, in some exemplary embodiments of the invention, different porous structures with varying surface texture configurations are manufactured and/or used depending on the interior surface texture of a lumen being treated. For example, peaks and valleys in a body lumen are fitted with counter peaks and valleys of a porous structure (i.e. porous structure counter peak goes into lumen valley and porous structure counter valley accepts lumen peak). Optionally, the counter peaks and valleys are of the same magnitude as the peaks and valleys found in the lumen being treated.

It should be understood that the aperture size, the porous structure thickness, the fiber thickness (or French), and/or the coverage area are varied for different applications. For example when treating the carotids, debris of more than 100 microns should be prevented from reaching the brain, thus the porous structure is designed such that when stent is expanded, usually to about 8 millimeters, the majority of aperture sizes are less than 100 microns. As another example, when treating the coronaries larger debris (>100 microns) is not as problematic, while the endotheliazation process and the non-restriction of flow to side branches is more important. Thus for coronary artery applications, when the support element 102 is in an expanded position, usually about 3 millimeters in diameter, the apertures in the porous structure are optionally larger than 100 microns and below 300 microns. In some embodiments of the invention, the rate of endothelium cell growth over porous structure may be modified by increasing and/or decreasing fiber thickness and porous structure thickness.

Figure 8:
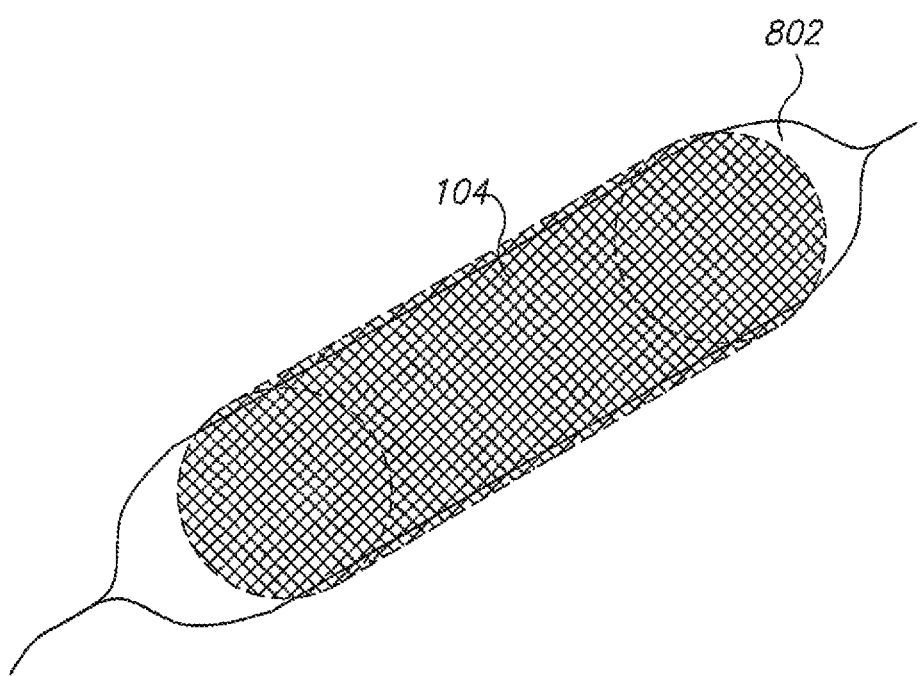
FIG. 8 is a perspective view of an enhanced stent apparatus on an angioplasty balloon, in accordance with an exemplary embodiment of the invention.

In some exemplary embodiments of the invention, porous structure 104 is used with a balloon expandable support element 102. In some exemplary embodiments of the invention, porous structure 104 is placed directly on an expandable balloon 802 without or with support element 102, for example as shown in FIG. 8. In some exemplary embodiments of the invention, the balloon catheter may extend past a proximal and/or distal end of support element 102. It is optionally desirable to provide porous structure 104 which extends past the end of support element 102 to provide a buffer between the balloon add the blood vessel, and optionally to provide pharmaceutical treatment to regions to which the underlying support element 102 does not extend, but may be exposed to the balloon.

In an exemplary embodiment of the invention, porous structure 104 is under 100 microns in thickness. In some exemplary embodiments of the invention, the porous structure is less than 30 microns thick. Optionally, the porous structure is less than 10 microns in thickness. For example, the porous structure is less than 5 microns or 1 micron thick. Porous structure 104 is optionally comprised of at least one fine, thread-like fiber. In some exemplary embodiments of the invention, porous structure 104 is comprised of at least one fiber that is 40 nm to 40 microns thick. Optionally, the fiber thickness is similar to or less than the diameter of an endothelial cell to encourage endothelial cell growth between fibers and/or around at least one fiber. In an exemplary embodiment of the invention, a super-fiber is used to construct porous structure 104, wherein the super-fiber is made of multiple fibers braided together. Optionally, super-fibers are used to enhance the strength of porous structure 104.

In an exemplary embodiment of the invention, the fibers of porous structure 104 are spun and/or knitted and/or woven and/or braided to provide structure to and apertures 110 in porous structure 104. Optionally, the porous structure is woven in an even pattern. Optionally, the porous structure is constructed so that the fibers are randomly positioned in porous structure 104. Optionally, polymer fibers are used to construct porous structure 104. Optionally, polymer coverings are applied to porous structure 102 and/or support element 102. Exemplary porous structure manufacture is described in more detail in the "Methods of Manufacture" section below.

In an exemplary embodiment of the invention, the polymer covered porous structure 104 is optionally made out of a closed interlocked design and/or an open interlocked design, or semi open design, similar to typical support element 102 designs. The open interlocked design has an advantage when side branching is needed. When treating a junction of two blood vessels, there is sometimes a need to introduce one stent through the side of another one. An open interlocked design allows such a procedure, and when the porous structure is made of metal mesh, an open interlocked design is utilized in order to allow easy side branching stents. Optionally, using a biodegradable polymer coating on a non-biodegradable support element 102 leaves the support element 102 embedded alter the biodegradable polymer has degraded.

In an exemplary embodiment of the invention, porous structure 104 is crimped to a small diameter while still maintaining its flexibility, to enable successful maneuverability through a patient's blood vessels to the site where enhanced stent apparatus 100 is to be implanted. In an exemplary embodiment of the invention, porous structure 104 is expandable to enable expansion of porous structure 104 with support element 102 upon deployment at a treatment site within a patient's blood vessel. Optionally, expansion of porous structure 104 along the longitudinal axis matches the expansion of support element 102 along the longitudinal axis.

Figure 9:
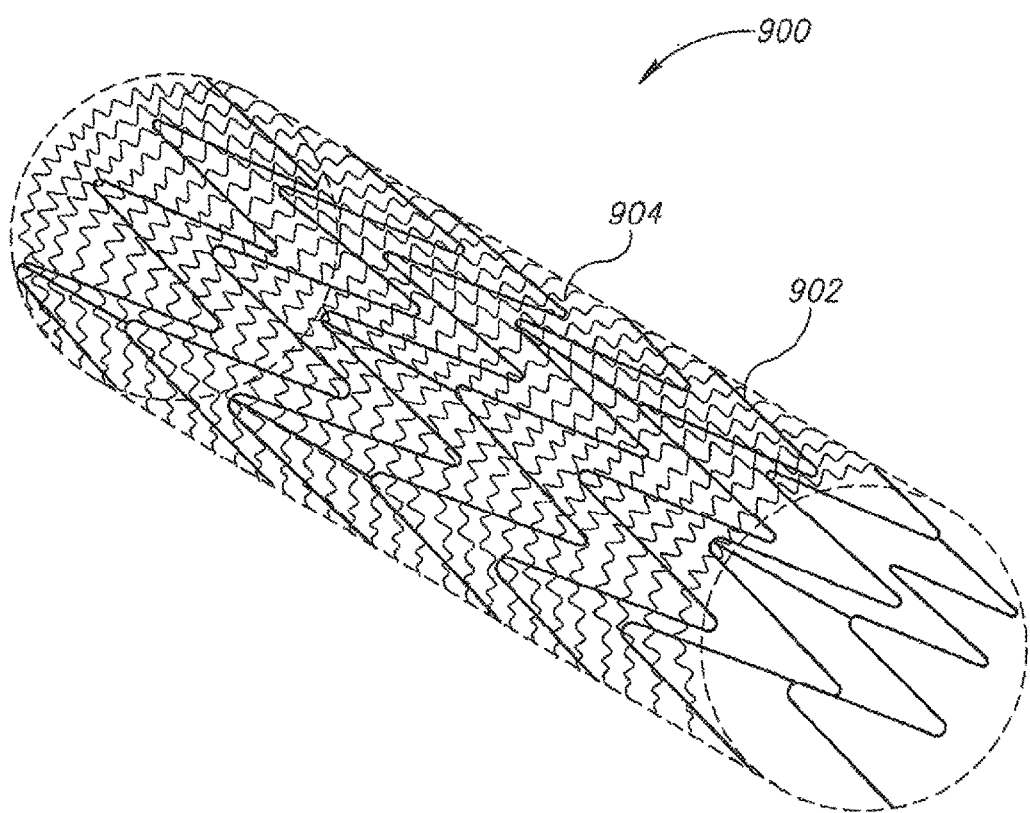
FIG. 9 is a perspective view of an enhanced stent apparatus, provided with longitudinal non-stretchable wires, and horizontal stretchable elastomers in accordance with an exemplary embodiment of the invention.

In an exemplary embodiment of the invention, at least porous structure 104 is expandable without significant foreshortening or elongation of the length of porous structure 104. Optionally, porous structure 104 expands differently than support element 102, for example using sliding connections described herein. As described elsewhere herein, in a knitted embodiment of porous structure 104, expansion occurs at least partially as a result of the knitted structure, and not necessarily because of the elasticity of the fiber used in constructing porous structure 104. In an embodiment of the invention, at least one fiber which comprises porous structure 104 is provided with slack during manufacture to provide additional fiber material when porous structure 104 expands. FIG. 9 shows a perspective view of an enhanced stent apparatus 900. Enhanced stent apparatus 900 is provided with non-stretchable wires 902, and stretchable elastomer fibers 904, in accordance with an exemplary embodiment of the invention. Such an embodiment assists with the preservation of overall apparatus 900 length while allowing expandability and flexibility during implantation.

In an exemplary embodiment of the invention, an enhanced stent apparatus is provided which is comprised of at least an expandable support element and an expandable porous structure. The support element is optionally a stent, examples of which are known in the art for providing treatment to a wide range of body lumens. In an embodiment of the invention, the porous structure has structure which resembles to fishing net. In an embodiment of the invention, the porous structure is knitted from a fiber approximately 15-20 microns in diameter, has a coverage area of less than 20%, and which has aperture sizes approximately 150×200 microns. In some embodiments of the invention, the porous structure is at least temporarily attached to support struts of the support element by stitching. Optionally, the stitches are loose, allowing the porous structure to slide on the support struts, for example to provide extra expandability as described herein with respect to FIG. 16. In some embodiments of the invention, the stitching is biodegradable. In some embodiments of the invention, the support element and/or the porous structure are adapted to elute pharmaceutical agents into the body lumen being treated.

In some embodiments of the invention, different characteristics of the enhanced stent apparatus are chosen based on the intended use or treatment to be rendered. For example, aperture sizes are optionally chosen based on a desire to provide embolic shower protection against debris of a certain size. As another example, coverage area is optionally selected for modifying local pressure on the lumen being treated. Many of these characteristics are interrelated, as described herein and shown in FIG. 15, for example.

In an embodiment of the invention, porous structure 104 is flexible to allow the lumen to naturally change its diameter, to account for pressure changes in the lumen and/or to respond to muscular activity. In some embodiments of the invention, the porous structure 104 divided into a plurality of semi-independent sectors, which react differently to stimuli within or from the lumen. Optionally, the sectors are used to prevent banding of the lumen across the entire length of the porous structure 104.

Exemplary Characteristics and Performance of Porous Structure

Manufacturing techniques, described in more detail below, such as knitting which provide slack to individual fibers, or sections, of porous structure 104, enable porous structure 104 to optionally expand upon deployment up to 10 times its diameter at insertion (insertion diameter is described in more detail below), in an embodiment of the invention. For example, in coronary applications porous structure 104 may expand from 1 mm to 3 mm in diameter. In other examples, porous structure 104 may expand from 2 mm to 8 mm in carotid applications, while in brain applications porous structure 104 may expand from 0.3 mm to 2.5 mm. These numbers are approximate and are by way of example only. In an embodiment of the invention, expansion of porous structure 104 is effectuated in at least one of three ways: 1) the knitted/braided/woven structure of porous structure 104 (including slack in the fibers and curly fibers); 2) the fiber from which the porous structure 104 is made is at least slightly elastic; 3) sliding connections (described below) between porous structure 104 and support element 102 permit shifting of porous structure 104 during expansion with respect to support element 102, within certain limits. In an embodiment of the invention, the fiber from which porous structure 104 is made is comprised of between 2% and 80% of non-elastic materials. In some embodiments of the invention, the elastic material of the fiber from which porous structure 104 is made allows for expansion up to 1000% its original size.

Figure 12:
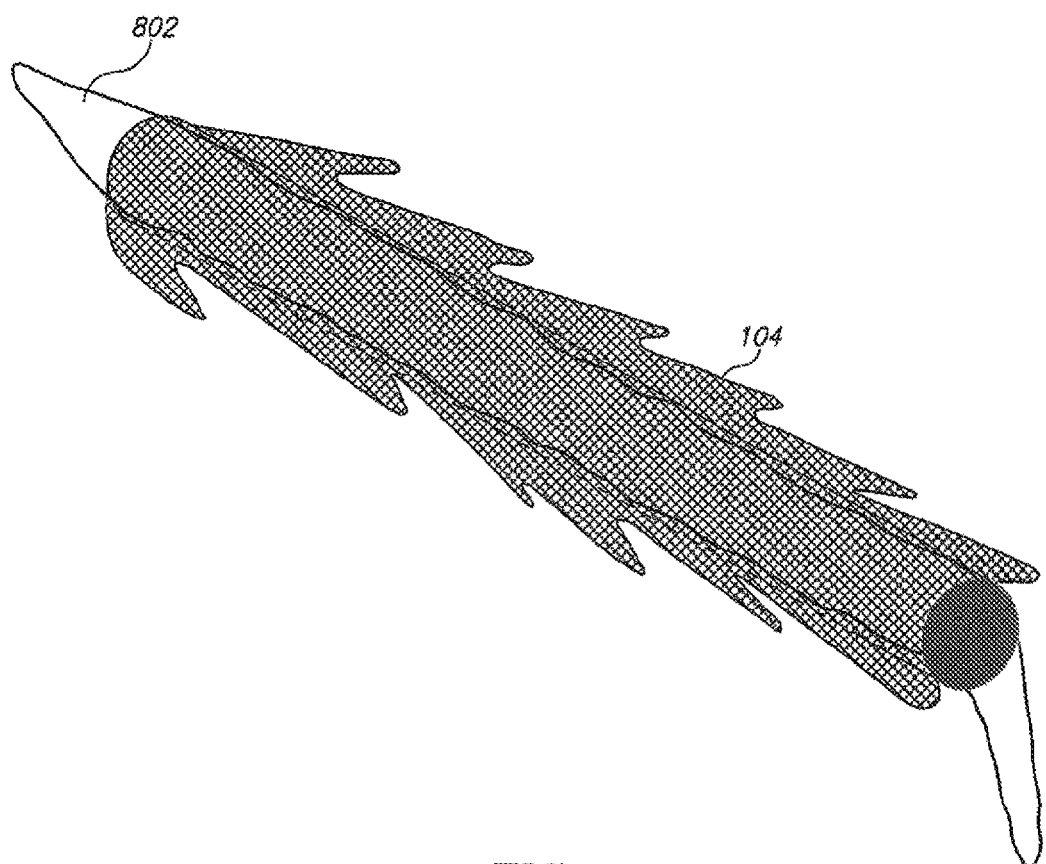
FIG. 12 is a perspective view of a porous structure significantly greater in diameter than an at least partially deflated balloon wherein the porous structure is folded on itself for insertion into a lumen, in accordance with an exemplary embodiment of the invention.

In some exemplary embodiments of the invention, porous structure 104 exhibits a high durability when subjected to twisting, turning, compression and/or elongation, which allows porous structure 104 to withstand the delivery process through the patient's vasculature to a treatment size. In an embodiment of the invention, porous structure 104 is loosely attached to the balloon at several locations and folded for insertion into a lumen, such as depicted in FIG. 12; such a configuration is optionally used in conjunction with supportive element 102. The folded porous structure 104 provides a reduced diameter apparatus for easier insertion into body lumens of the patient. As described below, porous structure 104 is at least temporarily fastened to balloon to prevent porous structure 104 from becoming dislodged during implantation.

In some exemplary embodiments of the invention, 20% of the total area of porous structure 104 is comprised of apertures having an approximate diameter no greater than 50, 200 or more than 200 microns in an expanded configuration. It is recognized that during the course of manufacturing the porous structure, for example with certain manufacturing techniques like electrospinning and/or knitting, apertures created within the porous structure may overlap. This overlap effectively creates an aperture size which is smaller than specified. However, in some exemplary embodiments of the invention, the effective, nominal aperture size is no greater than 50, 200 or more than 200 microns in diameter. In some embodiments of the invention, aperture sizes are selected to encourage endothelial cell overgrowth at a certain rate.

Figure 7:
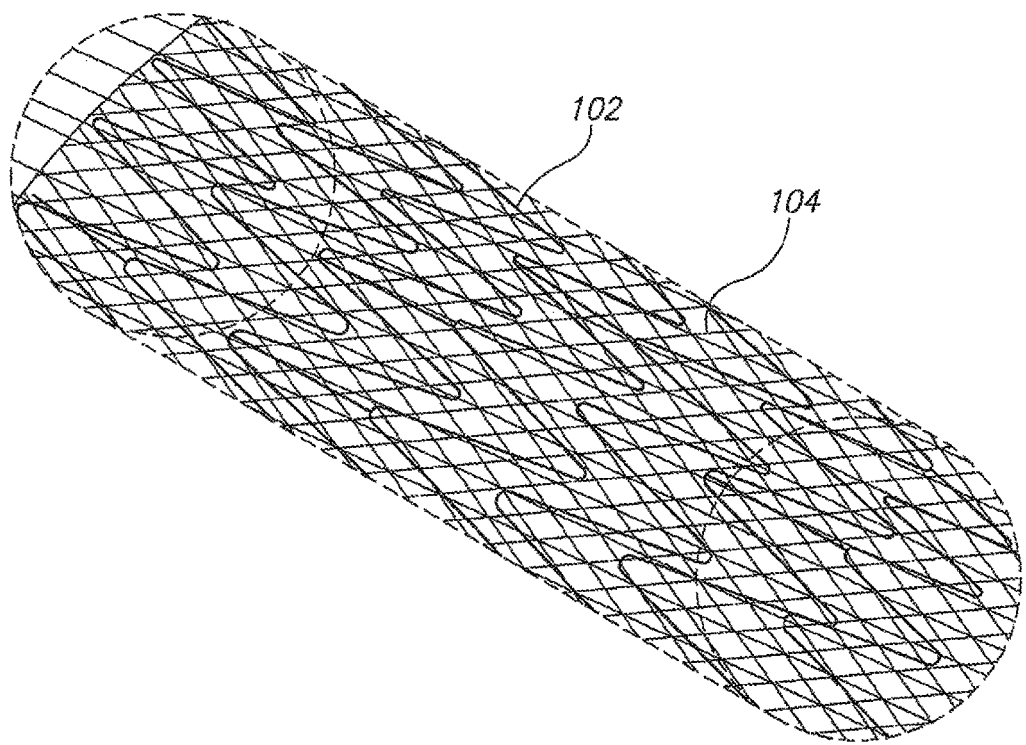
FIG. 7 is a perspective view of a braided porous structure enhanced stent apparatus, in accordance with an exemplary embodiment of the invention.

It should be noted that shapes of apertures are likely to vary at least somewhat as a result of manufacture and/or desired properties of porous structure 104. For example, in a knitted porous structure, apertures are most likely to be roughly square. In contrast, use of a weaving technique to manufacture porous structure likely produce square and/or rectangular shaped apertures whereas a braided porous structure is likely to exhibit quadrilateral shaped apertures, such as in FIG. 7. In describing an approximate "diameter" of an aperture, it should be recognized that all, some or none of the apertures will be actual circles, squares, rectangles and/or quadrilaterals capable of simplistic area measurement using diameter. Therefore, description using diameter is merely an approximation to convey exemplary aperture sizes. For example, "diameter" could be the distance between two parallel sides of a quadrilateral, such as a square or rectangle.

In some parts of the following description, aperture sizes described herein are in reference to their size upon porous structure deployment in a lumen. In other parts, the sizes refer to the aperture sixes when crimped. Sometimes, the aperture sizes described herein refer to their size in a state intermediate a crimped and deployed configuration. In context, it should be easily perceived which of the above configurations applies, however, in the event it is not clear the aperture sizes could be considered as applying to expanded, crimped or intermediate configurations. When a fiber diameter is referred to, it relates to the fiber used to construct the porous structure 104. For example, if porous structure 104 is constructed from a super-fiber comprised of a bundle of 10 fibers each 2 microns in diameter, the overall super-fiber diameter is about 20 microns. Furthermore, it should be understood that references to fiber diameter are for approximation and convenience only and does not imply that the fiber is necessarily round. Optionally, fiber sizes are measured in French sizes, for example 0.003 Fr.

Figure 15:
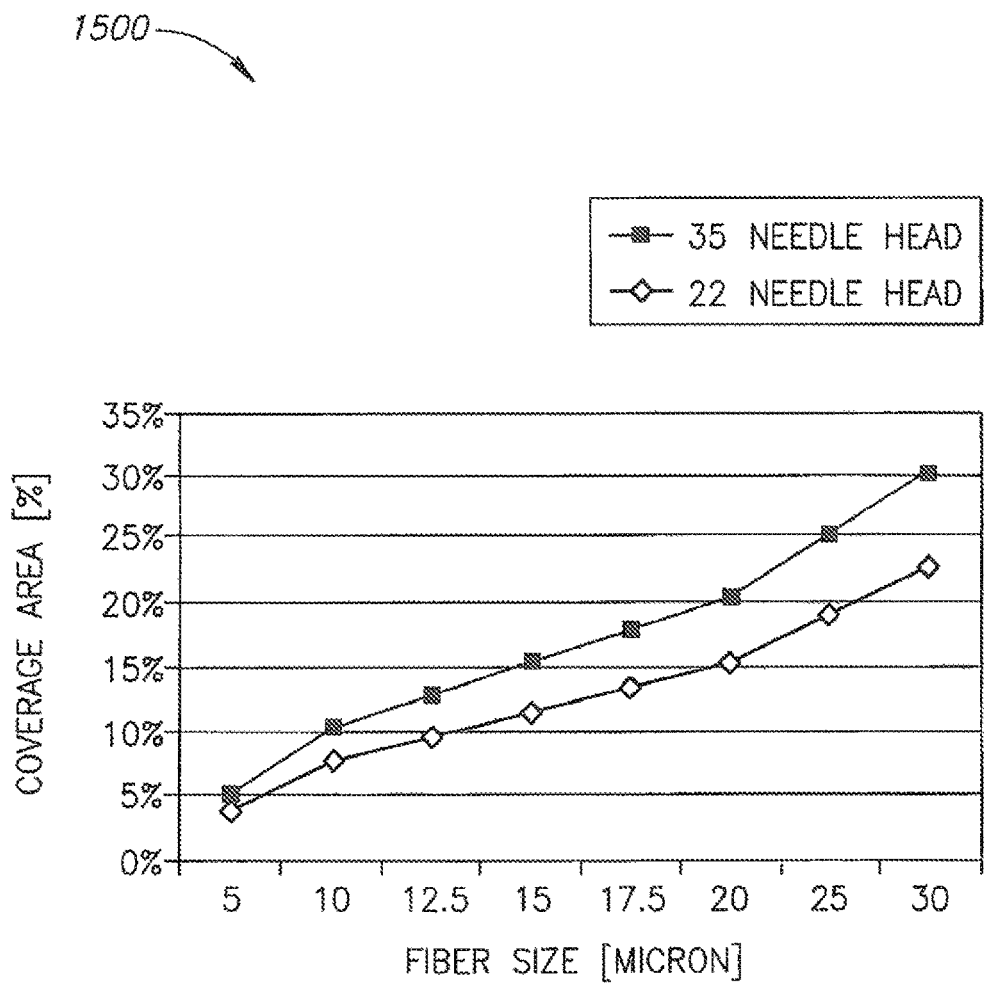
FIG. 15 is a graph showing fiber thickness vs. percentage of porous structure surface area that is structure, in accordance with an exemplary embodiment of the invention.

Referring to FIG. 15, a graph 1500 is shown which correlates fiber thickness of porous structure with percentage of the coverage area of a support element, for a porous structure with a fishing net type configuration. It can be seen that the general trend is that as the fiber sizes get thinner, the amount of porous structure surface area dedicated to structure is reduced. In an embodiment of the invention, it is desirable to have under 25% coverage area. Optionally, porous structure 104 exhibits less than 20% coverage area. In an embodiment of the invention, the coverage area of the porous structure is adapted to be minimized while still performing an intended lumen treating function, such as those described herein. In some embodiments of the invention, the coverage area of porous structure 104 is minimized in order to avoid undesirable clinical side effects. For example, lumen tissue irritation and pyrogenic effects are considerations for minimizing the coverage area and optionally other characteristics such as aperture size, porous structure thickness and/or fiber thickness, of porous structure 104.

Figure 22:
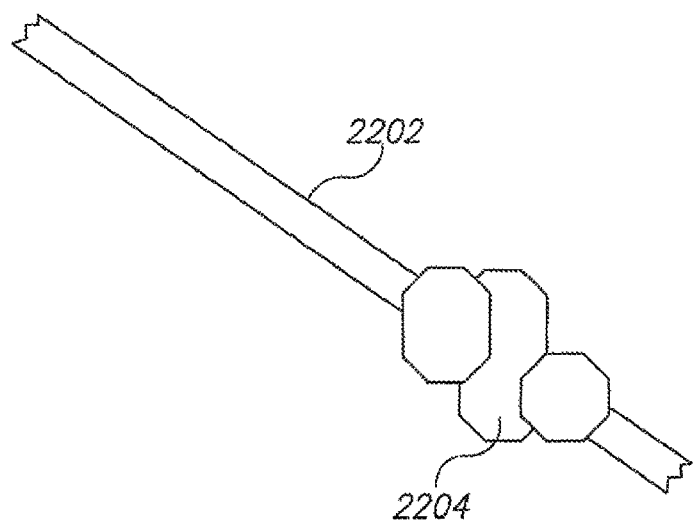
FIG. 22 is cross sectional view of a porous structure with an endothelium cell layer overgrowing it, in accordance with an exemplary embodiment of the invention; and, FIG. 23 is an illustration of a prior art situation in which a clump of endothelial cells detaches from a stent strut.

In some exemplary embodiments of the invention, the proportion of structure to apertures of porous structure 104, fiber size and/or apertures are sized in order to allow easy diffusion through porous structure 104 and to facilitate growth of endothelial cells. Since the fiber 2202 diameters used in construction of porous structure 104 are on the order of the size of the endothelial cells 2204, or smaller, as shown in FIG. 22, the integrity of the cells grown over the porous structure will be much better than what is achieved in the prior art. An individual cell, statistically, will have a firm connection to the blood vessel wall, since it is of the same order or larger than the fiber diameter, thus anchoring itself, in an embodiment of the invention, in more than one location to its native basalamina intimal layer and enabling better growth conditions. It is thus expected that the chance of late or sub-acute thrombosis can be reduced over what is currently achieved when treatment is performed using a pharmaceutical eluting stent. In addition, porous structure 104 effectively acts as an embolic shower protection device, holding detached plaque in place, preventing it from traveling from the vessel wall into the blood stream. It should be noted that porous structure 104 is configured, accounting for fiber thickness, porous structure thickness and/or aperture size such that endothelial cells will overgrow porous structure 104, and optionally support element 102, in order to secure the enhanced stent in place and/or insulate the foreign material of support element 102 and/or porous structure 104 from the bloodstream. In an exemplary embodiment of the invention, endothelial cell layer overgrowth of porous structure 104 is established within hours of implantation. In an embodiment of the invention, overgrowth is accomplished within this time frame due to characteristics of porous structure 104 as they relate to endothelial cells, for example, the overall thickness being on the same order of, or smaller, than an individual endothelial cell. In some embodiments of the invention, it is conceived that a patient's average stay in the hospital after a stenting procedure can be reduced as a result of the speed of endotheliazation using enhanced stent apparatus. In addition, the speed and efficacy of pharmaceutical treatment can expected to be enhanced as a result of the rapid endotheliazation over at least porous structure 104 of enhanced stent apparatus 100.

Figure 23:
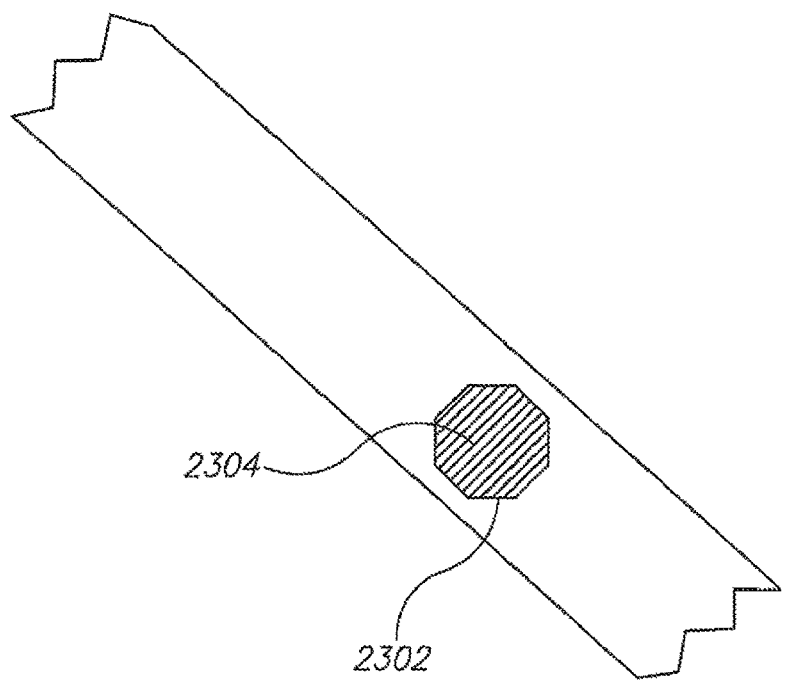

FIG. 23 shows a disadvantage of using prior art drug eluting stents wherein a clump of endothelium cells have become detached from the stent strut 2304, revealing an exposed "island" 2302 of the stent. Sometimes a clump falls off strut 2304 due to poor adhesion of the endothelium cells to the polymer coating of the strut 2304. Contributing to this poor adhesion, the stent strut 2304 is typically an order of magnitude larger than a single endothelium cell, thereby necessitating the creation of a large endothelium cell bridge to cross the strut. The exposed island 2302 can serve as a seed for thrombosis development. In some embodiments of the invention, porous structure 104 is constructed to reduce the likelihood of endothelial cells falling from the porous structure, thereby reducing the chance of development of late or sub-acute thrombosis and exposure of support element 102 to substances within the lumen. For example, endothelial cell retention is optionally encouraged by constructing porous structure 104 from at least one fiber of a thickness and with aperture sizes (to permit growth of endothelial cell therethrough), such as described herein. Optionally, endothelial cells are encouraged to remain on the porous structure by using a fiber layer of a thickness such as those described herein. Optionally, the linear nature of a single fiber porous structure 104, such as shown in FIG. 22, reduces the possibility of a large clump of endothelial cells becoming dislodged. In an embodiment of the invention, porous structure 104, optionally imbued with a pharmaceutical, is placed on the interior of a bare metal or drug eluting support element in order to reduce the thrombogenicity of the support element. For example, by encouraging endothelial cell growth thereover and/or by reducing the exposed surface area of the support element by covering a portion of it up.

As suggested above, using a thin fiber whose thickness is similar to, or smaller than, the diameter of an endothelial cell enables an endothelial cell layer to grow over porous structure 104 while still being closely tied to the basal intima layer at least at two points of the endothelial cell, one point on each side of porous structure 104. In an embodiment of the invention, the anchoring effect of this basal intima layer on the endothelial cell layer reduces the chance of parts of the endothelial cell layer breaking off and entering the lumen. This, in effect, reduces the chances of embolism in the patient and/or also reduces the likelihood of foreign bodies (e.g. the stent and the porous structure) coming into contact and reacting with the contents of the lumen being treated. In the event that a clump of several endothelium cells fall from porous structure 104, exposing a piece of the fiber, it is believed that there is a reduced chance of harm to the patient since the linear, single endothelial cell width geometry is not as thrombogenic as that shown in FIG. 23, where a clump of endothelial cells at least several cells in diameter has fallen off. In addition, the re-endotheliazation will be faster on an exposed porous structure 104 than on the exposed strut 2304 for at least the reason that in the case of the porous structure 104, an endothelial cell layer is formed when just one endothelial cell overgrows the endothelial cell sized fiber used to construct the porous structure. In contrast, endothelial cell layer overgrowth is only accomplished after multiple endothelial cells have covered the exposed island.

In an embodiment of the invention, the reduced risk of late or sub-acute thrombosis by using porous structure 104 for pharmaceutical elution optionally allows for a duration and/or dosage reduction in the use of anti-coagulants by the patient.

In some exemplary embodiments of the invention, fiber thickness, porous structure thickness and/or aperture size are all separately varied depending on the application of porous structure 104 and the needs of the patient. For example, in the coronary arteries it is sometimes helpful to provide for good pharmaceutical dispersion. In such an example, fibers comprising porous structure 104 are optionally located closer together in order to allow for more complete transmission of a pharmaceutical to patient.

In some exemplary embodiments, when large molecule drugs, which have a poor diffusion into the tissue, are used to fight restenosis, the porous structure can be soaked and/or imbued with an appropriate drug in order to better diffuse it. The maximum concentrations of most of the drugs used are rather limited due to side effects and over toxicity, and at the same time the concentration is not enough in order to allow the optimum pharmacokinetics in areas not covered by the stent struts. The porous structure mesh, having a better geometrical cover of the stent area, provides a better and more optimum pharmacokinetics to the whole area covered by the stent. For example, when high Dalton-large molecule drugs are used, or when liposomes are the carriers of the treatment agents, or when the stereo-chemical structure of the drug is large and/or complicated, and/or when the drug is hydrophobic, relatively even distribution of the drug is highly desirable. In some exemplary embodiments of the invention, pharmacokinetics are also optimized because the drug is located on/in the fibers of porous structure 104, and is covered and sealed within an endothelium layer, which helps the drug from being washed away by the blood.

In some exemplary embodiments of the invention, such as in a bypass vein graft, side branching is not an issue, therefore aperture sizes are optionally made smaller, but not so small as to prevent endothelial cell growth therethrough. In another exemplary embodiment of the invention, such as in the carotid arteries, side branching is not generally considered a problem, but catching debris is. Therefore, in some exemplary embodiments of the invention, the aperture sizes of porous structure 104 are decreased to as little as 20 microns in diameter. In other applications, the aperture size can be increased to 50, 100, 200 or even more then 200 microns, depending on the application of enhanced stent apparatus 100.

In some exemplary embodiments of the invention, a plurality of porous structures is used. Optionally, at least one porous structure is located on the interior of support element 102, inside the lumen of support element 102. Optionally, more than one porous structure is located on the exterior surface of support element 102. In some exemplary embodiments of the invention, at least some of the porous structures located on support element 102 are configured to be "in-phase" where the apertures of the porous structures coincide with one another. Optionally, the porous structures are "out-of-phase" where the apertures are configured to not coincide with one another. In an exemplary embodiment of the invention, an "out-of-phase" configuration is used to improve contact surface area between porous structures and the lumen interior surface. In an embodiment of the invention, increased contact surface area can improve pharmacokinetics, reduce local pressure exerted by porous structure 104 on the lumen wall, improve embolic shower protection and/or realize other advantageous effects. In some exemplary embodiments of the invention, porous structure 104 is constructed in the same shape and pattern as support element 102, but on a smaller scale.

Exemplary Materials of Manufacture

It should be noted that in some exemplary embodiments of the invention, a stretchable and/or expandable porous structure 104 is desired. Therefore, in some embodiments of the invention, materials are chosen which are either a) stretchable and/or b) can be used to manufacture a porous structure which is stretchable (e.g. a knitted structure). In some exemplary embodiments of the invention, biodegradable (i.e. are broken down by the body) and/or bioresorbable (i.e. are absorbed into the body) materials are used. In addition, blends of materials are used in accordance with some embodiments of the invention. In an embodiment of the invention, a material is chosen because it exhibits durability during manufacture, deployment and/or use despite being thin. In an embodiment of the invention, other considerations for the material to be used are their biocompatibility, toxicity, hemocompatibility, and thrombogenicity.

Exemplary materials for manufacturing porous structure 104 include natural-based materials such as modified cellulose and/or collagen. In some embodiments of the invention, metal fibers are used to construct porous structure, optionally constructed of stainless steel, and/or CoCr and/or CoNi alloy among other possibilities. Optionally, the metal fibers used are coated with at least one polymer. In some embodiments of the invention, porous structure is manufactured from a shape memory alloy, such as nitinol. Optionally, carbon fiber is added to porous structure 104 in order to improve strength characteristics of porous structure 104. Optionally, glass fiber is added to porous structure 104 in order to improve strength characteristics of porous structure 104. Optionally, a durable, resorbable and/or degradable fiber is added to porous structure 104 in order to improve strength and durability characteristics of the fiber during manufacture, which is degraded or resorbed or washed away to leave a thinner porous structure 104.

In an embodiment of the invention, some polymer fibers are chosen for use in constructing porous structure 104 because they are elastic, biocompatible, hemocompatible, can be made not to stick to an expandable angioplasty-type balloon catheter, to stick to endothelium tissue, are selectably bio-stable and/or biodegradable, exhibit the requisite mechanical strength, are sterilizable, have a high temperature transformation zone (solid and non-sticky at 37° C.), are capable of hosting an effective amount of pharmaceuticals, and/or can release embedded pharmaceuticals at a controlled rate. In some exemplary embodiments of the invention, other materials which exhibit some or all of these properties are optionally used to construct porous structure 104. Optionally, coatings are put on porous structure 104, comprised of materials which exhibit some or all of these properties.

Polymer fibers are optionally made out of any of the following materials: thermoplastic polymers for example polyethylene terephthalate (PET), polyolefin, oxidized acrylic, PTFE, polyethylene co-vinyl acetate, polyethylene elastomer, PEO-PBT, PEO-PLA, PBMA, polyurethane, Carbosil (PTG product), medical grade polycarbonate urethanes, Nylon, PEEK-Optima, carboxylic acid moiety comprising one or more of a poly acrylic acid, a poly methacrylic acid, a maleic acid, a helonic acid, a taconic acid and/or combinations and/or esters of these monomers, thermoplastic polymers, thermosetic polymers, polyolefin elastomers, polyesters, polyurethanes, polyfluoropolymers, and/or nylon. Optionally, the fibers are constructed of an elastomer. Optionally, the fibers are constructed of a coated fiber with a drug and polymer coating mixed to get a predetermined drug release characteristic, either coating over a metal and/or over a polymer fiber. Optionally, the fibers are constructed of other materials than the exemplary materials listed above. Exemplary polymers which are optionally used for this purpose are manufactured by Cordis®, Surmodix®, Boston Scientific®, Abbott® and Hemoteq® Polymers. Optionally, these polymers are selected for at least one of the reasons specified in the paragraph above. Optionally, the coating is used to facilitate the elution of pharmaceuticals from porous structure 104.

In some embodiments of the invention, the porous structure is made out of a resorbable/degradable polymer such as poly lactic-co-polyglycolic ("PLGA") copolymers, or any other degradable copolymeric combination, such as polycaprolactone ("PCL"), polygluconate, polylactic acid-polyethylene oxide copolymers, poly(hydroxybutyrate), polyanhydride, poly-phosphoester, poly(amino acids), poly-L-lactide, poly-D-lactide, polyglycolide, poly(alpha-hydroxy acid) and combinations thereof.

In some embodiments of the invention, porous structure 104 is comprised of a material which plastically or elastically deforms when a sufficient amount of radial pressure is applied to it, for example by an angioplasty balloon.

Exemplary Methods of Manufacture

Many of the methods and orientations described herein are designed to provide a porous structure which exhibits at least some expandable quality. Porous structure 104 is optionally adapted and constructed to stretch as it is being deployed within the lumen being treated. In some exemplary embodiments of the invention, porous structure 104 is provided with stretchability in order to ease positioning porous structure 104 on a balloon and/or support element 102.

In an exemplary embodiment of the invention, weaving, braiding and/or knitting results in some or all the elasticity of the porous structure being achieved due to the structure of the interlaced and/or crimped and/or textured fibers (curly, slack). This can be achieved by material elongation properties securing the porous structure to the stent. In some exemplary embodiments of the invention, a porous structure is made by combining several interlacing techniques such as knitting over a braided porous structure or braiding over a knitted porous structure. In some embodiments of the invention, multiple layers are combined and/or created using these techniques. In some exemplary embodiments of the invention, a warp knitted porous structure with "laid in" yarns is used. In some exemplary embodiments of the invention, a porous structure is woven using elastomeric or crimped weft to obtain radial elasticity.

In some exemplary embodiments of the invention, the porous structure is manufactured by combining several techniques such as knitting over a braided porous structure or braiding over a knitted porous structure. In some exemplary embodiments of the invention, a weft knitted porous structure with "laid in" yarns is used. In some exemplary embodiments of the invention, a porous structure is woven using elastomeric and/or crimped weft to obtain radial elasticity. Optionally, porous structure is comprised of at least one fiber oriented generally parallel to the support element's longitudinal axis.

In an exemplary embodiment of the invention, a manufactured porous structure is added as a cover to support element 102. Optionally, porous structure 104 is used separately from support element 102, which is optionally not used for stenting. In some exemplary embodiments of the invention, porous structure 104 is manufactured directly onto support element 102.

In an exemplary embodiment of the invention, porous structure 104 is manufactured by a knitting technique known to those skilled in the knitting art for non-analogous arts, such as clothing manufacturing and textiles. Knitting of porous structure 104 is optionally performed by heads having between 20 and 35 needles. Optionally, the head used has between 30 and 45 needles. Optionally, the head used has between 35 and 80 needles. An example of the effect of head size on the porous structure can be seen in FIG. 15, described above, in which a 22 size head and a 35 size head are graphed. In FIG. 15, the needle gauges are 40.

In some embodiments of the invention, the shape and/or size of the knit is controlled by controlling the tension on the fiber being used for knitting. For example to create a knit with larger eyes, slack is provided to the fiber during knitting. Optionally, the fiber is controlled during knitting to achieve a circular shaped eye when porous structure 104 is expanded. In an embodiment of the invention, pre-tension on the fiber during knitting is approximately 10-20 grams. In some embodiments of the invention, post-tension on the fiber during knitting is 15-25 grams. The stitch length is between 300 and 400 microns, in an exemplary embodiment of the invention. In some embodiments of the invention, the knitting machine is run at a relatively slow speed. For example, the knitting machine is run at 10% of speed capacity using a Lamb Knitting Machine Corp. System Model WK6 with a special modification of speed operation measured by percentage.

In an exemplary embodiment of the invention, a fiber or a super-fiber yarn with a specific fineness, or a range of fineness, between 5 and 100 microns is used to manufacture a knit porous structure. Optionally, yarn with a fineness of 10 to 20 microns is used to manufacture a knit porous structure. Optionally, the yarn is finer than 5 microns. Yarn fineness is often referred to in textile terms by "Tex". This is the weight in grams of 1000 meters of the yarn. In an exemplary embodiment of the invention, yarn ranging from 0.3 Tex to 10 Tex is used to manufacture porous structure. In some embodiments of the invention, a specific yarn fineness is chosen based on the desired porous structure 104 characteristics. For example, a 0.5 Tex yarn using a 22 gauge needle head will, in some embodiments, produce a porous structure with approximately 12% coverage area.

Figure 5:
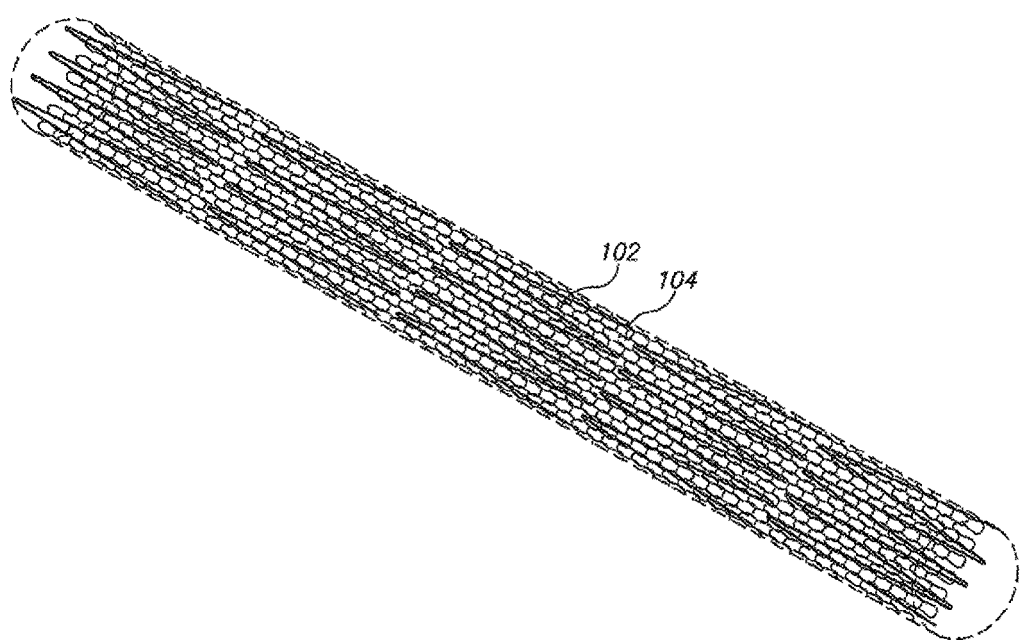
FIG. 5 is a perspective view of an enhanced stent apparatus, in a crimped, closed mode, in accordance with an exemplary embodiment of the invention.
Figure 6A:
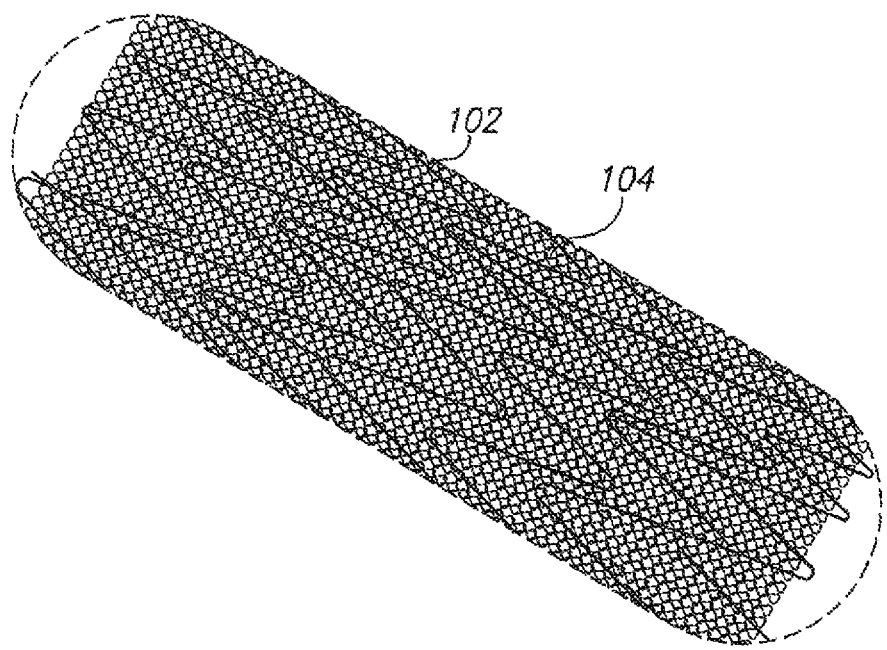
FIG. 6A is a perspective view of a knitted porous structure enhanced stent apparatus in an open mode, in accordance with an exemplary embodiment of the invention.
Figure 6B:
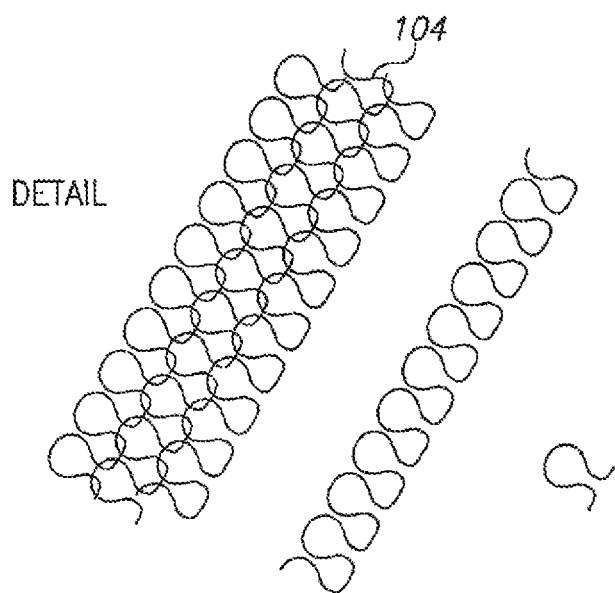
FIG. 6B is a detailed view of a knitted porous structure, in accordance with an exemplary embodiment of the invention.

An exemplary resulting porous structure using the above components and techniques, should have 5 to 50 courses per cm. Optionally, 20 to 45 courses per cm are manufactured. Optionally, a porous structure with 30-35 courses per cm is manufactured. FIG. 5 illustrates a knitted porous structure 104 and support element 102 in a crimped, closed position. FIG. 6A illustrates a knitted porous structure 104 laid on top of a support element 102 in an open position. FIG. 6B shows exemplary knitting in detail.

In another exemplary embodiment of the invention, weaving techniques are used to manufacture porous structure 104. Narrow needle looms as well as conventional narrow looms can be configured to produce woven tubular structures. In weaving, at least two layers of warp yarns are interlaced with intersecting fill yarns. By carrying the fill yarn alternately back and forth across two layers of warp yarns, a tubular shape is created. The size and shape of the weave are optionally controlled by determining the warp and/or fill density, the interlacing pattern and/or frequency, the yarn tension and/or the yarn dimensions and/or elastic properties. The types of weaves used for a porous structure are optionally one of "plain", "basket", "twill", "sateen", "leno" and/or "jacquard". Optionally, all of the fibers of porous structure are the same. Alternatively, warp and weft fibers of a weave are not constructed of the same materials. Optionally, different materials are used to take advantage of the inherent properties of the different materials, for example one material may be elastic and a different material may have a high tensile strength. Optionally, warp fibers are coated and/or are pharmaceutical eluting while the weft fibers are not, or vice versa.

In another exemplary embodiment of the invention, braiding techniques are used to manufacture porous structure 104, for example as described in Knitting Technology, D. J. Spencer—ed., Woodhead Publishing Limited, Abington Hall, Abington, Cambridge, CB1 6AH, England, the disclosure of which is incorporated herein by reference. Braiding machines are optionally used to interlace yarns at a variety of intersecting angles. In braiding, multiple yarns are fed to an interlacing zone. Interlacing is optionally achieved by rotation of the yarn spools or by a reciprocating needle bed. The size and shape of the braid is optionally controlled by the number of yarns, the interlacing pattern and/or angle and/or the yarn dimensions and/or elastic properties. Optionally, all of the fibers of porous structure are the same. Optionally, warp and weft fibers of a braid are not constructed of the same materials, for example where weft fibers are used to provide strength and warp fibers are used to provide stretchability of the braid.

In another exemplary embodiment of the invention, porous structure 104 is manufactured by an electrospinning process. Electrospinning is a technique which utilizes a charged polymer solution (or melt) that is fed through a small opening or nozzle (usually a needle or pipette tip).

Figure 4:
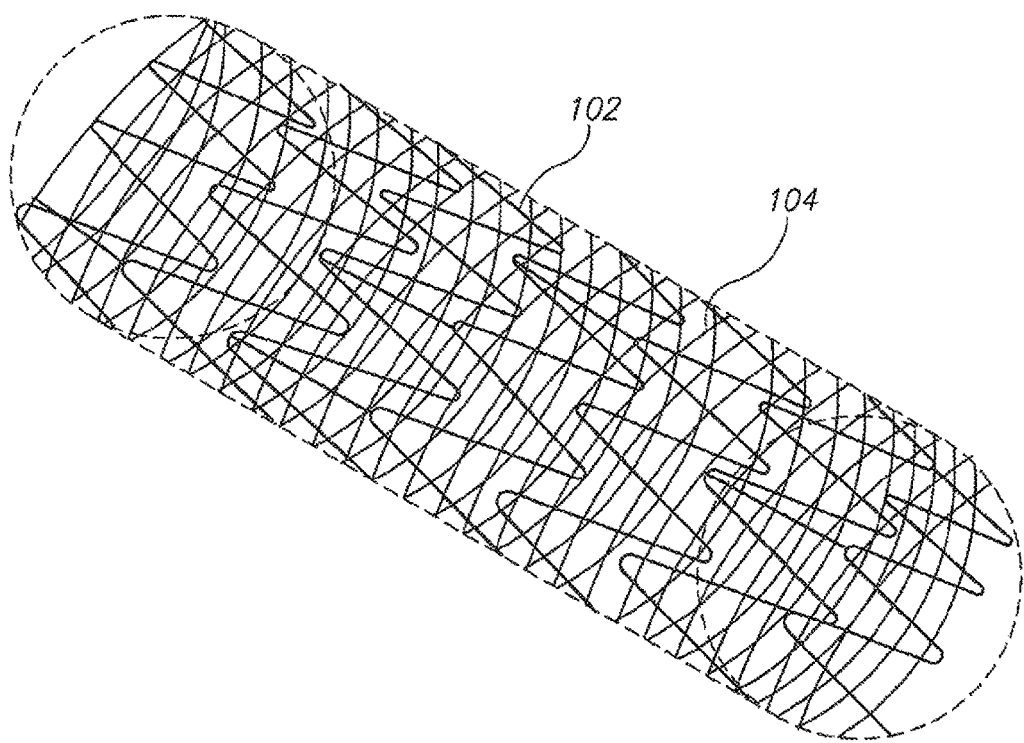
FIG. 4 is a perspective view of an enhanced stent apparatus, with multiple helical coils in an open mode, in accordance with an exemplary embodiment of the invention.

Because of its charge, the solution is drawn toward a grounded collecting plate (usually a metal screen, plate, or rotating mandrel), typically 5-30 cm away, as a jet. Optionally, support element 102 is placed on a delivery catheter which is used as a mandrel. During the jet's travel, the solvent gradually evaporates, and a charged polymer fiber is left to accumulate on the grounded target. The charge on the fibers eventually dissipates into the surrounding environment. The resulting product is a non-woven fiber porous structure that is composed of tiny fibers with diameters between approximately 40 nanometers and 40 microns (e.g. a felt), depending on the size of the fibers input into the system. If the target is allowed to move with respect to the nozzle position, such as by rotating and/or moving the mandrel along its longer axis, specific fiber orientations (parallel alignment or a random alignment, as examples) can be achieved. In some exemplary embodiments of the invention, porous structure 104 is spun in a helical coil pattern onto the mandrel or support element 102. Optionally, porous structure 104 is comprised of a plurality of helical coil patterns, constructed by moving the mandrel back and forth, such as depicted in FIG. 4. Optionally, porous structure 104 is constructed with fibers oriented substantially parallel to central axis 106. Optionally, porous structure 104 is constructed with fibers oriented substantially perpendicular to central axis 106. Optionally, porous structure 104 is constructed with fibers oriented in a combination of any of the orientations described or suggested herein. The mechanical properties of the porous structure are optionally altered by varying the fiber diameter and orientation depending on the requirements for treating a patient. For example, in some embodiments of the invention, a laser is used to cut specific aperture sizes and/or to ensure that the apertures traverse from the exterior side of porous structure 104 to the interior side of porous structure 104. Optionally, solvent is used to modify aperture sizes.

Optionally, portions of catheter are masked in order to prevent accidental coverage of the delivery catheter by porous structure 104. Optionally, support element 102 is coated with an adhesive and/or a pharmaceutical agent prior to putting the porous structure 104 on the top of support element 102. In some exemplary embodiments of the invention, the material used to produce the porous structure 104 is imbued with pharmaceutical agents. Optionally, pharmaceutical agents are embedded in the material coating the porous structure 104. In an exemplary embodiment of the invention, porous structure 104 is comprised of at least one inner coating proximal to supporting structure 102 which exhibits different properties than an external coating proximal to patient's blood vessel. For example, the inner coating is optionally configured to avoid adhesion to the delivery catheter and/or support structure. Optionally, inner coating is configured to adhere to support element 102, but not to delivery catheter.

In some embodiments of the invention, porous structure 104 is designed to be less sensitive to foreshortening and elongation forces as porous structure 104 expands upon deployment. This is in part due to the knitted nature of porous structure 104, in some embodiments. This property allows porous structure 104 to be secured to support element 102 at its ends, rather than in another location, such as the middle as described in U.S. App. No. 2005/0038503 to Greenhalgh et al., the description of which is herein incorporated by reference.

In some exemplary embodiments of the invention, a porous structure is manufactured in an at least partially open, wide diameter, condition. In some exemplary embodiments of the invention, the at least partially stretched porous structure is reduced to a smaller diameter, by heat-setting, crimping and/or folding, after manufacture.

Figure 13:
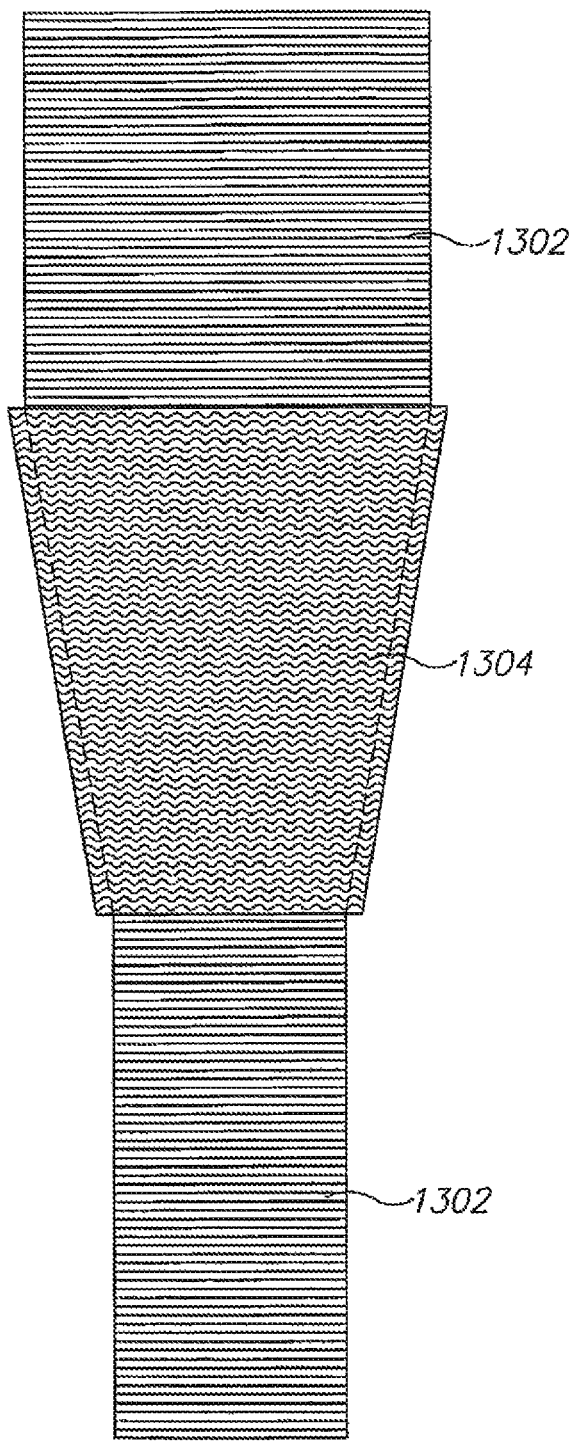
FIG. 13 illustrates the use of a funnel to reduce the diameter of at least a porous structure, in accordance with an exemplary embodiment of the invention.
Figure 14:
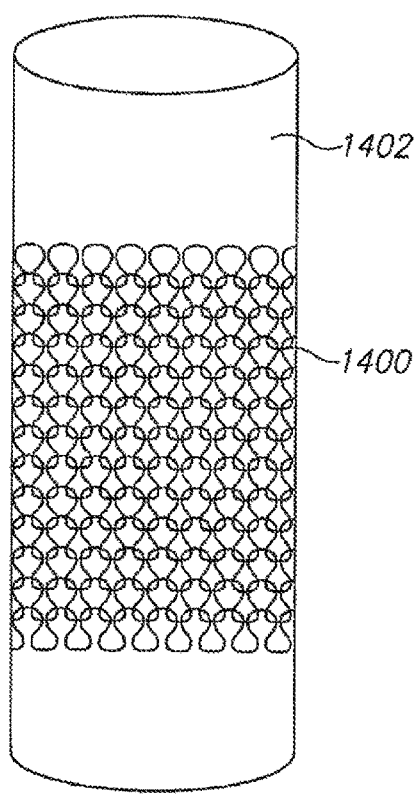
FIG. 14 illustrates using a stretchable rubber tube for manufacturing a compressed porous structure, in accordance with an exemplary embodiment of the invention.
Figure 14:
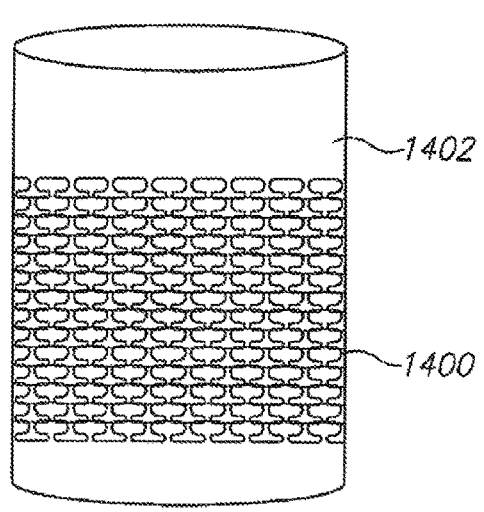

In an embodiment of the invention, the diameter of the at least partially stretched porous structure is reduced mechanically. Optionally, a funnel 1304 shown in FIG. 13, is used to reduce the diameter of the knitted porous structure 1302, during the manufacture the porous structure. A knitted porous structure 1302 is drawn down from the knitting zone into a narrowing bore, funnel 1304. This results in a final porous structure diameter that is controllably smaller than the diameter of the needle bed. FIG. 14, illustrates how a porous structure is manufactured using a stretched rubber tube 1402. In this method, the porous structure 1400 is tightly inserted onto a pre-radially stretched tube 1402, and then the tube is relaxed, compressing the porous structure and creating a smaller aperture sized porous structure, the size of which is controlled by the stretch ratio of the rubber tube.

Figure 11:
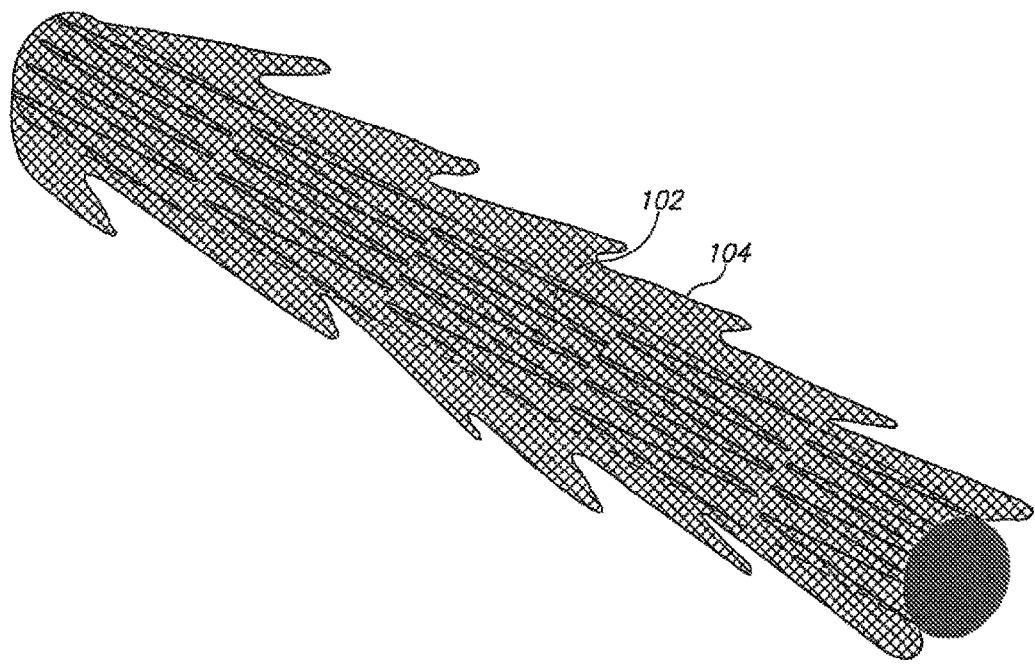
FIG. 11 is a perspective view of an enhanced stent apparatus, wherein porous structure is significantly greater in diameter than a crimped support element, and is folded on itself for insertion into a lumen, in accordance with an exemplary embodiment of the invention.
Figure 18:
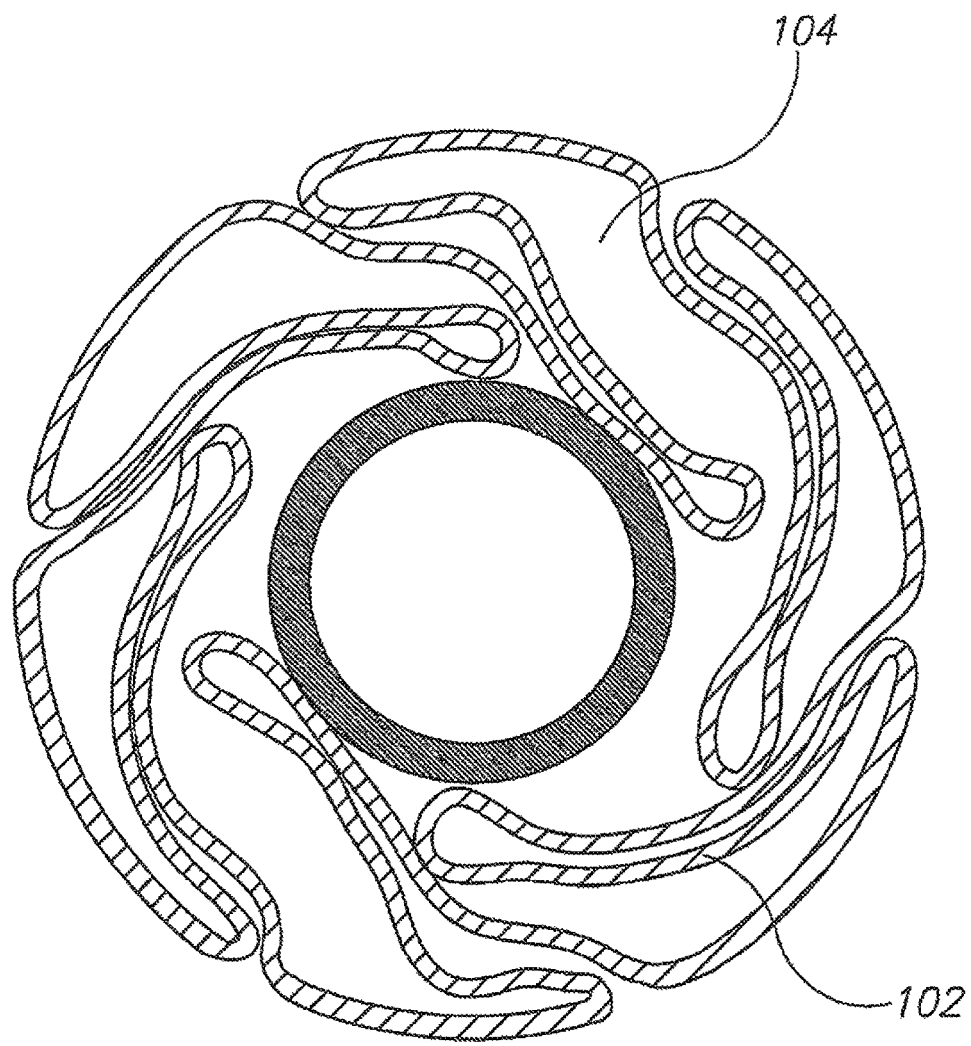
FIG. 18 is a cross-section view of an enhanced stent apparatus showing a porous structure folding technique, in accordance with an exemplary embodiment of the invention.

Referring to FIG. 18, an embodiment is shown in which porous structure 104 is folded in "n" substantially folds, the folds used to reduce the overall diameter of enhanced stent apparatus 100 for easier insertion and navigation through the patient. Optionally, the folds are towards the same direction. In an embodiment of the invention, a folded porous structure 104 is at least temporarily secured to support element 102. FIG. 11 shows an alternate folded configuration from a perspective view.

An additional or alternative embodiment to folding includes heat setting a polymer comprised porous structure 104 to support structure 102. In an embodiment of the invention, heat setting is used when porous structure 104 is comprised of at least one polymer material. Determination of heat setting conditions is related to the polymer's heat transition temperatures, in an embodiment of the invention. Heat setting is performed in the temperature range between $T_g$ and $T_m$ of the polymer. At this range the polymer becomes amorphous and is shrunk to support element 102, establishing an overall enhanced stent apparatus 100 radius that is not much more than the support element 102 radius. For example, porous structure 104 adds less than 10 microns in diameter total to support element 102 which is 1 mm in diameter, in some embodiments of the invention. At $T_m$ the polymer turns into a viscous liquid which loses its mechanical integrity and will stick to support element 102 surface. For example, polyethyleneterephthalate (PET) has a $T_g$ of 70° C. and a $T_m$ of 265° C., therefore the heat set temperature somewhere within that range, in an embodiment of the invention, is 200° C. Using temperatures higher than $T_m$ for heat setting can cause thermal degradation, which results in polymeric chain scission, unzipping of the polymer and/or producing a large array of oligomeric material that changes the mechanical properties of porous structure 104 and/or releases poisonous and/or non-biocompatible materials, causing an inflammatory reaction in the patient. Other exemplary polymers which can be used in heat setting are below in Table 1 (not an exhaustive list):

TABLE 1

Exemplary polymers and temperatures for heat setting

| Material name | $T_g$ | $T_m$ | set temp |
|---|---|---|---|
| PP | −18° C. | 165° C. | 140° C. |
| NYLON 6,6 | 80° C. | 265° C. | 210° C. |
| PTFE | 150° C. | 330° C. | 300° C. |

TABLE 1-continued

Exemplary polymers and temperatures for heat setting

| Material name | $T_g$ | $T_m$ | set temp |
|---|---|---|---|
| PVA | 100° C. | 230° C. | 190° C. |
| Polyurethanes | 70° C. | 120° C. | 100° C. |
| PLLA | 60° C. | 175° C. | 100° C. |

Another additional or alternative embodiment to folding includes crimping using at least a crimped support element 102 in combination with porous structure 104. In some embodiments of the invention, porous structure 104 is crimped with support element 102. In an embodiment of the invention, crimping of porous structure 104 and support element 102 is performed when it is desirable to reduce the overall diameter of enhanced stent apparatus 100. For example, a reduced diameter enhanced stent apparatus 100 allows for easier insertion and navigation of the apparatus to the treatment site. In some embodiments of the invention, at least a crimped support element 102 provides an object with relatively stable mechanical properties for more predictable movement during insertion and navigation.

Optionally, porous structure 104 is made on a non-crimped support element 102. A non-crimped support element 102 can be expanded or semi-expanded during manufacture. In an exemplary embodiment of the invention, porous structure 104 and support element 102 are crimped together. Optionally, excess porous structure 104 material, which is created as a result of reducing the profile of support element 102 during crimping, is folded with support element 102, such as shown in FIG. 18. In some exemplary embodiments of the invention, porous structure 104 is made on a crimped or partially crimped support structure 102. When manufacturing a porous structure for placement on an already crimped support structure, consideration may be given to providing a porous structure which is sufficiently stretchable to expand with the radial expansion of the support structure, when implanted at a treatment site within a lumen. In some embodiments of the invention, a porous structure is placed on a support element already positioned on an angioplasty balloon.

In electrospinning embodiments of the invention, the procedure for manufacturing a porous structure on a balloon is similar to manufacturing on a stent or mandrel. For example, varying the motion of the balloon with respect to the electrospinning device allows the manufacture of specific fiber orientations.

Exemplary Methods for Coating a Fiber

Figure 19:
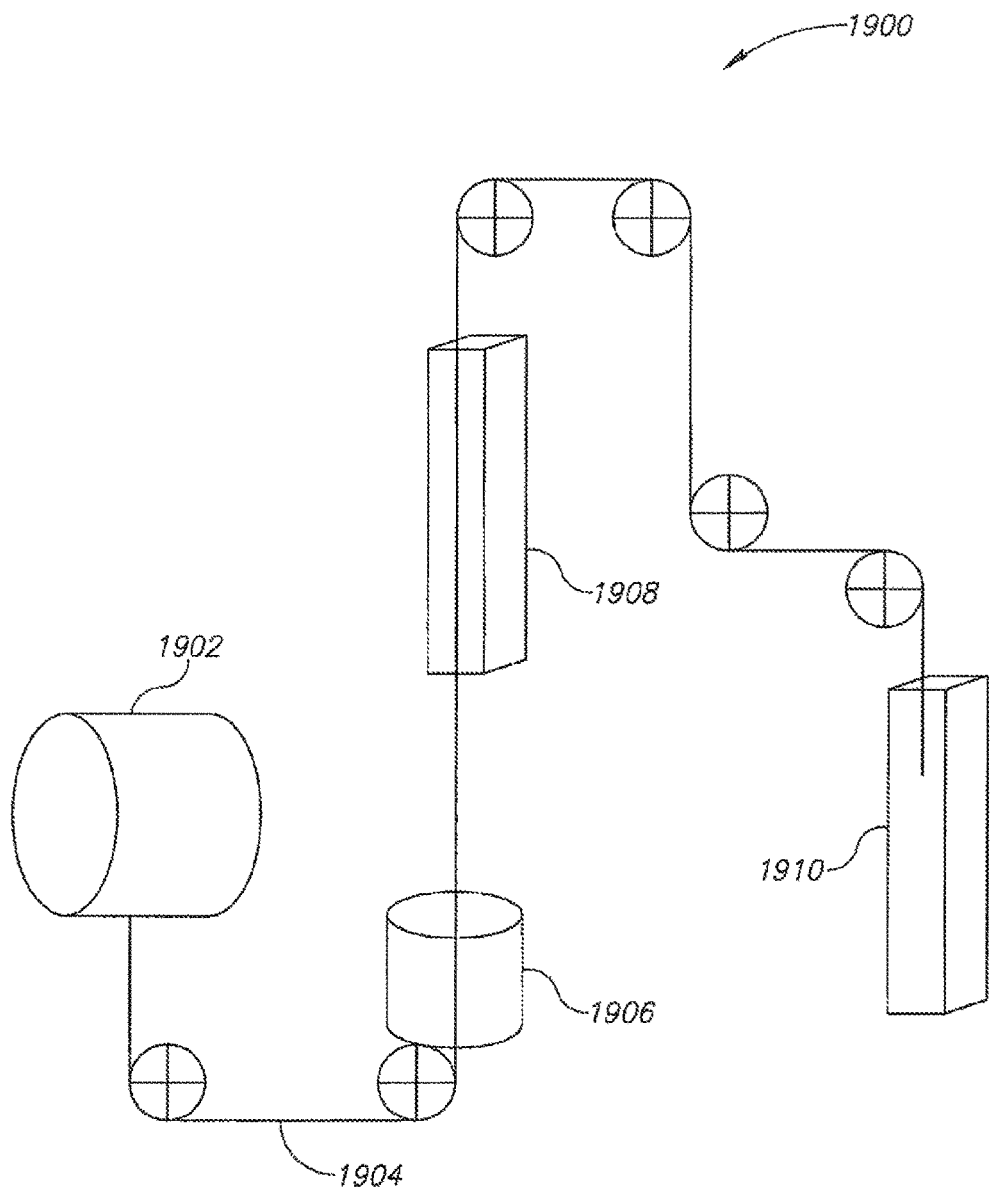
FIG. 19 is a schematic showing a method for manufacturing a porous structure, in accordance with an exemplary embodiment of the invention.

In another exemplary embodiment of the invention, a manufacturing technique is used to coat a fiber that porous structure 104 is comprised of with at least one polymer layer. For example, a dipping technique, shown in FIG. 19, using a biocompatible, hemocompatible, biostable and/or biodegradable polymer dissolved in an organic solvent is utilized to create a dipping solution 1906 for use in coating the fiber comprising porous structure 104. The fiber to be coated is optionally placed in a spool 1902, from which the fiber 1904 is drawn to form porous structure 104. Additives such as drugs, biological components, enzymes, growth factors, and/or any other additive mentioned herein or known in the art, may be incorporated into fiber 1904 during the manufacturing process, for example by placing them in solution 1906 and passing fiber 1904 through solution 1906. In an embodiment of the invention, at least one layer is used in order to control the drug/biological additive's release. For example, more than one solution tank may be provided for fiber 1904 to pass through during manufacture. Fiber 1904 is optionally moved into a drying oven 1908 with an operational temperature range from 37-70 degrees C., (in some embodiments of the invention) depending on the drug used, to dry solution 1906 onto fiber 1904. In an exemplary embodiment of the invention, fiber 1904 is then used by a knitting system 1910 to manufacture porous structure 104. Optionally, knitting system 1910 is the Lamb Knitting Machine Corp. System Model WK6. Optionally, porous structure 104 is coated with a polymer layer after it has been manufactured.

In some exemplary embodiments of the invention, support element 102 and porous structure 104 are coated with an additional substance. Optionally, the additional substance is a polymer. Optionally, the additional substance is drug eluting. Optionally, the coating is hyaluronic acid. Alternatively or additionally, the coating is hyaluronan. Optionally, a different non-woven technology such as wet and/or dry spinning is used to manufacture porous structure 104. In some embodiments of the invention, additional coatings are added to achieve different effects, for example timed release of pharmaceutical agents and/or release of a plurality of agents at different times.

Exemplary Methods for Mounting Porous Structure to Support Element

In some embodiments of the invention, porous structure 104 is at least temporarily secured to support element 102. Advantages of securing porous structure 104 to support element 102, at least temporarily, include: prevention of unraveling and/or run out of fiber from the porous structure weave, dislodgement and/or slipping of porous structure 104 with respect to support element 102 during insertion, delivery and/or deployment. Optionally, support element 102 and porous structure 104 are not secured together using an adhesive and/or other securing means despite being in a coaxial and proximate relationship in many embodiments.

In some exemplary embodiments of the invention, where support element 102 is optionally coated with a polymer, support element 102 and porous structure 104 are attached together by curing at the same time the polymer support element coating and the polymer comprised porous structure, and/or coated porous structure, thus adhering the polymers together. Optionally, pressure and/or heat is used to adhere a polymer coated support element 102 to a non-coated or polymer coated porous structure 104, for example when they are both hot. In some exemplary embodiments of the invention, porous structure 104 is comprised of two components, an external component and an internal component, relative to support element 102. Upon the simultaneous curing of the external and internal components, the polymers of which both are comprised to adhere together, thereby securing porous structure 104 to support element 102, which is located between the components.

In an exemplary embodiment of the invention, porous structure 104 is secured to support element 102 in order to avoid porous structure migration, but not limit porous structure 104 and/or support element 102 expandability.

In some exemplary embodiments of the invention, an adhesive is used to bond support element 102 and porous structure 104 together. Optionally, porous structure 104 is glued to support element 102 utilizing any natural and/or synthetic biocompatible adhesive, such as cyanoacrylate, thermo plastic elastomers, silanes, laminin, albumin and/or fibrinogen and/or PEG-PEG adhesive, and/or polyurethane adhesive and/or any other suitable compatible polymeric material. Optionally, when porous structure 104 is glued to support element 102, wherein the support element 102 is a drug eluting stent, the same polymer as used for the elution of the drug is used for attachment of porous structure 104 to support element 102.

In an embodiment of the invention, porous structure 104 is attached to support element 102 at a plurality of points. Optionally, the plurality of points defines a pattern, such as a line or zigzag of points. Optionally, porous structure 104 compresses onto support element 102 to maintain an attachment to support element 102. Optionally, the porous structure is held in place on support element at least partially by frictional forces. Optionally, porous structure 104 is sewn and/or mechanically entangled onto support element 102. Optionally, heating, pressure, laser welding, UV curing and/or ultrasound are used as techniques to secure porous structure 104 to support element 102. Optionally, a primer, such as parylene, is used on support element 102 prior to adhering porous structure 104 to it in order to enhance cohesion.

Figure 21B:
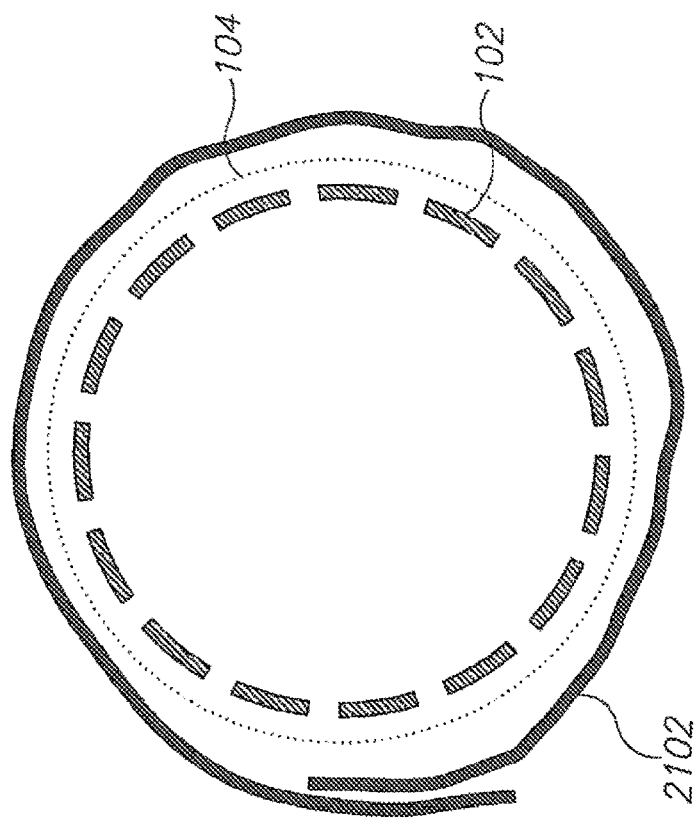
FIG. 21B is a cross-sectional view of a slip ring in a deployed configuration, in accordance with an exemplary embodiment of the invention.
Figure 21A:
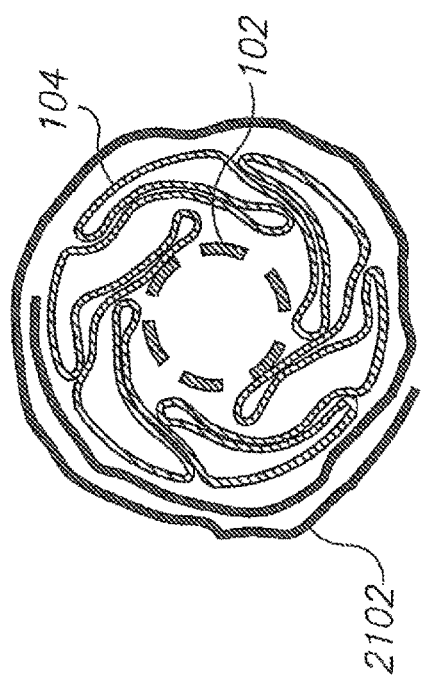
FIG. 21A is a cross-sectional view of a slip ring in a reduced profile configuration, in accordance with an exemplary embodiment of the invention.

In some exemplary embodiments of the invention, elastic and/or expandable o- and/or c-rings are used to hold porous structure 104 on support element 102. Optionally, c-rings are used to avoid hampering expandability of porous structure 104. Optionally, the rings are used to at least temporarily secure and/or apply friction to each end of porous structure 104 to support element 102. Optionally, the rings are coated and/or embedded with pharmaceuticals for elution, such as described herein. Optionally, the rings are constructed of a polymer based material. In some exemplary embodiments of the invention, porous structure 104 is tied to support element 102, optionally using fibers of porous structure 104. In an exemplary embodiment of the invention, a slip ring 2102 is used to secure porous structure 104 to support element 102, as shown in FIGS. 21A and B. Slip ring 2102 is adapted to expand with porous structure 104 and support element 102 when they are expanded upon deployment at a lumen treatment site. Optionally, slip ring 2102 is flexible but is rigid enough to secure porous structure 104 to support element 102. In an embodiment of the invention, slip ring 2102 is coiled around enhanced stent apparatus 100 when it is in a reduced profile configuration such that slip ring 2102 overlaps itself at least partially. Upon deployment, shown in FIG. 21B, support element 102 and porous structure 104 are expanded to provide treatment to the lumen. In an embodiment of the invention, slip ring 2102 expands with them while maintaining sufficient pressure on porous structure 104 to retain it to support element 102. In an embodiment of the invention, the overlapping portion of slip ring 2102 is reduced as a result of the overall increase in diameter of the slip ring 2102. Optionally, slip ring 2102 is comprised of a biodegradable and/or bioresorbable material. In some embodiments of the invention, slip ring 2102 is under 25 microns thick. Optionally, slip ring 2102 is under 15 microns thick. Optionally, slip ring 2102 is under 10 microns thick.

Figure 16:
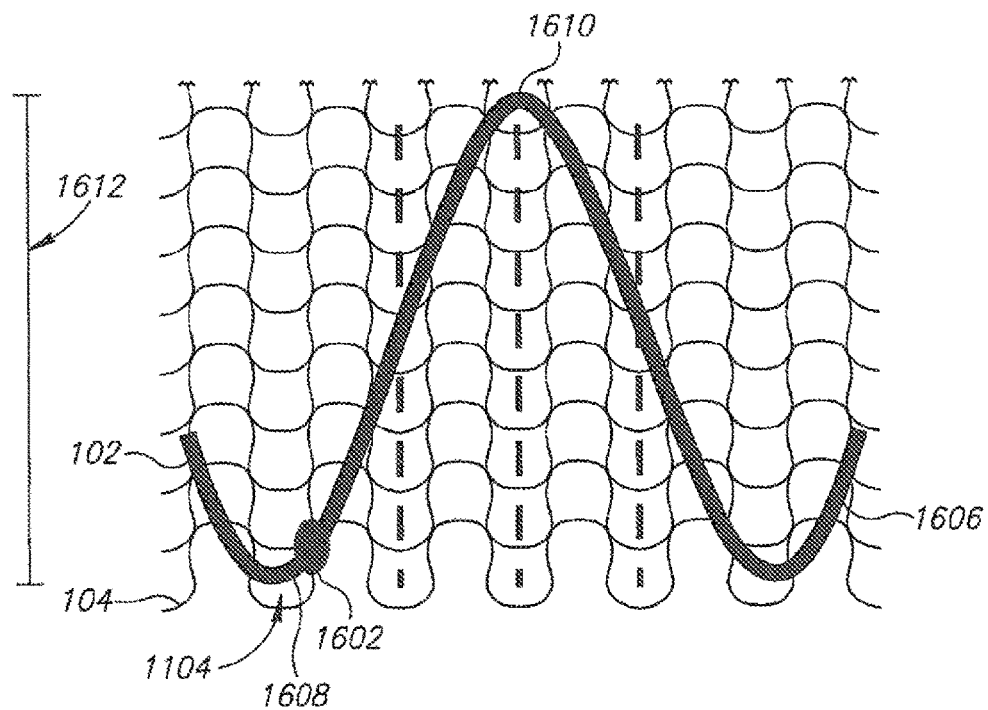
FIG. 16 is a detailed illustration of a threading method for securing a porous structure to a support element, in accordance with an exemplary embodiment of the invention.

Referring to FIG. 16, an embodiment of the invention is shown in which porous structure 104 is attached to support element 102 using a sliding connection 1602. In an exemplary embodiment of the invention, the sliding connection is established by attaching at least one loop 1604 of porous structure 104 to support element 102 in a condition that prevents the two from becoming separated, but is loose enough to allow sliding of porous structure 104 with respect to support element 102. In an embodiment of the invention, a loose stitch is used to attach porous structure 104 to support element 102 in a sliding connection. In an embodiment of the invention, expansion of porous structure 104 is assisted by utilizing the sliding nature of the connection 1602. For example, porous structure 104 is secured to the outermost strut 1606 of support element 102 at its most outlying position 1608. In an embodiment of the invention, on the other side of support element 102 porous structure 104 is also attached to the outermost strut at its most outlying position. When support element 102 and porous structure 104 are expanded during deployment, porous structure 104 is afforded additional expandability, in relation to a pre-expanded configuration, as the sliding connection 1602 moves from the most outlying position 1608 on outermost strut 1606 to an innermost position 1610. The distance 1612, about 1 mm to 6 mm in an embodiment of the invention, from the most outlying position 1608 to innermost position 1610 provides additional expandability to porous structure 104. Optionally, sliding is prevented by securing porous structure 104 to strut 1606 at innermost position 1610 as well as most outlying position 1608. Optionally, sliding is prevented by tightening the connection between the two, for example by providing a tighter stitch.

Figure 17:
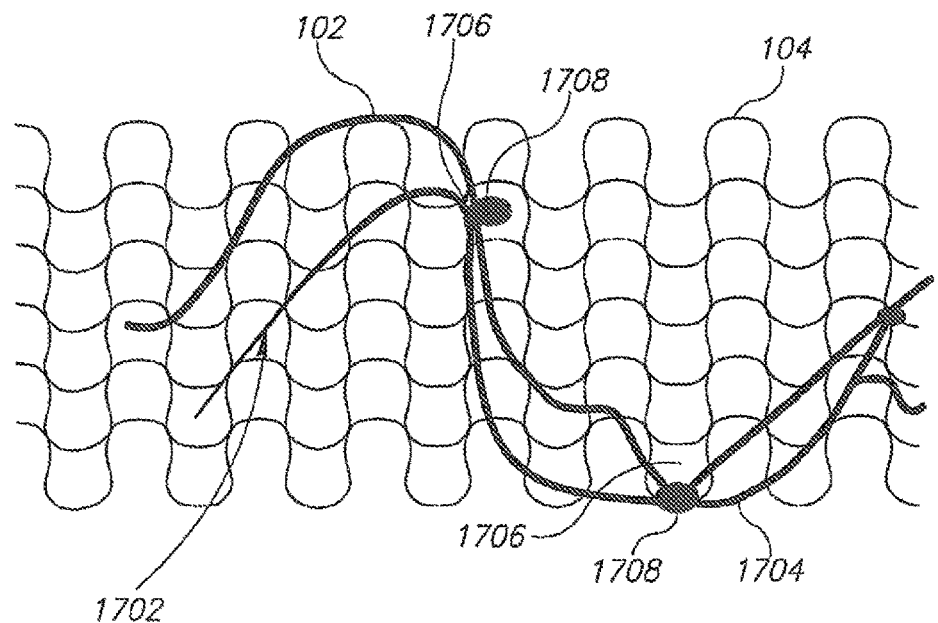
FIG. 17 is a detailed illustration of a knotting method for securing a porous structure to a support element, in accordance with an exemplary embodiment of the invention.

In some embodiments of the invention, porous structure 104 is tied to support element 102 using any one of thumb, square, reef, or double surgeon's knots. Optionally, the at least one fiber used to construct porous structure 104 is used to tie porous structure 104 to support element 102. FIG. 17 shows an exemplary method for attaching porous structure 104 to support element 102 using knotting. It can be seen that a knotting fiber 1702 is used to secure porous structure 104 to support element 102 at various points along a support element strut 1704. Optionally, knotting fiber 1702 is threaded through a plurality of eyes 1706 and over support element strut 1704 wherein a knot 1708 is tied to secure porous structure 104 to support element 102 at least some of the eyes.

As mentioned above, in some embodiments of the invention, securing porous structure 104 to support element 102 is also used to reduce the likelihood of run outs and/or porous structure unraveling. In an embodiment of the invention, run outs and/or porous structure unraveling are to be avoided for at least the reasons of: avoiding porous structure protrusion into the lumen and/or rendering porous structure ineffective for intended treatment of the lumen. In an embodiment of the invention, porous structure 104 is secured to support element 102 at the ends of support element 102, at least some intersections where porous structure 104 and support element 102 overlap, or both and/or every eye at both ends. Any of the methodologies of securing described above are optionally used to secure porous structure 104 to support element 102 to prevent run outs and/or unraveling.

In an exemplary embodiment of the invention, porous structure 104 is treated to supply temporary enhanced adhesion to support element 102 during implantation. For example, enhanced stent apparatus 100 is optionally dipped in a liquid which causes porous structure 104 to adhere to support element 102. Optionally, this adherence is due to surface tension of the liquid. Optionally, this adherence is due to temporary shrinkage of porous structure 104, which secures it to support element 102 more tightly. In some exemplary embodiments of the invention, temporary cohesion is used to prevent porous structure 104 from slipping off of support element 102 as a result of frictional stress experienced during navigation of the vasculature during implantation.

General Pharmacological Usage

Alternatively or additionally to the physical prevention of debris from entering the bloodstream, porous structure 104 optionally contains pharmaceuticals designed to treat a variety of ailments. In some exemplary embodiments of the invention, pharmaceuticals are optionally provided including one or more pharmacological agents for encouraging cell and/or liposomal growth and/or other endothelial cell growth factors, anti-proliferative, anti-thrombotic, anti-coagulant and/or anti-platelet effects, tissue engineering factors, immunomodulators, antioxidants, antisense oligonucleotides, collagen inhibitors, hydrophobic pharmaceuticals, hydrophilic pharmaceuticals and/or endothelial cell seeding substances. Optionally, pharmacological therapy rendered from a porous structure is used to accelerate vein to artery conversion. Specific examples of pharmaceuticals that are optionally used with porous structure 104 include; anti-proliferative agents like sirolimus, zolimus or zotarolimus (ABT-5789), paclitaxel and other taxanes, tacrolimus, everolimus, vincritine, viblastine, HMG-CoA reductase inhibitors, doxorubicin, colchicine, actinomycin D, mitomycin C, cycloporine, and/or mycophenolic acid, triazolopyrimidine and its derivatives (i.e. Trapidilg, a coronary vasodilating drug); intrapide, glucocorticoids like dexamethasone, methylprednisolone, and/or gamma interferon; antithrombotics like heparin, heparin-like dextran derivatives, acid citrate dextrose, coumadin, warfarin, streptokinase, anistreplase, tissue plasminogen activator (tPA), urokinase and/or abciximab; antioxidants like probucol; growth factor inhibitors like tranilast and/or angiopeptin; antisense oligonucleotides like c-myc and/or c-myb; collagen inhibitors like halofuginone and/or batimistat; liposomes; gemcitabine (i.e. Gemzar®); steroids and corticosteroids for example cortisone and prednisone; cortisone, prednisone; Rapamycin®, statin drugs like simvastatin, lovastatin, and/or simvastatine (i.e. Zocor®); VEGF; FGF-2; micro carriers containing endothelial cells; genes; DNA; endothelial cell seeds; and/or hydrogels containing endothelial cells.

Typically, stents (i.e. support elements) which provide pharmaceutical treatment only have the pharmaceutical embedded on the structure of the stent, in particular on the stent struts. This structure is typically minimized in order to provide flexibility and reduce cost, among other reasons. As a result of a minimized support element structure, the struts of the structure are usually spaced widely apart. Thus, when the stent is in situ, and pharmaceuticals are released into the patient from the stent, the pharmaceutical is only diffused from the widely spaced struts. This prevents even distribution of the pharmaceutical over the entire length of the stent. In addition, stent struts are typically large in relation to endothelial cells and therefore formation of a covering endothelial cell layer typically takes on the order of days or weeks, rendering pharmaceutical elution into body tissues delayed and/or ineffective (due to a number of reasons, including the pharmaceutical being washed away by fluids flowing in the lumen before the endothelial cell layer covers the stent).

In contrast, usage of a pharmaceutical enhanced porous structure, such as described herein, to cover the stent, including the struts, provides far more surface area in contact with the inner wall of the patient's blood vessel thereby enabling more diffusion to take place. In comparison to conventional techniques for stent delivered pharmaceuticals, lower concentrations of pharmaceutical are optionally used with the present invention because of its improved therapy-rendering surface area. In an embodiment of the invention, improved delivery by the presently described invention allows for lower doses of pharmaceutical to be used in order to render the same relative amount of treatment, and reduce the overall dosage needed in order to obtain the same results, thus reducing possible side effects. For example, a currently recommended concentration of taxol on a drug eluting stent is around 1 $\mu g/mm^2$ of stent surface. In contrast, a concentration of 0.5 $\mu g/mm^2$ is optionally used with porous structure 104, due to its increased treatment rendering surface area. Optionally, the concentration is less than 0.5 $\mu g/mm^2$. As another example, typical concentrations of rapamycin and limus drugs today are around 140 $\mu g/cm^2$, however, using the herein described porous structure 104 a concentration of 80 $\mu g/cm^2$ is optionally used to achieve the same therapeutic effect. In some exemplary embodiments of the invention, as little as 10 $\mu g/cm^2$ is optionally used to achieve the same therapeutic effect. In some exemplary embodiments of the invention, concentrations of pharmaceutical embedded on porous structure are up to 15 times less than conventionally used today.

In conventional stents, at the struts, the pharmaceutical may not propagate far enough and/or without effect into the vascular wall, or may overdose a particular section of the vascular wall, without sufficient propagation laterally to the rest of the inner surface where it is needed. Having additional surface area, more evenly covering the stent surface area, porous structure 104 can deliver drugs in a more locally homogenous way. Optionally, there is an axial profile change in dosage. Since distribution of the drug into the tissue is governed by diffusion, and since the amount of dosage concentration on the struts is limiting due to over toxicity and side effects, spreading the drug in a more even manner is very helpful for obtaining better pharmacokinetics.

In an exemplary embodiment of the invention, pharmaceuticals to be administered to patient are located in and/or on the fibers of porous structure 104. Examples of where and how pharmaceuticals are optionally located in and/or on the fibers of porous structure 104 and/or eluted include:

1. depositing pharmaceutical in the apertures of porous structure;
2. mixing pharmaceutical particles into fibers of porous structure at fiber creation;
3. applying pharmaceutical topically to the porous structure, such as by spraying;
4. dipping porous structure into a solution containing a pharmaceutical additive, thereby depositing the additive on and/or in the fibers of the porous structure;
5. encapsulating a pharmaceutical additive on porous structure, optionally using a thermal process;
6. grafting a pharmaceutical additive onto porous structure using plasma treatment;
7. etching a pharmaceutical additive into porous structure, for example via spattering or coating;
8. transferring a pharmaceutical additive to porous structure using concentration differences between the porous structure and art additive containing substance, for example by adhering micro carriers containing pharmaceutical additive to a porous structure allowing their migration into the porous structure;
9. any method known to those skilled in the art, such as shown in U.S. Pat. App. No. 2004/0030377 to Dubson et al., U.S. Pat. App. No. 2005/0187140 to Hunter et al., U.S. Pat. App. No. 2004/0236407 to Fierens et al., U.S. Pat. No. 6,902,522, to Walsh, et al., U.S. Pat. No.

6,669,961 to Kim, et al., U.S. Pat. No. 6,447,796 to Vook, et al., U.S. Pat. No. 6,369,039 to Palasis et al., U.S. Pat. No. 6,939,374 to Banik, et al., and U.S. Pat. No. 6,919,100 to Narayanan, the contents of which are herein incorporated by reference:

10. elution of the drug from a polymer coating the porous structure fibers;
11. elution of the drug from the polymer from which the porous structure is constructed; and,
12. incorporating the drug in a biodegradable polymer.

Optionally, embedding of the pharmaceutical occurs before (e.g. mixing pharmaceutical particles into fibers of porous structure at fiber creation), during (e.g. using the dipping method of FIG. 19) and/or after (e.g. a spray on pharmaceutical after apparatus is made) the manufacture of enhanced stent apparatus 100. In some exemplary embodiments of the invention, a pharmaceutically embedded porous structure 104 is placed on top of a pharmaceutically treated support element 102. In some exemplary embodiments of the invention, porous structure 104 is coated with at least a polymer. In some exemplary embodiments of the invention, a porous structure is provided with a polymer coating which contains a pharmaceutical which elutes from the coating.

Pharmaceuticals are optionally embedded into porous structure 104 such that they are released into the patient over an approximate predetermined amount of time. For example, pharmaceuticals are optionally embedded into porous structure 104 for release over the course of a week. Other pharmaceuticals are optionally embedded into porous structure 104 for release over the course of months. Factors which vary according to the release schedule of the pharmaceutical include the type of material used to construct porous structure 104, the type of pharmaceutical being used, the manner in which porous structure 104 is constructed, and/or the amount of coverage of support element 102 that porous structure 104 provides.

In some exemplary embodiments of the invention, 1 microgram of pharmaceutical per square centimeter of fiber surface coverage (not the area of the fiber themselves, but the area of the tissue it treats) area is embedded on the fibers. Optionally, up to 200 micrograms of pharmaceutical per square centimeter of fiber surface area is embedded on the fibers. Optionally, a higher or lower concentration of pharmaceutical is used depending on the therapeutic needs of the patient and depending on the type of drug used.

Large and/or Complicated Stereochemistry Molecule Pharmaceutical Usage

In some exemplary embodiments of the invention, usage of porous structure 104 for enhanced pharmaceutical delivery allows for effective dispersion and delivery of large molecule and complex stereochemistry pharmaceuticals. Traditionally, large molecule pharmaceuticals are not used with drug eluting stents because they don't diffuse very well and the widely spaced struts of traditional stents do not facilitate even and/or widespread diffusion of the large molecule, as described above. In contrast, use of a device with more extensive coverage of a vascular wall would make treatment using large molecule pharmaceuticals more feasible. This is optionally accomplished by providing porous structure 104 and/or support element 102 with large molecule pharmaceuticals for elution and taking advantage of the increased vascular wall coverage of porous structure 104, due to the smaller aperture sizes in some exemplary embodiments. Alternatively or additionally, due to the overgrowth of porous structure 104 by cells from the body, large molecule pharmaceuticals are more efficiently delivered to the patient as pharmaceuticals are delivered into tissue, rather than being washed away in the blood stream, for example. Optionally, pharmaceuticals larger than 700 Dalton, 1,000 Dalton, 3,000 Dalton or up to 50,000 Dalton are dispersed and delivered evenly into patient's vasculature.

Figure 3:
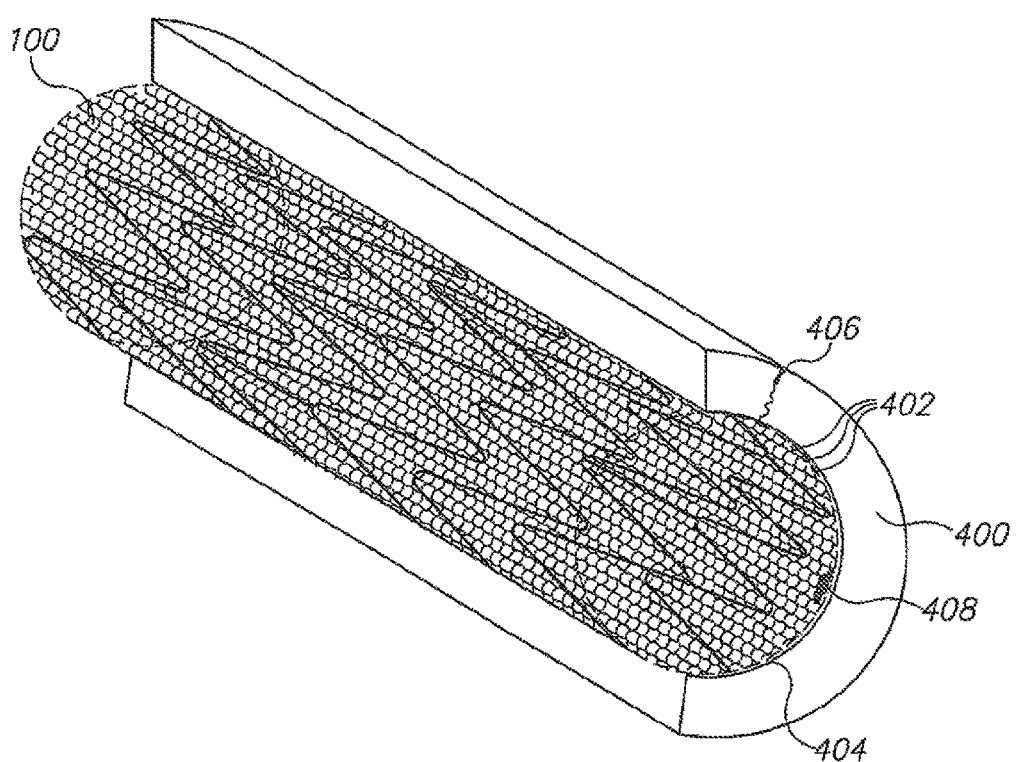
FIG. 3 is an illustration of an enhanced stent apparatus in an open mode in situ, in accordance with an exemplary embodiment of the invention.

Optionally, liposomes are eluted from at least one porous structure 104 and/or support element 102. Optionally, steroids, statins, anticoagulants, gemcitabine (Gemzar®), zolimus or zotarolimus (ABT-578®), sirolimus (e.g. Rapamycin®), taxol/paclitaxel, and/or other large or complex molecule pharmaceuticals are eluted from at least one porous structure 104 and/or support element 102. Referring to FIG. 3, pharmaceutical agents 406 are shown eluting from enhanced stent apparatus 100 into artery 400 from lumen wall 404. Optionally, agents 406 elute from porous structure after at least some growth of endothelial cells 408 through enhanced stent apparatus 100, for example the time determined by experimental endothelial cell growth data. As described elsewhere herein, porous structure 104 optionally acts to trap debris 402 between the exterior surface of enhanced stent apparatus 100 and lumen wall 404.

Timed Release Pharmaceutical Usage

In an exemplary embodiment of the invention, pharmaceuticals are eluted from an enhanced stent apparatus into overgrown endothelial tissue and not merely into the interior surface of the lumen being treated. In an exemplary embodiment of the invention, pharmaceutical release is thus optimized by ensuring that only a pre-defined amount of drug is lost into the bloodstream and/or into other non-therapeutic media. In some exemplary embodiments, including, for example, in conjunction with BBB treatment as described below, endothelial cell growth can assist with pharmaceutical therapy by providing a transfer medium for the pharmaceutical from an implanted stent to the body area being treated.

In some exemplary embodiments of the invention, pharmaceuticals are eluted depending on the extent of endothelial tissue growth. Optionally, pharmacological treatment commences after some endothelial cell growth is exhibited through and/or around the enhanced stent apparatus. Optionally, pharmacological treatment begins upon implantation without regard to endothelial cell growth. In some exemplary embodiments of the invention, the enhanced stent apparatus is adapted and constructed to time-release pharmaceuticals in accordance with a predetermined treatment schedule. Optionally, the predetermined treatment schedule accommodates anticipated and/or actual endothelial cell growth rates by utilizing a coating with a predetermined breakdown rate. Optionally, release of pharmaceuticals is determined by time in situ. For example, if it is estimated that it would take 8 hours for endothelial cell growth to completely encapsulate the implanted stent, pharmaceuticals located in the porous structure of the stent optionally have a predetermined 8 hour delay prior to release and/or elute at a low rate to prevent inefficient or undesirable (i.e. toxic overdose) use of the pharmaceutical. In an embodiment of the invention, it takes only few hours for the endothelial cells to cover the thin porous structure, therefore the time release delay is adapted to match. This may be achieved by coating porous structure 104 with a "diffusion barrier" layer that inhibits the diffusion of drug for a predefined period. Optionally this may be achieved by using a controlled degradable matrix. Optionally, pharmaceutical release occurs after only partial growth of endothelial cells around and/or through porous structure and/or stent. Optionally, pharmaceuticals begin to elute immediately upon insertion and/or implantation into a body lumen. Optionally, it is sufficient for pharmaceutical therapy that porous structure 104 has any biological covering, such as mucus, etc. In some embodiments of the invention, delay is determined according to the material that is expected to overgrow porous structure 104.

In an exemplary embodiment of the invention, timed release of pharmaceuticals is accomplished by coating and/or constructing porous structure 104 and/or support element 102 of multiple biodegradable/resorbable layers. By using layers which offer different performance characteristics (e.g. different pharmaceutical, different degradation time, stickiness to the body lumen, surface treatment modifications (e.g. treatment to make it non-sticky to the lumen)), enhanced stent apparatus 100 can be tailored to perform a specific treatment schedule. For example, layer #1 (the external layer) is comprised of a material which degrades in 2 hours, layer #2 (an inner layer) includes a pharmaceutical for elution into the patient and which degrades in 10 hours, layer #3 (an inner layer) includes a different pharmaceutical for elution into the patient which degrades in 6 hours, and so on. Naturally, depending on the therapy desired for the patient, the layers and/or performance characteristics of those layers are changed to provide the desired treatment. It should be noted that a biodegradable layer can be placed in the outermost position which is timed to the expected endothelial cell growth, as described above. In such an embodiment, the degradation of the outermost layer is completed at approximately the same time as the completion of the endothelial cell layer overgrowth of enhanced stent apparatus 100, enabling a pharmaceutical to be eluted directly into endothelial tissue from a second layer of enhanced stent apparatus 100.

In an exemplary embodiment of the invention, support element 102 elutes pharmaceuticals, but treatment is assisted by porous structure 104 which encourages endothelial cell growth over support element 102. Optionally, the pharmaceutical located on support element 102 elutes slowly to allow for endothelial cell growth. In some embodiments of the invention, the rate of elution depends on the local concentration and the anticipated diffusion rate of the pharmaceutical through the surrounding body tissue.

In some embodiment of the invention, a first pharmaceutical agent is eluted, which is designed to encourage endothelial cell overgrowth, followed by a second pharmaceutical agent designed to treat a malady of the patient.

In some embodiments of the invention, at least porous structure 104 is attached to the lumen using an adhesive which is impermeable to the pharmaceutical in porous structure 104. However, timed release is achieved by allowing the endothelial layer to overgrow porous structure 104, such that the pharmaceutical will elute into the endothelial layer that is not proximal to the adhesive. Optionally, the adhesive is biodegradable and/or bioresorbable and merely delays elution.

Blood Brain Barrier (BBB) Therapy

The BBB is the specialized system of capillary endothelial cells that protects the brain from harmful substances in the blood stream, while supplying the brain with the required nutrients for proper function. Unlike peripheral capillaries that allow relatively free exchange of substance across/between cells, the BBB strictly limits transport into the brain through both physical (tight junctions) and metabolic (enzyme) barriers. Thus the BBB is often the rate-limiting factor in determining permeation of therapeutic drugs into the brain.

In some exemplary embodiments of the invention, a pharmaceutical eluting porous structure is used to enable treatments through the BBB. As described herein, pharmaceutical therapy is often enhanced by endothelial cell growth through and/or around an implanted drug eluting stent. Use of porous structure 104 in brain arteries, allows the endothelium cells to grow over the porous structure 104, thus embedding porous structure 104 into the arterial tissue. The end result, after the previous endothelial cell layer has been absorbed by the body is that porous structure 104, which contains a brain treating pharmaceutical, is on the other side of the endothelium layer, thus on the other side of the BBB, with no significant impediment between porous structure 104 and the brain tissue. In addition, some exemplary embodiments of porous structure 104 are suitably sized to be used in the narrow lumens found in the brain. Exemplary pharmaceuticals suitable for use with porous structure 104 in treating through the BBB include gemcitabine (Gemzar®), and enzastamin, dopamine and dopamine derivatives, and anti-cancer drugs. In some embodiments of the invention, porous structure 104 elutes anti-BBB materials for lowering resistance to transmission of substances through the BBB.

Pharmaceutical Treatment of Small Lumens

Currently, small lumens such as small coronary or brain arteries are treated only with a balloon type catheter. These treatments are short term and do not lend themselves to rendering pharmaceutical treatment to the lumen, as is sometimes desired. Traditional stenting is not often performed at the very least due to the difficulty of navigating a stent into the small spaces of these arteries. In an exemplary embodiment of the invention, lumens smaller than 2 mm in diameter are treated with pharmaceuticals using at least a pharmaceutical eluting porous structure 104, and optionally a support element. Optionally, the support element is a stent. Optionally, the support element is a balloon on which porous structure 104 is placed. In an exemplary embodiment of the invention, a balloon-type catheter is used to insert porous structure 104 in a small lumen. The balloon is expanded to cause porous structure 104 expansion and to instigate contact between porous structure 104 and the lumen wall to be treated. In an embodiment of the invention, porous structure 104 at least partially adheres to the lumen wall. Optionally, a biocompatible adhesive is used to adhere porous structure 104 to the lumen wall. In some embodiments of the invention, porous structure 104 is self-expandable and does not need, or only partially relies on the balloon for expansion. In an embodiment of the invention, the balloon is removed once porous structure has been deployed within the small lumen.

In some embodiments of the invention, small lumens are treated long term, which is not performed currently. For example, by implanting at least the porous structure of an enhanced stent apparatus 100, treatment can last on the order of months (e.g. a month or more). Optionally, treatment can last on the order of weeks (e.g. a week or more).

Exemplary Treatment Methods

In an exemplary embodiment of the invention, enhanced stent apparatus 100 is used for treating, dilating, drugging, and/or supporting body lumens, such as blood vessels. In some exemplary embodiments of the invention, enhanced stent apparatus 100 is used for treatment of disorders in the carotid arteries. In some embodiments of the invention, enhanced stent apparatus 100 is used for treatment of disorders in the coronary arteries. As described above, treatment can be rendered through the BBB. Stent apparatus 100 can be either a balloon expandable stent or a self-expandable stent, or use any other expansion method. Optionally, support element 102 and/or porous structure 104 are self-expandable. Optionally, pharmaceuticals are used to treat a patient via body lumens, for example, as described herein. In some embodiments of the invention, enhanced stent apparatus 100 is used for treatment of aneurisms (described below), for example in the brain. In some embodiments of the invention, enhanced stent apparatus 100 is used for preventative treatment of vulnerable plaque.

In operation, enhanced stent apparatus 100 is navigated to the area in a body lumen 400, as shown in FIG. 3, where the enhanced stent apparatus 100 is to be emplaced, using techniques known in the art. In some exemplary embodiments of the invention, enhanced stent apparatus 100 can be expanded within body lumen 400 using a balloon. Optionally, enhanced stent apparatus 100 can be expanded within body lumen 400 using self-expandable techniques known in the art. Optionally, support element 102 and/or porous structure 104 are constructed of a thermo-sensitive, shape memory alloy which, when exposed to a patient's natural body temperature, assumes an expanded shape within body lumen 400 at some time after situation in the appropriate location to render treatment. Alternatively, super-elastic or elastic release is used for placing a stent in a treatment area. In some exemplary embodiments of the invention, a balloon is used to pre-dilate body lumen 400 at a treatment area prior to implantation of enhanced stent apparatus 100 at that area, in an at least a two-step (1. pre-dilate, 2. implant apparatus 100) procedure. Optionally, only porous structure 104 is implanted and not the whole enhanced stent apparatus 100. In some exemplary embodiments of the invention, a balloon is used to post-dilate body lumen 400 at a treatment area after implantation of enhanced stent apparatus 100 at that area, in an at least a two-step (1. implant apparatus 100, 2. post-dilate) procedure. This kind of procedure is commonly used when implant apparatus 100 is a self-expandable stent, such as for carotid applications.

In some exemplary embodiments of the invention, the porous structure mesh is filled with a material which improves the stiffness of the porous structure temporarily until it arrives at a treatment site in a lumen. In some embodiments of the invention, the material is dissolved by naturally occurring substances in the body, such as enzymes. Optionally, the dissolving is timed to the anticipated overgrowth of porous structure 104 by the endothelial cell layer. Optionally the material is fibrogane. Optionally, the material is albumin fibrogane helonic acid laminin.

Exemplary Treatment of Embolic Showers at Insertion and/or Deployment

It is commonplace in stenting procedures to use an embolic shower protection device which is situated only during the stenting procedure downstream from the treatment area, the idea being that the protection device will trap debris which falls from the blood vessel walls during the stenting procedure. In an exemplary embodiment of the invention, usage of enhanced stent apparatus 100 with porous structure 104 obviates the need for an embolic shower protection device. The small aperture size of porous structure 104 is designed to trap arterial wall plaque 402 and other debris of a particular size that becomes dislodged during and/or after the stenting procedure, between porous structure 104 and the lumen wall 404. In an exemplary embodiment of the invention, debris greater than the size of the apertures in diameter is prevented from entering the bloodstream in this manner.

An additional advantage of using implanted porous structure 104 instead of a conventional embolic shower protection device is that it remains in place after the procedure. That is, debris which becomes dislodged at some time after the stenting is performed still becomes trapped by porous structure 104. This is an improvement over the embolic shower protection device conventionally used, which is removed at the conclusion of the stenting procedure. Optionally, enhanced stent apparatus 100 is used with an embolic shower protection device as reassurance during the stenting procedure. Optionally, porous structure 104 filters a particular type or types of debris while support element 102 filters another type or types.

It should be noted further that in an exemplary embodiment of the invention the aperture sizes of the porous structure 104 are designed and constructed to permit the passage of blood therethrough. This prevents the "jailing" of branching blood vessels which prevents the passage of critical blood components, such as red blood cells from passing into the branching vessel. In an exemplary embodiment of the invention, the aperture size of porous structure 104 is larger than the average size of a red blood cell, or about 7 microns, allowing throughput of red blood cells without the risk of producing significant hemolysis. In some exemplary embodiments of the invention, the approximate aperture diameters are greater than 20 microns. In some exemplary embodiments of the invention, the approximate aperture diameters are smaller than 100 microns thus allowing blood to flow through while holding large debris (>100 microns) in place.

Carotid stenting is rarely performed currently, due to the high risk of debris becoming dislodged during the stenting procedure. This dislodged debris then travels to the brain where it often causes serious injury to the patient. In order to combat this problem of dislodged debris, enhanced stent apparatus 100, which includes porous structure 104, is used for stenting in the carotid arteries in some exemplary embodiments of the invention.

Exemplary Treatment of Aneurisms

Figure 20A:
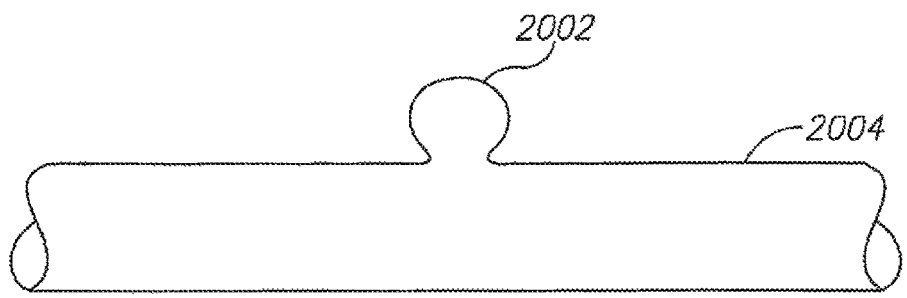
FIG. 20A is an illustration of a typical aneurism.
Figure 20B:
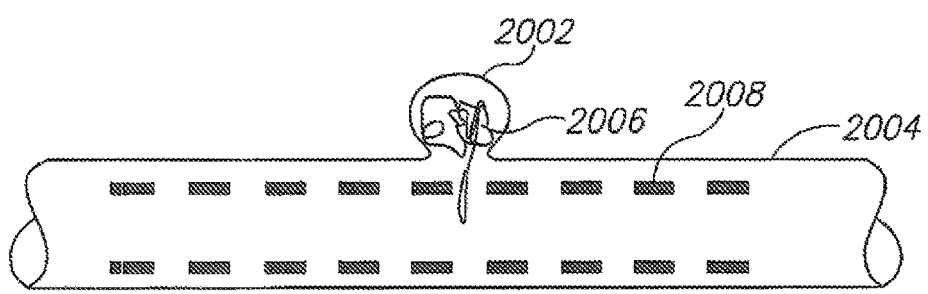
FIG. 20B is an illustration of a prior art technique for treating an aneurism.

Referring to FIG. 20A, a typical aneurism volume 2002 is depicted promulgating from a body lumen 2004. FIG. 20B shows a current method of treating an aneurism called coil embolization. Coil embolization is particularly indicated for treatment of cerebral aneurisms. Coil embolization of cerebral aneurisms involves the insertion of a catheter through the groin with a small microcatheter navigated to the aneurism itself through the cerebral arteries. A coil 2006 is then deployed into the aneurism filling it from within and thus disturbing the blood flow in the aneurism volume. This effect that leads to the creation of blood clot which is trapped in aneurism volume 2002 and which eventually turns into a more solid structure, thus reducing the risk of rupture of the aneurism. In some treatments, a stent 2008 is also used in order to keep coil 2006 from falling out of aneurism volume 2002 and into the blood stream. However, in some cases parts of coil 2006 protrude through stent 2008 and are therefore exposed to the blood flow within the lumen 2004. Additionally, safe insertion of coil 2006 into aneurism volume 2002 can be a complicated procedure. Additionally, the blood clot produced might grow through the stent struts into the blood vessel lumen, narrowing it possibly to the point of complete occlusion.

Figure 20C:
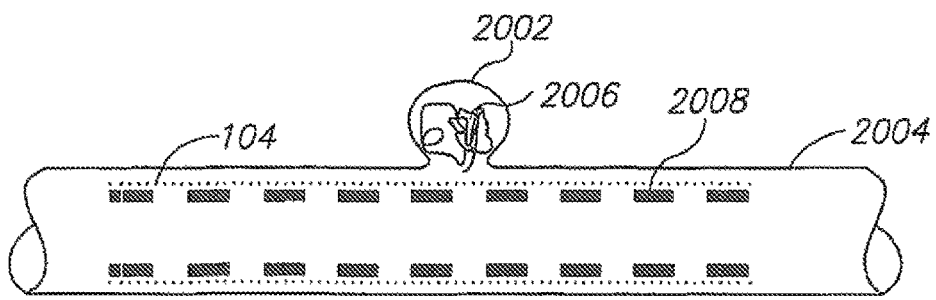
FIG. 20C is an illustration of a technique for treating an aneurism, in accordance with an exemplary embodiment of the invention.

Referring to FIG. 20C, an embodiment of the invention is shown in which porous structure 104 located on enhanced stent apparatus 100 is used to treat an aneurism while preventing coil 2006 from protruding into lumen 2004. Optionally, a cerebral aneurism is treated by this method. Porous structure 104 is adapted to have aperture sizes which are small enough to prevent coil 2006 from protruding into lumen 2004, in accordance with an embodiment of the invention. Optionally, a plurality of porous structures are used at least slightly out of phase in order to prevent at least a portion of coil 2006 from protruding into lumen 2004. In some exemplary embodiments of the invention, coil 2006 is covered with a porous structure (separate from porous structure 104), thereby creating more surface area for the blood to stick to, enhancing the creation of a blood clot within the aneurism volume 2002. In some embodiments of the invention, porous structure 104 is manufactured using an electrospinning technique.

In an exemplary embodiment of the invention, enhanced stent apparatus 100 is used to treat an aneurism without the need for coil 2006. In some embodiments of the invention, porous structure 104 is adapted to restrict blood flow into aneurism volume 2002, thus causing the trapped blood in aneurism volume 2002 to clot, which in time will solidify and create a solid tissue structure thus reducing the likelihood of aneurism rupture or expansion as a result of increased blood flow thereto. For example, the aperture sizes in porous structure 104 may be small or spaced widely apart. Optionally, a plurality of "out of phase" porous structures are used together to restrict blood flow into aneurism volume 2002. Optionally, porous structure 104 has apertures smaller than 20 microns. Eliminating the need of coil 2006 is advantageous, as it makes the procedure faster, safer, and simplifies the delivery catheter that can be used to perform the procedure.

In some exemplary embodiments of the invention, porous structure 104 is shorter than support element 102. A shorter porous structure 104 is optionally used so that only the aneurism is treated and not a healthy portion of the lumen. Optionally, a shorter porous structure 104 is used to avoid restricting blood flow to a branching vessel. Optionally, porous structure 104 has small aperture sizes on the aneurism side for restricting flow therethrough, while the other side has larger apertures to avoid restricting blood flow to a branching vessel.

In some exemplary embodiments of the invention, porous structure 104 is comprised of a self-expanding material, such as nitinol, having enough radial force to hold itself in place within the lumen. Optionally, a support element 102 is not used at all and porous structure 104 provides the necessary treatment to the aneurism. Optionally, the radial pressure applied by porous structure 104 is equivalent to about 1 atmosphere. Optionally, the aperture diameters for aneurism treatments are smaller than 30 microns.

In some embodiments of the invention, porous structure 104 also prevents blood clots and/or other embolism-causing debris from entering the lumen 2004 from aneurism volume 2002.

Exemplary Treatment of Vulnerable Plaque

Identification of vulnerable plaque areas allows prophylactic treatment of these areas before they can create problems for the patient. In an embodiment of the invention, an enhanced stent apparatus 100 is used to preemptively treat lumen areas expected to trigger problematic conditions for the patient in the future. For example, plaque often builds up in blood vessels which in some cases breaks off in a clump or partially tears, causing a thrombosis. The downstream movement of the plaque or thrombosis is a potential cause of a heart attack, stroke or other malady in the patient. In some embodiments of the invention, an enhanced stent apparatus, including at least porous structure 104 is implanted at a potentially problematic location within a lumen, preventing the plaque from rupturing and, thus, from entering the bloodstream. In some embodiments of the invention, porous structure 104 elutes at least one pharmaceutical used for treating the condition affecting the lumen, such as those described herein. In some embodiments of the invention, porous structure 104 is made of nitinol as a self-expandable stent, having enough radial force to hold itself in place, without the supportive element 102.

Exemplary Method of Implantation

In some exemplary embodiments of the invention, porous structure 104 is positioned on a catheter, such as an expandable balloon, for implantation in a lumen separately from or without support element 102. Treatment with a catheter is optionally provided by using the catheter to implant porous structure 104 adapted and constructed for rendering treatment to a lumen over time. Optionally, pharmaceuticals or other therapeutic agents are embedded within porous structure 104, such as described herein. Positioning, in an exemplary embodiment of the invention, entails inserting the catheter at least partially through the interior of porous structure 104 along central axis 106. In some embodiments of the invention, a balloon is deflated prior to positioning of porous structure 104 thereon. Optionally, the balloon is at least partially inflated prior to positioning of porous structure 104 thereon and then deflated and/or folded prior to insertion into the patient.

During delivery of porous structure 104 to a treatment site within a lumen, a balance is optionally struck between securing porous structure 104 to the catheter during delivery, but not so securely as to prevent implantation of porous structure 104 at the treatment site, and allowing deflation of a balloon and/or pulling the catheter out while leaving the porous structure 104 inside the lumen intact. For example, porous structure 104 is optionally adhered to catheter at selected points using an adhesive such as Loctite instant adhesive number 40340, 40840, 46040 or 3411-uv curable. The adhesive is strong enough to prevent porous structure 104 from slipping off the catheter during delivery, however upon self-expansion or expansion of balloon the bonds between porous structure 104 and the catheter are broken, allowing for implantation of porous structure 104 at a treatment site within a lumen. In some embodiments of the invention, delivery lasts for 6 hours or less. Optionally, delivery lasts for 3 hours or less. Optionally, delivery lasts for 1 hour or less.

In some exemplary embodiments of the invention, the catheter is treated with an anti-sticking agent such as Parylene-c, silicon coating and/or Teflon® coating, to help prevent porous structure 104 from staying fastened to catheter after deployment at treatment site. Optionally, a thin film is coated onto the catheter which secures porous structure 104 to the catheter during the delivery, but dissolves upon an approximate lapsing of time, allowing porous structure 104 to be removed from the catheter. Optionally, the thin film is comprised of albumin fibrogene helonic acid laminin. Optionally, the thin film layer is up to a few microns thick. Alternatively, the thin film layer is 0.1 microns in thickness.

In some exemplary embodiments of the invention, the mesh-like structure of porous structure 104 is filled and/or encapsulated with a gel type material, such as fibrogane, fibrinogen and/or hyaluronic acid and/or luminin. The gel material stiffens porous structure 104 for delivery, however, upon extended exposure to intra-lumen conditions, the gel dissolves leaving only porous structure 104 after some period of time, for example a few hours or days.

In an embodiment of the invention, an adhesive material which is sensitive to a certain threshold (e.g. 1 atm. up to 20 atm.) of pressure is placed on porous structure 104 such that when the balloon pressures porous structure 104 against the lumen, porous structure 104 adheres to the lumen. In an exemplary embodiment of the invention, when porous structure 104 is coated with the pressure sensitive adhesive it is only coated on the lumen side of porous structure 104. Optionally, porous structure 104 is covered with a selectively adhesive material which has a high affinity for adhering to body tissue, for example fibrin sealant, biological glue, collagen, hydrogel, hydrocolloid, or collagen algirate, but limited affinity for adhesion to other substances, such as a delivery catheter or balloon.

Upon arrival at a lumen treatment site, the balloon is expanded in order to place porous structure 104, in accordance with an exemplary embodiment of the invention. As described above, porous structure 104 is optionally placed on the balloon such that when the balloon is expanded, porous structure 104 is expanded correspondingly. In some exemplary embodiments of the invention, the balloon is expanded until it begins to apply pressure to the internal surface of the lumen being treated. The amount of pressure exerted by the balloon is variable depending on the purpose and technique used to carry out the treatment. In some exemplary embodiments of the invention, the balloon is expanded to press porous structure 104 against an interior surface of the lumen being treated. Optionally, the expansion pressure is used to overcome a stenosis being treated. Optionally, porous structure 104 is at least temporarily fastened to the interior surface of the lumen with the assistance of an adhesive. In some exemplary embodiments of the invention, porous structure 104 is at least temporarily attached using at least one barb or pin located on an exterior surface of porous structure 104 facing the inside surface of the blood vessel. Optionally, the adhesive is applied to the exterior surfaces of porous structure 104 prior to insertion into the lumen. In some exemplary embodiments of the invention, once porous structure 104 is placed at the treatment site within the lumen, a support element 402 is implanted at the same site interior of porous structure 104 in relation to the interior surface of the lumen, thus sandwiching porous structure 104 between support element 102 and the lumen.

In some exemplary embodiments of the invention, porous structure 104 provides mechanical support to a blood vessel wall. Optionally, porous structure 104 support is in addition to support rendered by support element 102. Alternatively, porous structure support 104 is in lieu of support rendered by support element 102. In some exemplary embodiments of the invention, support element 102 provides no or minimal support to the blood vessel wall while supporting porous structure 104. Optionally, porous structure 104 provides pharmacological treatment to blood vessel while providing no or minimal support to blood vessel. Optionally, porous structure 104 is implanted along with support element 102, however support element 102 degrades in situ, leaving porous structure 104. Optionally, porous structure 104 prevents support structure 102 from falling apart in large pieces, permitting release of piece of support structure 102 only when below a certain threshold size, for example under 20 microns in diameter. Optionally, porous structure 104 is implanted along with support element 102, however porous structure 102 degrades in situ, leaving support element 102. This last configuration is sometimes indicated when porous structure 104 is made of a polymer containing a pharmaceutical. Eliminating the polymer and the pharmaceutical after period of time has an advantage because it reduces the likelihood of long term side effects such as thrombosis associated with the presence of the polymer and the pharmaceutical.

The present invention has been described using non-limiting detailed descriptions of embodiments thereof that are provided by way of example and are not intended to limit the scope of the invention. It should be understood that features and/or steps described with respect to one embodiment may be used with other embodiments and that not all embodiments of the invention have all of the features and/or steps shown in a particular figure or described with respect to one of the embodiments. Variations of embodiments described will occur to persons of the art. Furthermore, the terms "comprise," "include," "have" and their conjugates, shall mean, when used in the disclosure and/or claims, "including but not necessarily limited to".

It is noted that some of the above described embodiments may describe the best mode contemplated by the inventors and therefore may include structure, acts or details of structures and acts that may not be essential to the invention and which are described as examples. Structure and acts described herein are replaceable by equivalents, which perform the same function, even if the structure or acts are different, as known in the art. Therefore, the scope of the invention is limited only by the elements and limitations as used in the claims.

What is claimed is:

1. A carotid stent assembly adapted to carotid arterial placement, comprising:
   a self-expanding support element having a distal end and a proximal end and comprising metal struts, including a distal strut disposed at the distal end and a proximal strut disposed at the proximal end, the support element constructed to be positioned in a body lumen and expanded from a retracted state to an expanded state; and
   a knitted cover disposed over an exterior of the support element and along an entire length thereof, wherein the knitted cover and the support element are attached together only at the distal strut at a distal end of the knitted cover and the proximal strut at a proximal end of the knitted cover, wherein the knitted cover comprises a single polymer fiber having a diameter of at least 40 nanometers to 30 microns, wherein the self-expanding support element and knitted cover together have apertures sized 20 microns to smaller than 100 microns in diameter to block larger debris when the carotid stent assembly is placed in a carotid artery and expanded to the expanded state,
   wherein the knitted cover and the support element are attached together by sliding connections, wherein the sliding connections comprise one or more flexible loops formed from the single polymer fiber, the sliding connections being formed in the knitted cover and attached to a flexible portion of the support element, wherein a first flexible loop of the one or more flexible loops is attached to the distal strut and slides only along the distal strut and a second flexible loop of the one or more flexible loops is attached to the proximal strut and slides only along the proximal strut to permit radial sliding of the knitted cover relative to the support element at the distal strut and the proximal strut.

2. The stent assembly of claim 1, wherein the single polymer fiber has a diameter of 10 microns to 30 microns.

3. The stent assembly of claim 1, wherein the single polymer fiber and the apertures are sized to encourage growth of endothelial cells therethrough.

4. The stent assembly of claim 1, wherein the single polymer fiber of the knitted cover has slack to enable the knitted cover to expand upon radial expansion of the support element.

5. The stent assembly of claim 1, wherein the single polymer fiber is biodegradable or bioresorbable.

6. The stent assembly of claim 1, wherein the knitted cover has a coverage area of less than 25% of an area of the exterior of the support element.

7. The stent assembly of claim 1, wherein the knitted cover has a coverage area of less than 20% of an area of the exterior of the support element.

8. The stent assembly of claim 1, wherein the knitted cover has an approximate aperture size of 20 microns to 50 microns.

9. The stent assembly of claim 1, wherein the single polymer fiber comprises at least one of a thermoplastic polymer, a polyolefin elastomer, a thermosetic polymer, polyester, polyurethane, polyfluoropolymer, and nylon.

10. The stent assembly of claim 9, wherein the single polymer fiber comprises at least one heat-set polymer comprising polypropylene, polyethylene terephthalate (PET), nylon 6/6, polytetrafluoroethylene (PTFE), polyvinyl alcohol (PVA), polyurethane, and poly-l-lactide (PLLA).

11. The stent assembly of claim 1, wherein the knitted cover comprises 20 to 50 courses per cm.

12. The stent assembly of claim 1, further comprising a coating disposed on the knitted cover, the metal struts, or both.

13. The stent assembly of claim 12, wherein the coating comprises a polymer, hyaluronic acid, or hyaluronan.

14. The stent assembly of claim 12, which further comprises an active pharmaceutical agent eluted from the knitted cover, from a coating disposed over the knitted cover, or both.

15. The stent assembly of claim 14, wherein the pharmaceutical agent is time-released.

16. The stent assembly of claim 14, wherein the pharmaceutical agent is present in an amount comprising 1 microgram to 200 micrograms per square centimeter of surface area of the knitted cover, the coating disposed over the knitted cover, or both.

17. The stent assembly of claim 14, wherein the pharmaceutical agent is time-released over 2 hours to a plurality of months.

18. The stent assembly of claim 14, wherein the pharmaceutical agent comprises a zolimus, zotarolimus, sirolimus, tacrolimus, everolimus, or a combination thereof.

19. The stent assembly of claim 18, wherein the pharmaceutical agent further comprises an anti-proliferative agent, an antithrombotic agent, a growth factor inhibitor, a steroid or corticosteroid, a statin, or a combination thereof; wherein the anti-proliferative agent is present and comprises a taxane, vincritine, viblastine, a HMG-CoA reductase inhibitor, doxorubicin, colchicine, actinomycin D, mitomycin C, cyclosporine, mycophenolic acid, triazolopyrimidine, or a combination thereof; wherein the antithrombotic agent is present and comprises heparin, a heparin-like dextran derivative, acid citrate dextrose, coumadin, warfarin, streptokinase, anistreplase, tissue plasminogen activator (tPA), urokinase, abciximab, or a combination thereof; wherein the growth factor inhibitor is present and comprises tranilast, angiopeptin, or a combination thereof; wherein the steroid or corticosteroid is present and comprises cortisone, prednisolone, or both; wherein the statin is present and comprises simvastatin, lovastatin, or a combination thereof; or any combination of the foregoing.

20. The stent assembly of claim 12, further comprising an active pharmaceutical agent eluted from the support element, a coating disposed over the support element, or both.

21. The stent assembly of claim 20, wherein the pharmaceutical agent is time-released.

22. The stent assembly of claim 20, wherein the pharmaceutical agent is present in an amount comprising 1 microgram to 200 micrograms per square centimeter of surface area of the knitted cover, the coating disposed over the knitted cover, or both.

23. The stent assembly of claim 20, wherein the pharmaceutical agent is time-released over 2 hours to a plurality of months.

24. The stent assembly of claim 20, wherein the pharmaceutical agent comprises a zolimus, zotarolimus, sirolimus, tacrolimus, everolimus, or a combination thereof.

25. The stent assembly of claim 24, wherein the pharmaceutical agent further comprises an anti-proliferative agent, an antithrombotic agent, a growth factor inhibitor, a steroid or corticosteroid, a statin, or a combination thereof; wherein the anti-proliferative agent is present and comprises a taxane,-vincritine, viblastine, a HMG-CoA reductase inhibitor, doxorubicin, colchicine, actinomycin D, mitomycin C, cyclosporine, mycophenolic acid, triazolopyrimidine, or a combination thereof; wherein the antithrombotic agent is present and comprises heparin, a heparin-like dextran derivative, acid citrate dextrose, coumadin, warfarin, streptokinase, anistreplase, tissue plasminogen activator (tPA), urokinase, abciximab, or a combination thereof; wherein the growth factor inhibitor is present and comprises tranilast, angiopeptin, or a combination thereof; wherein the steroid or corticosteroid is present and comprises cortisone, prednisolone, or both; wherein the statin is present and comprises simvastatin, lovastatin, or a combination thereof; or any combination of the foregoing.

26. The stent assembly of claim 1,
wherein the tension of the sliding connections is controlled by tightening the one or more flexible loops,
wherein the distal strut and the proximal strut are formed in a zigzag pattern having a plurality of distal points and a plurality of proximal points,
wherein the first flexible loop is attached to a distal point of the distal strut and the second flexible loop is attached to a proximal point of the proximal strut,
wherein the first flexible loop is configured to travel between the distal point of the distal strut and a proximal point of the distal strut, wherein the second flexible loop is configured to travel between the proximal point of the proximal strut and a distal point of the proximal strut.

27. A method of stenting a carotid artery which comprises:
applying the stent assembly of claim 1 to the carotid artery of a patient in need of treatment; and expanding the stent assembly in situ in the carotid artery of the patient so as to trap debris dislodged from the body lumen during the stenting of the carotid artery.

28. The method of claim 27, wherein the expanding comprises from 2 mm to 8 mm.

29. The method of claim 27, wherein the applying and expanding reduces thrombosis in the carotid artery compared to applying and expanding a stent lacking the knitted cover.

30. A method of treating embolic showers at insertion of a catheter, which comprises applying the stent assembly of claim 1 and expanding the stent assembly in situ in the carotid artery of a patient.

\* \* \* \* \*

UNITED STATES PATENT AND TRADEMARK OFFICE
CERTIFICATE OF CORRECTION

PATENT NO. : 10,058,440 B2
APPLICATION NO. : 14/500759
DATED : August 28, 2018
INVENTOR(S) : Eli Bar, Zeev Asher Holzer and Ofir Paz Page 1 of 1

It is certified that error appears in the above-identified patent and that said Letters Patent is hereby corrected as shown below:

In the Claims

Claim 25 at Column 48, Line 36: Please change ",-vincritine" to --, vincritine--

Signed and Sealed this
Fifth Day of March, 2019

Andrei Iancu
*Director of the United States Patent and Trademark Office*